(12) United States Patent
Marasco et al.

(10) Patent No.: US 10,611,735 B2
(45) Date of Patent: Apr. 7, 2020

(54) TRIAZOLES AS KV3 INHIBITORS

(71) Applicant: AUTIFONY THERAPEUTICS LIMITED, London (GB)

(72) Inventors: Agostino Marasco, Verona (IT); Giuseppe Alvaro, Verona (IT); Anne Dècor, Verona (IT); Dieter Hamprecht, Verona (IT); Paolo Dambruoso, Verona (IT); Simona Tommasi, Verona (IT)

(73) Assignee: Autifony Therapeutics Limited, Stevenage (GB)

( * ) Notice: Subject to any disclaimer, the term of this patent is extended or adjusted under 35 U.S.C. 154(b) by 0 days.

(21) Appl. No.: 16/181,864

(22) Filed: Nov. 6, 2018

(65) Prior Publication Data

US 2019/0071405 A1    Mar. 7, 2019

Related U.S. Application Data

(63) Continuation of application No. 15/208,329, filed on Jul. 12, 2016, now Pat. No. 10,160,730, which is a continuation of application No. 14/403,048, filed as application No. PCT/GB2013/051347 on May 22, 2013, now Pat. No. 9,422,252.

(60) Provisional application No. 61/702,337, filed on Sep. 18, 2012.

(30) Foreign Application Priority Data

| May 22, 2012 | (GB) | 1209013.0 |
| May 22, 2012 | (GB) | 1209019.7 |
| May 22, 2012 | (GB) | 1209020.5 |
| Dec. 12, 2012 | (GB) | 1222393.9 |

(51) Int. Cl.
| C07D 401/04 | (2006.01) |
| C07D 249/12 | (2006.01) |
| C07D 405/14 | (2006.01) |
| C07D 307/94 | (2006.01) |
| C07D 311/04 | (2006.01) |
| C07D 311/76 | (2006.01) |
| C07D 311/96 | (2006.01) |
| C07D 307/87 | (2006.01) |
| C07C 43/313 | (2006.01) |
| C07C 255/46 | (2006.01) |
| C07C 43/29 | (2006.01) |
| C07C 255/37 | (2006.01) |
| C07C 43/225 | (2006.01) |
| C07C 255/48 | (2006.01) |

(52) U.S. Cl.
CPC .......... *C07D 249/12* (2013.01); *C07C 43/225* (2013.01); *C07C 43/29* (2013.01); *C07C 43/313* (2013.01); *C07C 255/37* (2013.01); *C07C 255/46* (2013.01); *C07C 255/48* (2013.01); *C07D 307/87* (2013.01); *C07D 307/94* (2013.01); *C07D 311/04* (2013.01); *C07D 311/76* (2013.01); *C07D 311/96* (2013.01); *C07D 401/04* (2013.01); *C07D 405/14* (2013.01); *C07C 2601/02* (2017.05)

(58) Field of Classification Search
CPC ...................................................... C07D 401/04
USPC ...................................................... 546/272.4
See application file for complete search history.

(56) References Cited

U.S. PATENT DOCUMENTS

| 4,350,701 A | 9/1982 | Costin et al. |
| 4,675,403 A | 6/1987 | Abou-Gharbia et al. |
| 4,804,671 A | 2/1989 | Costin et al. |
| 5,362,878 A | 11/1994 | Chang et al. |
| 5,607,932 A * | 3/1997 | Heeres ................. C07D 401/14 424/653 |
| 5,637,729 A | 6/1997 | Lacroix et al. |
| 5,656,634 A | 8/1997 | Chang et al. |
| 5,703,087 A | 12/1997 | Perregaard et al. |
| 5,728,834 A | 3/1998 | Nacharaju et al. |
| 9,422,252 B2 | 8/2016 | Marasco et al. |
| 2003/0008884 A1 | 1/2003 | Gerusz et al. |
| 2003/0149061 A1 | 8/2003 | Nishihara et al. |
| 2003/0187267 A1 | 10/2003 | Babin et al. |
| 2005/0009817 A1 | 1/2005 | Savoy et al. |
| 2005/0153968 A1 | 7/2005 | Bi et al. |

(Continued)

FOREIGN PATENT DOCUMENTS

| DE | 3836175 A1 | 5/1990 |
| EP | 0277842 A1 | 8/1988 |

(Continued)

OTHER PUBLICATIONS

Neill et al., Abstract European College of Neuropsychopharmacology conference "A novel Kv3 ion channel modulator restores cognitive function in an animal model of cognitive impairment in schizophrenia" Oct. 2013 (2 pages).

(Continued)

*Primary Examiner* — Patricia L Morris
(74) *Attorney, Agent, or Firm* — McDermott Will & Emery LLP

(57) ABSTRACT

Compounds of formula (I) are of use in the modulation of Kv3.1, Kv.3.2 and Kv3.3 channels and have utility in the treatment or prevention of related disorders.

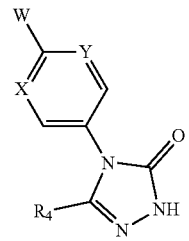

(I)

5 Claims, No Drawings

(56) References Cited

U.S. PATENT DOCUMENTS

| | | |
|---|---|---|
| 2007/0004753 A1 | 1/2007 | Sawyers et al. |
| 2007/0254933 A1 | 11/2007 | Jung et al. |
| 2008/0139634 A2 | 6/2008 | Jung et al. |
| 2008/0261961 A1 | 10/2008 | Flynn et al. |
| 2010/0158860 A1 | 6/2010 | Steiner et al. |
| 2010/0172975 A1 | 7/2010 | Sawyers et al. |
| 2010/0210665 A1 | 8/2010 | Sawyers et al. |
| 2011/0003839 A1 | 1/2011 | Jung et al. |
| 2011/0112097 A1 | 5/2011 | Jaehne et al. |
| 2011/0123490 A1 | 5/2011 | Schoenfeld et al. |
| 2012/0190718 A1 | 7/2012 | Jung et al. |
| 2012/0289526 A1 | 11/2012 | Alvaro |
| 2016/0318882 A1 | 11/2016 | Marasco et al. |

FOREIGN PATENT DOCUMENTS

| | | |
|---|---|---|
| EP | 0368008 A1 | 5/1990 |
| EP | 0726898 B1 | 8/1996 |
| EP | 1206935 A1 | 5/2002 |
| GB | 2216890 A | 10/1999 |
| JP | H10502383 A | 3/1998 |
| JP | 11-279129 A | 10/1999 |
| JP | 2000072731 A | 3/2000 |
| JP | 2000336071 A | 12/2000 |
| JP | 2007527897 A | 10/2007 |
| WO | 1991004027 A1 | 4/1991 |
| WO | 1996/01821 A1 | 1/1996 |
| WO | 199601821 A1 | 1/1996 |
| WO | 199636229 A1 | 11/1996 |
| WO | 1996036633 A1 | 11/1996 |
| WO | 1997000612 A1 | 1/1997 |
| WO | 1998005652 A1 | 2/1998 |
| WO | 1998023155 A1 | 6/1998 |
| WO | 1998023156 A1 | 6/1998 |
| WO | 1998033382 A1 | 8/1998 |
| WO | 2001076582 A1 | 10/2001 |
| WO | 2003048134 A1 | 6/2003 |
| WO | 2003066050 A1 | 8/2003 |
| WO | 2004074251 A1 | 9/2004 |
| WO | 2004099159 A1 | 11/2004 |
| WO | 2005000309 A1 | 1/2005 |
| WO | 2005049040 A1 | 6/2005 |
| WO | 2005049580 A1 | 6/2005 |
| WO | 2005/085226 A1 | 9/2005 |
| WO | 2005085226 A1 | 9/2005 |
| WO | 2006067139 A1 | 6/2006 |
| WO | 2006071471 A1 | 7/2006 |
| WO | 2006124118 A1 | 11/2006 |
| WO | 2007126765 A1 | 11/2007 |
| WO | 2007127010 A1 | 11/2007 |
| WO | 2010054279 A1 | 5/2010 |
| WO | 2010072598 A1 | 7/2010 |
| WO | 2011069951 A1 | 6/2011 |
| WO | 2011073114 A1 | 6/2011 |
| WO | 2012037132 A1 | 3/2012 |
| WO | 2012076877 A1 | 6/2012 |
| WO | 2012168710 A1 | 12/2012 |
| WO | 2013182851 A1 | 12/2012 |
| WO | 2013083994 A1 | 6/2013 |
| WO | 2013175211 A1 | 11/2013 |
| WO | 2013182850 A1 | 12/2013 |

OTHER PUBLICATIONS

Sidor et al., Abstract Society for Neuroscience Annual Meeting Oct. 2012 (1 page).

STN registry search cited in Second Office Action dated Sep. 9, 2016, issued in connection with Chinese Patent Application No. 201380026338.8.

CAS: 175783-04-7, Entered STN:May 2, 1996 (3H-1,2,4-Triazol-3-one, 4-(6-chloro-3-pyridinyl)-2,4-dihydro-); STN registry search cited in Second Office Action dated Sep. 9, 2016 issued in connection with Chinese Patent Application No. 201380026338.8.

CAS: 860612-51-7, Entered STN: Aug. 17, 2005 (3H-1,2,4-Triazol-3-one, 4-(4-promophenyl)-2,4-dihydro-5-methyl-); STN registry search cited in Second Office Action dated Sep. 9, 2016, issued in connection with Chinese Patent Application No. 201380026338.8.

Sheng et al, "Design and synthesis of novel triazole antifungal derivatives by structure-based bioisosterism", Eur. J. Med. Chem., 46, pp. 5276-5282, 2011.

Joho et al, "The Role of Kv3-type Potassium Channels in Cerebellar Physiology and Behavior", Cerebellum, 8, pp. 323-333, 2009.

Sargent et al., "Naturally Occurring Dibenzofurans. Part 1. A Synthesis of Cannabifuran", 7 Journal of the Chemical Society, Perkin Transactions 1: Organic and Bio-Organic Chemistry, 1605-1610, (1982).

Pilati et al., "Acoustic over-exposure triggers burst firing in dorsal cochlear nucleus fusiform cells", Hearing Research, 283, pp. 98-106, 2012.

Waters et al., "Mutations in voltage-gated potassium channel KCNC3 cause degenerative and developmental central nervous system phenotypes", Nature Genetics, 38, pp. 447-451, 2006.

Minassian et al., "Altered Kv3.3 channel gating in early-onset spinocerebellar ataxia type 13", J. Physiol., 590.7, pp. 1599-1614, 2012.

Campbell et al, "D-methionine (D-met) significantly rescues noise-induced hearing loss: Timing studies", Hearing Research, 282, pp. 138-144, 2011.

Jones et al., "Animal Modes of Schizophrenia", Brit. J. Pharmacol., 164, pp. 1162-1194, 2011.

Yanagi et al., "Kv3.1-containing K+ channels are reduced in untreated schizophrenia and normalized with antipsychotic drugs", Molecular Psychiatry, pp. 1-7, 2013.

Puente et al., "Precise localization of the voltage-gated potassium channel subunits Kv3.1b and Kv3.3 revealed in the molecular layer of the rat cerebellar cortex by a pre-embedding immunogold method", Histochem. Cell Biol., 134, pp. 403-409, 2010.

Roberts et al., "Ringing Ears: The Neuroscience of Tinnitus", J. Neurosci., 30, pp. 14972-14979, 2010.

Desai et al., "Protein Kinase C Modulates Inactivation of Kv3.3 Channels", J. Biol. Chem., 283, pp. 22283-22294, 2008.

Newman et al., "Development of the Tinnitus Handicap Inventory", Arch. Otolaryngol Head Neck Surg., 122, pp. 143-148, 1996.

Meikle et al., "The Tinnitus Functional Index: Development of a New Clinical Measure for Chronic, Intrusive Tinnitus", Ear & Hearinq, 33, pp. 153-176, 2012.

Jastreboff et al., "Neurophysiological model of tinnitus: Dependence of the minimal masking level on treatment outcome", Hearing Research, 80, pp. 216-232, 1994.

Nilsson et al., "Development of the Hearing in Noise Test for the measurement of speech reception thresholds in quiet and in noise", J. Acoust. Soc. Am., 95, pp. 1085-1099, 1994.

Mazelova et al., "Auditory function in presbycusis: preipheral vs. central changes", Experimental Gerontology, 38, pp. 87-94, 2003.

Turner, "Behavioral measures of tinnitus in laboratory animals", Prog. Brain Res., 166, pp. 147-156, 2007.

Syka, "The Fischer 344 rat as a model of presbycusis", Hearing Research, 264, pp. 70-78, 2010.

Figueroa et al, "KCNC3: phenotype, mutations, channel biophysics—a study of 260 familial ataxia patients", Human Mutation, 31(2):191-196, Feb. 2010.

Issa et al, "Spinocerebellar ataxia type 13 mutation associated with disease onset in infancy disrupts axonal pathfinding during neuronal development", Disease Models & Mechanisms, 5, pp. 921-929, 2012.

International Search Report and Written Opinion dated Jan. 25, 2013, issued in connection with PCT/GB2012/053045.

International Search Report and Written Opinion dated Jul. 8, 2013, issued in connection with PCT/GB2013/051343.

International Search Report and Written Opinion for PCT/EP2010/068946 dated Mar. 18, 2011.

International Search Report and Written Opinion dated Feb. 24, 2012, issued in connection with PCT/GB2011/052414.

Rudy and McBain, "Kv3 channels: voltage-gated K+ channels designed for high-frequency repetitive firing, Trends in Neurosciences", 24, 517-526, 2001.

(56) References Cited

OTHER PUBLICATIONS

Weiser et al., "Differential Expression of Shaw-related K+ Channels in the Rat Central Nervous System", J.Neurosci., 14, pp. 949-972, 1994.
Chow et al., "K+ Channel Expression Distinguishes Subpopulations of Parvalbumin- and Somatostatin-Containinq Neocortical Interneurons", J.Neurosci., 19, pp. 9332-9345, 1999.
Martina et al., "Functional and Molecular Differences between Voltage-Gated K+ Channels of Fast-spiking Interneurons and Pyramidal Neurons of Rat Hippocampus", J.Neurosci., 18, pp. 8111-8125, 1998.
McDonald and Mascagni, "Differential Expression of Kv3.1b and Kv3.2 Potassium Channel Subunits in Interneurons of the Basolateral Amygdala", J.Neurosci., 138, pp. 537-547, 2006.
International Search Report and Written Opinion dated Jul. 13, 2012, issued in connection with PCT/GB2012/051278.
Chang et al., "Distribution of Kv3.3 Potassium Channel Subunits in Distinct Neuronal Populations of Mouse Brain", J. Comp. Neural., 502, pp. 953-972, 2007.
Kasten et al., "Differential regulation of action potential firing in adult murine thalamocortical neurons by Kv3.2, Kv1 and SK potassium and N-type calcium channels", J.Physiol., 584, pp. 565-582, 2007.
Sacco et al., "Properties and expression of Kv3 channels is cerebellar Purkinje cells", Mol. Cell. Neurosci., 33, pp. 170-179, 2006.
Li et al., "Localization of Two High-Threshold Potassium Channel Subunits in the Rat Auditory System", J. Comp. Neural., 437, pp. 196-218, 2001.
Joho et al., "Increased γ- and Decreased δ-Oscillations in a Mouse Deficient for a Potassium Channel Expressed in Fast-Spiking Interneurons", J.Neurophysiol., 82, pp. 1855-1864, 1999.
Lau et al., "Impaired Fast-Spiking, Suppressed Cortical Inhibition, and Increased Susceptibility to Seizures in Mice Lacking Kv3.2 K+ Channel Proteins", J.Neurosci., 20, pp. 9071-9085, 2000.
McMahon et al., "Allele-dependent changes of olivocerebellar circuit properties in the absence of the voltaqe-qated potassium channels Kv3.1 and Kv3.3", Eur. J.Neurosci., 19, pp. 3317-3327, 2004.
Espinosa et al., "Alcohol Hypersensitivity, Increased Locomotion, and Spontaneous Myoclonus in Mice Lacking the Potassium Channels Kv3.1 and Kv3.3", J.Neurosci., 21, pp. 6657-6665, 2001.
Espinosa et al., "Ablation of Kv3.1 and Kv3.3 Potassium Channels Disrupts Thalamocortical Oscillations In Vitro and In Vivo", J.Neurosci., 28, pp. 5570-5581, 2008.
Diochot et al., "Sea Anemone Peptides with a Specific Blocking Activity against the Fast Inactivating Potassium Channel Kv3.4", J. Biol. Chem., 273, pp. 6744-6749, 1998.
Yeung et al., "Modulation of Kv3 Subfamily Potassium Currents by the Sea Anemone Toxin BOS: Significance for CNS and Biophysical Studies", J.Neurosci., 25, pp. 8735-8745, 2005.
Atzori et al., "H2 histamine receptor-phosphorylation of Kv3.2 modulates interneuron fast spiking", Nat. Neurosci., 3, pp. 791-798, 2000.
Song et al., "Acoustic environment determines phosphorylation state of the Kv3.1 potassium channel in auditory neurons", Nat Neurosci., 8, pp. 1335-1342, 2005.
Reynolds et al., "Calcium Binding Protein Markers of GABA Deficits in Schizophrenia—Post Mortem Studies and Animal Models", Neurotox. Res., 6, pp. 57-61, 2004.
Benes et al., "Circuitry based gene expression profiles in GABA cells of the trisynaptic pathway in schizophrenics versus bipolars", PNAS, 105, pp. 20935-20940, 2008.
Spencer et al., "Neural synchrony indexes disordered perception and cognition in schizophrenia", PNAS, 101, pp. 17288-17293, 2004.
Schulz and Steimer, Neurobiology of Circadian Systems, CNS Drugs, 23 Suppl 2, pp. 3-13, 2009.

Goldman and Holme, "Hearing loss and tinnitus—the hidden healthcare time bomb", Drug Discovery Today, 15, pp. 253-255, 2010.
B. Shield, Evaluation of the social and economic costs of hearing impairment, A report for Hear-It AISBL: www.hear-it.orq/multimedia/Hear_It_Report_October_2006.pdf, 2006.
Von Hehn et al., "Loss of Kv3.1 Tonotopicity and Alterations in cAMP Response Element-Binding Protein Signaling in Central Auditory Neurons of Hearing Impaired Mice", J. Neurosci., 24, pp. 1936-1940, 2004.
Jung et al., "Age-related changes in the distribution of Kv1.1 and Kv3.1 in rat cochlear nuclei", Neural. Res., 27, pp. 436-440, 2005.
Kaczmarek et al., "Regulation of the timing of MNTB neurons by short-term and long-term modulation of potassium channels", Hearing Res., 206, pp. 133-145, 2005.
Strumbos et al., "Specific and Rapid Effects of Acoustic Stimulation on the Tonotopic Distribution of Kv3.1b Potassium Channels in the Adult Rat", J. Neuroscience, 167, pp. 567-572, 2010.
Strumbos et al., "Fragile X Mental Retardation Protein is Required for Rapid Experience-Dependent Regulation of Potassium Channel Kv3.1b", J. Neuroscience, 167, pp. 10263-10271, 2010.
Berge et al.,"Pharmaceutical Salts", J. Pharm. Sci., 66, pp. 1-19, 1977.
Zhang et al., "Total synthesis and reassignment of stereochemistry of obyanamide", Tetrahedron, 62(42), pp. 9966-9972, 2006.
Stean, et al., "Postsynaptic 5-HT1B receptors modulate electroshock-induced generalised seizures in rats", Brit. J. Pharmacol., 144, pp. 628-635, 2005, 144(5) :628-35, 2005.
Costall, B. et al., "A Primate Model for the Assessment of Anxiolytic Drug Action", Br. J. Pharmac., 1988, 95, pp. 475P, 1988.
Brambilla et al., "GABAergic dysfunction in mood disorders", Mol. Psychiatry, 8, pp. 721-737, 2003.
Aroniadou-Anderjaska et al., "Mechanisms regulating GABAergic inhibitory transmission in the basolateral amygdala: Implications for epilepsy and anxiety disorders", Amino Acids, 32, pp. 305-315, 2007.
Ben-Ari, "Seizures Beget Seizures: The Quest for GABA as a Key Player", Grit. Rev. Neurobiol., 18, pp. 135-144, 2006.
Markram et al., "Interneurons of the Neocortical Inhibitory System", Nat.Rev.Neurosci., 5, pp. 793-807, 2004.
Fisahn, "Kainate receptors and rhythmic activity in neuronal networks: hippocampal gamma oscillations as a tool", J. Physiol, 562, oo 65-72, 2005.
Engel et al., "Dynamic Predictions: Oscillations and Synchrony in Top-Down Processing", Nat.Rev.Neurosci., 2, pp. 704-716, 2001.
Lewis et al., "Cortical parvalbumin interneurons and cognitive dysfunction in schizophrenia", Trends in Neurosciences, 35(1), pp. 57-67, 2012.
Lisman, "Excitation, inhibition, local oscillations, or large-scale loops: what causes the symptoms of schizophrenia?" Curr. Opin. Neurobiol., 22(3) pp. 537-544, 2012.
Jones et al, "Animal Models of Schizophrenia", Brit. J. Pharmacol., 164, pp. 1162-1194, 2011.
Bramness et al., "Amphetamine-induced psychosis—A separate diagnostic entity or primary osychosis triqqered in the vulnerable", BMC Psychiatry, 12, 221, 2012.
Harte et al., Abstract 4th Biennial Schizophrenia International Research Conference (Apr. 2014) "Efficacy and relevance of the modulation of Kv3 channels to alleviate cognitive dysfunction in an animal model of schizophrenia symptomatoloqy".
Mabrouck et al., Abstract 4th Biennial Schizophrenia International Research Conference (Apr. 2014) "A novel Kv3 positive modulator augments gamma frequency oscillations in the mammalian neocortex in vitro".
Leger et al., Abstract 4th Biennial Schizophrenia International Research Conference (Apr. 2014) "Two novel Kv3 ion channel modulators alleviate cognitive dysfunction and social behaviour deficits of relevance to schizophrenia in an animal model".

* cited by examiner

TRIAZOLES AS KV3 INHIBITORS

RELATED APPLICATIONS

This application is a continuation of U.S. patent application Ser. No. 15/208,329, filed Jul. 12, 2016 (allowed) which is a continuation of U.S. patent application Ser. No. 14/403,048, filed Nov. 21, 2014, now U.S. Pat. No. 9,422,252, which is a U.S. national phase of International Application No. PCT/GB2013/051347, filed May 22, 2013, which designated the U.S. and claims priority to GB Application No. 1209013.0, filed May 22, 2012; GB Application No. 1209019.7, filed May 22, 2012; GB Application No. 1209020.5, filed May 22, 2012; and GB Application No. 1222393.9, filed Dec. 12, 2012; and claims the benefit of U.S. Provisional Application No. 61/702,337, filed Sep. 18, 2012, the entire contents of each of which are hereby incorporated by reference for all purposes.

TECHNICAL FIELD

This invention relates to novel compounds, pharmaceutical compositions containing them and their use in therapy, in particular in the prophylaxis or treatment of hearing disorders, including hearing loss and tinnitus, as well as schizophrenia, bipolar disorder, epilepsy and sleep disorders.

BACKGROUND TO THE INVENTION

The Kv3 voltage-gated potassium channel family includes four members, Kv3.1, Kv3.2, Kv3.3, and Kv3.4. Genes for each of these subtypes can generate multiple isoforms by alternative splicing, producing versions with different C-terminal domains. Thirteen isoforms have been identified in mammals to date, but the currents expressed by these variants appear similar (Rudy and McBain, 2001, Trends in Neurosciences 24, 517-526). Kv3 channels are activated by depolarisation of the plasma membrane to voltages more positive than −20 mV; furthermore, the channels deactivate rapidly upon repolarisation of the membrane. These biophysical properties ensure that the channels open towards the peak of the depolarising phase of the neuronal action potential to initiate repolarisation. Rapid termination of the action potential mediated by Kv3 channels allows the neuron to recover more quickly to reach sub-threshold membrane potentials from which further action potentials can be triggered. As a result, the presence of Kv3 channels in certain neurons contributes to their ability to fire at high frequencies (Rudy and McBain, 2001, Trends in Neurosci. 24, 517-526). Kv3.1-3 subtypes are predominant in the CNS, whereas Kv3.4 channels are found predominantly in skeletal muscle and sympathetic neurons (Weiser et al., 1994, J. Neurosci. 14, 949-972). Kv3.1-3 channel subtypes are differentially expressed by sub-classes of interneurons in cortical and hippocampal brain areas (e.g. Chow et al., 1999, J. Neurosci. 19, 9332-9345; Martina et al., 1998, J. Neurosci. 18, 8111-8125; McDonald and Mascagni, 2006, Neurosci. 138, 537-547, Chang et al., 2007, J. Comp. Neurol. 502, 953-972), in the thalamus (e.g. Kasten et al., 2007, J. Physiol. 584, 565-582), cerebellum (e.g. Sacco et al., 2006, Mol. Cell. Neurosci. 33, 170-179; Puente et al., 2010, Histochem. Cell Biol. 134, 403-409), and auditory brain stem nuclei (Li et al., 2001, J. Comp. Neurol. 437, 196-218).

Kv3 channels are important determinants of the function of the cerebellum, a region of the brain important for motor control (Joho and Hurlock, 2009, Cerebellum 8, 323-333). Characterisation of mice in which one or more of the Kv3 subtypes has been deleted shows that the absence of Kv3.1 gives rise to increased locomotor activity, altered electroencephalographic activity, and a fragmented sleep pattern (Joho et al., 1999, J. Neurophysiol. 82, 1855-1864). The deletion of Kv3.2 leads to a reduction in seizure threshold and altered cortical electroencephalographic activity (Lau et al., 2000, J. Neurosci. 20, 9071-9085). Deletion of Kv3.3 is associated with mild ataxia and motor deficits (McMahon et al., 2004, Eur. J. Neurosci. 19, 3317-3327). Double deletion of Kv3.1 and Kv3.3 gives rise to a severe phenotype characterised by spontaneous seizures, ataxia, and an increased sensitivity to the effects of ethanol (Espinosa et al., 2001, J. Neurosci. 21, 6657-6665; Espinosa et al., 2008, J. Neurosci. 28, 5570-5581).

The known pharmacology of Kv3 channels is limited. Tetraethylammonium (TEA) has been shown to inhibit the channels at low millimolar concentrations (Rudy and McBain, 2001, Trends in Neurosci. 24, 517-526), and blood-depressing substance (BDS) toxins from the sea anemone, *Anemonia sulcata* (Diochot et al., 1998, J. Biol. Chem. 273, 6744-6749), have been shown to selectively inhibit Kv3 channels with high affinity (Yeung et al., 2005, J. Neurosci. 25, 8735-8745). In addition to compounds acting directly on Kv3 channels, agonists of receptors that activate protein kinase A (PKA) and protein kinase C (PKC) have been shown to modulate Kv3-mediated currents in specific brain areas, leading to a reduction in the ability of the neurons to fire at high frequency (Atzori et al., 2000, Nat. Neurosci. 3, 791-798; Song et al., 2005, Nat Neurosci. 8, 1335-1342); these studies suggest that PKA and PKC can specifically phosphorylate Kv3 channels in a neuron-specific manner, causing a reduction in Kv3-mediated currents.

Bipolar disorder, schizophrenia, anxiety, and epilepsy are serious disorders of the central nervous system that have been associated with reduced function of inhibitory interneurons and gamma-amino butyric acid (GABA) transmission (Reynolds et al., 2004, Neurotox. Res. 6, 57-61; Benes et al., 2008, PNAS, 105, 20935-20940; Brambilla et al., 2003, Mol. Psychiatry. 8, 721-37, 715; Aroniadou-Anderjaska et al., 2007, Amino Acids 32, 305-315; Ben-Ari, 2006, Crit. Rev. Neurobiol. 18, 135-144). Parvalbumin positive basket cells that express Kv3 channels in the cortex and hippocampus play a key role in generating feedback inhibition within local circuits (Markram et al., 2004, Nat. Rev. Neurosci. 5, 793-807). Given the relative dominance of excitatory synaptic input over inhibitory input to glutamatergic pyramidal neurons in these circuits, fast-firing of interneurons supplying inhibitory input is essential to ensure balanced inhibition. Furthermore, accurate timing of inhibitory input is necessary to sustain network synchronisation, for example, in the generation of gamma frequency field potential oscillations that have been associated with cognitive function (Fisahn et al., 2005, J. Physiol 562, 65-72; Engel et al., 2001, Nat. Rev. Neurosci. 2, 704-716). Notably, a reduction in gamma oscillations has been observed in patients with schizophrenia (Spencer et al., 2004, PNAS 101, 17288-17293). Consequently, positive modulators of Kv3 channels might be expected to enhance the firing capabilities of specific groups of fast-firing neurons in the brain. These effects may be beneficial in disorders associated with abnormal activity of these neuronal groups.

In addition, Kv3.2 channels have been shown to be expressed by neurons of the superchiasmatic nucleus (SCN) the main circadian pacemaker in the CNS (Schulz and Steimer, 2009, CNS Drugs 23 Suppl 2, 3-13).

Hearing loss represents an epidemic that affects approximately 16% of the population in Europe and the US (Goldman and Holme, 2010, Drug Discovery Today 15, 253-255), with a prevalence estimated at 250 million people worldwide (B. Shield, 2006, Evaluation of the social and economic costs of hearing impairment. A report for Hear-It AISBL: www.hear-it.org/multimedia/Hear_It_Report_October_2006.pdf). As life expectancy continues to increase, so too will the number of people suffering from hearing disorders. Furthermore, it is believed that modern lifestyles may exacerbate this burden as the younger generation ages. Hearing conditions, including tinnitus have a profound effect on the quality of life, causing social isolation, depression, work and relationship difficulties, low self-esteem, and prejudice. Voltage-gated ion channels of the Kv3 family are expressed at high levels in auditory brainstem nuclei (Li et al., 2001, J. Comp. Neurol. 437, 196-218) where they permit the fast firing of neurons that transmit auditory information from the cochlear to higher brain regions. Loss of Kv3.1 channel expression in central auditory neurons is observed in hearing impaired mice (von Hehn et al., 2004, J. Neurosci. 24, 1936-1940); furthermore, a decline in Kv3.1 expression may be associated with loss of hearing in aged mice (Jung et al. 2005 Neurol. Res. 27, 436-440), and loss of Kv3 channel function may also follow noise-trauma induced hearing loss (Pilati et al., Hear Res. 2012 January 283(1-2):98-106). Furthermore, pathological plasticity of auditory brainstem networks is likely to contribute to symptoms that are experienced by many people suffering from hearing loss of different types. Recent studies have shown that regulation of Kv3.1 channel function and expression has a major role in controlling auditory neuron excitability (Kaczmarek et al., 2005, Hearing Res. 206, 133-145), suggesting that this mechanism could account for some of the plastic changes that give rise to tinnitus. These data support the hypothesis that positive modulation of Kv3 channels in auditory brainstem nuclei could have a therapeutic benefit in patients suffering from hearing loss. Finally, Fragile X syndrome and autism are frequently associated with hypersensitivity to sensory input, including auditory stimuli. Recent findings suggest that the protein coded by the FMR-I gene, whose mutation or absence gives rise to Fragile X syndrome, may directly regulate the expression of Kv3.1 channels in the auditory brainstem nuclei (Strumbos et al., 2010, J. Neuroscience, in press), suggesting that mis-regulation of Kv3.1 channels could give rise to hyperacusis in patients suffering from Fragile X or autism. Consequently, we propose that small molecule modulators of Kv3 channels in auditory brainstem nuclei could have a benefit in the treatment of disorders of hearing, including tinnitus and auditory hyper-acuity associated with Fragile X syndrome and autism.

Kv 3.1 and Kv3.3 channels are expressed at high levels in auditory brainstem nuclei (Li et al., 2001, J. Comp. Neurol. 437, 196-218), and by neurons of the auditory nerve, which transmits auditory information from the cochlea to the auditory brainstem. Phosphorylation of Kv3.1 and Kv3.3 channels in auditory brainstem neurons is suggested to contribute to the rapid physiological adaptation to sound levels that may play a protective role during exposure to noise (Desai et al., 2008, J. Biol. Chem. 283, 22283-22294; Song et al., Nat. Neurosci. 8, 1335-1342). Furthermore, a loss of Kv3 channel function, which likely includes a loss of Kv3.3 channel function, has been shown to be associated with noise-trauma induced hearing loss (Pilati et al., 2012, Hear. Res. 283, 98-106) and may contribute the adaptive changes that give rise to tinnitus in many patients following noise-induced hearing loss. Tinnitus may follow noise-induced hearing loss as a result of adaptive changes in central auditory pathways from brainstem to auditory cortex (Roberts et al., 2010, J Neurosci. 30, 14972-14979). Kv3.1 and/or Kv3.2 channels are expressed in many of these circuits and contribute to the function of GABAergic inhibitory interneurons that may control the function of these circuits.

In some cases, hearing loss can occur rapidly over a period of hours or days. Such acute hearing loss may be caused by exposure to loud noise, ear infection or other idiopathic causes. The most common of these, noise-induced hearing loss was estimated to have a prevalence of 1.35% of the population in Western countries in 2009; thus affecting, for example, over 4 million Americans (Noise Induced Hearing Loss Market Report, prepared by RNID, 2009). Treatment for acute hearing loss is currently limited to oral or intratympanic administration of steroidal anti-inflammatory agents, such as dexamethasone; however, there is an urgent need for more effective treatments, and preferably treatments that can be administered safely by the oral route over a prolonged treatment period that could last from weeks to months.

These data support the hypothesis that modulation of Kv3.1 and/or Kv3.3 channels on the auditory nerve and/or on neurons in the auditory brainstem could have a therapeutic benefit in patients suffering hearing loss, including that caused by noise exposure, and modulation of Kv3.1 and/or Kv3.2 channels in higher auditory circuits may be beneficial in preventing the onset of tinnitus.

Spinocerebellar ataxia type 13 (SCA13) is a human autosomal dominant disease caused by mutations in the KCNC3 gene that encodes the Kv3.3 channel. SCA13 is either a neurodevelopmental disorder that is evident in infancy or a progressive neurodegenerative disease that emerges during adulthood (Figueroa et al., 2010, Hum Mutat. 31, 191-196). The known mutations in the KCNC3 gene have been shown to cause a reduction in function of the channels in some cases (Waters et al., 2006, Nat. Genet. 38, 447-451; Minassian et al., 2012, J Physiol. 590.7, 1599-1614), and a gain of function in other cases (Figueroa et al., 2011, PLoS ONE 6, e17811). For example, an F448L mutation alters channel gating and causes early-onset SCA13, whereas R420H and R423H mutations are associated with reduced Kv3 current amplitude by a dominant negative mechanism (Figueroa et al., 2010, Hum Mutat. 31, 191-196; Minassian et al., 2012, J Physiol. 590.7, 1599-1614). R420H leads to an adult form of SCA13, whereas R423H is associated with an early-onset ataxia. Early onset forms of SCA13 may be associated with deficits in the development of the cerebellum (Issa et al., 2012, Dis Model Mech. 5, 921-929), which are secondary to loss of Kv3.3 function. Coexpression of Kv3.1 and Kv3.3 in many brain areas, including the cerebellum suggests some redundancy or the ability of one subtype to compensate for the absence of the other, indeed the phenotype of the Kv3.1/Kv3.3 double knockout mice is markedly more severe than either of the two single knockouts (e.g. Espinosa et al., 2008, J. Neurosci. 28, 5570-5581). Furthermore, it is possible that Kv3.1 and Kv3.3 proteins assemble to form heteromeric channels in some neurons. The ability of Kv3.1 to compensate for a loss of function of Kv3.3 may explain why certain mutations in the latter are only associated with an onset of spinocerebellar ataxia later in adult life, rather than from birth (Minassian et al., 2012, J Physiol. 590.7, 1599-1614). Consequently, small molecule modulators of either Kv3.3 or Kv3.1 which are able to correct the deficits observed in the mutant channels, might be beneficial in the treatment of spinocerebellar ataxia, in particular SCA13.

Patent applications WO2011/069951, WO2012/076877 and WO2012/168710 (application number PCT/GB2012/051278) disclose compounds which are modulators of Kv3.1 and Kv3.2. Further, the value of such compounds is demonstrated in animal models of seizure, hyperactivity, sleep disorders, psychosis, hearing disorders and bipolar disorders. There remains a need for the identification of alternative modulators of Kv3.1 and Kv3.2, in particular modulators of Kv3.1 and Kv3.2 which may demonstrate channel selectivity or desirable pharmacokinetic parameters for example high brain availability. Furthermore, there remains a need for the identification of modulators of the Kv3.3 channel. Also desirable are modulators of Kv3 which may demonstrate high in vivo potency, channel selectivity or desirable pharmacokinetic parameters that reduce the dose required for therapeutic effect in vivo. For certain therapeutic indications, there is also a need to identify compounds with a different modulatory effect on Kv3 channels, for example, compounds that alter the kinetics of channel gating or channel inactivation, and which may behave in vivo as negative modulators of the channels.

SUMMARY OF THE INVENTION

The present invention provides a compound of formula (I):

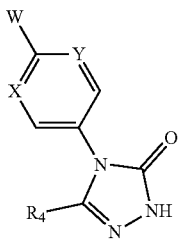
(I)

wherein:
W is group (Wa), group (Wb) or group (Wc):

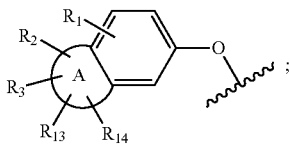
(Wa)

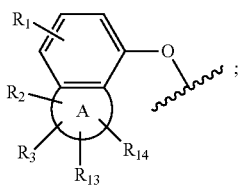
(Wb)

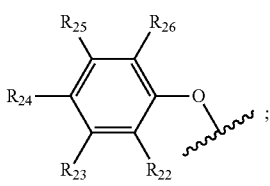
(Wc)

wherein:
$R_1$ is H, $C_{1-4}$alkyl, halo, halo$C_{1-4}$alkyl, CN, $C_{1-4}$alkoxy, or halo$C_{1-4}$alkoxy;
$R_2$ is H, $C_{1-4}$alkyl, $C_{3-5}$ spiro carbocyclyl, halo$C_{1-4}$alkyl or halo;
$R_3$ is H, $C_{1-4}$alkyl, halo$C_{1-4}$alkyl, halo; or $R_3$ is absent;
$R_{13}$ is H, $C_{1-4}$alkyl, halo$C_{1-4}$alkyl, halo; or $R_{13}$ is absent;
$R_{14}$ is H, $C_{1-4}$alkyl, halo$C_{1-4}$alkyl, halo; or $R_{14}$ is absent;
A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;
X is CH or N;
Y is $CR_{15}$ or N;
$R_{15}$ is H or $C_{1-4}$alkyl;
$R_{22}$ is H, Cl, F, $C_{1-4}$alkyl;
$R_{23}$ is H, $C_{1-4}$alkyl, Cl, $CF_3$, O—$C_{1-4}$alkyl, $OCF_3$ or $N(CH_3)_2$;
$R_{24}$ is H, Cl, F, $C_{1-4}$alkyl, O—$C_{1-4}$alkyl, CN, $OCF_3$ or $CF_3$;
$R_{25}$ is H, Cl, F, O—$C_{1-4}$alkyl or $C_{1-4}$alkyl; and
$R_{26}$ is H or $C_{1-4}$alkyl;
wherein for $R_{22}$ to $R_{26}$, $C_{1-4}$alkyl may be substituted by O-methyl;
with the provisos that:
not all of $R_{22}$ to $R_{26}$ may be H;
when $R_4$ is H, then $R_{23}$ is methyl or $CF_3$ and $R_{22}$, $R_{24}$, $R_{25}$ and $R_{26}$ are all H;
when one of $R_{22}$, $R_{24}$, $R_{25}$ or $R_{26}$ is F, then at least one of $R_{22}$ to $R_{26}$ cannot be H or F; and
when $R_{24}$ is not H, at least one of $R_{22}$ or $R_{23}$ is not H
$R_4$ is H or $C_{1-4}$ alkyl;
wherein $R_2$ and $R_3$ may be attached to the same or a different ring atom; $R_2$ may be attached to a fused ring atom; and wherein $R_{13}$ and $R_{14}$ may be attached to the same or a different ring atom.

Particular compounds of formula (I) are those wherein:
W is group (Wa) or group (Wb):

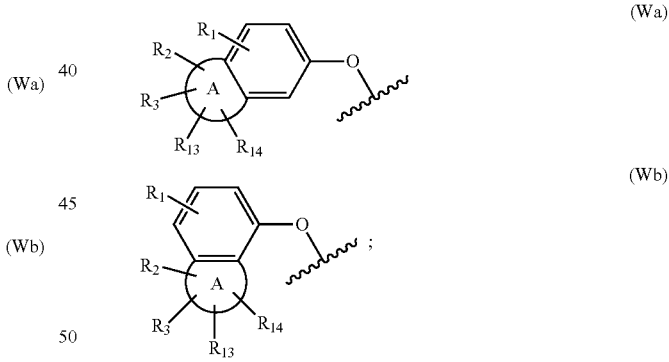

wherein:
$R_1$ is H, $C_{1-4}$alkyl, halo, halo$C_{1-4}$alkyl, CN, $C_{1-4}$alkoxy, or halo$C_{1-4}$alkoxy;
$R_2$ is H, $C_{1-4}$alkyl, $C_{3-5}$ spiro carbocyclyl, halo$C_{1-4}$alkyl or halo;
$R_3$ is H, $C_{1-4}$alkyl, halo$C_{1-4}$alkyl, halo; or $R_3$ is absent;
$R_{13}$ is H, $C_{1-4}$alkyl, halo$C_{1-4}$alkyl, halo; or $R_{13}$ is absent;
$R_{14}$ is H, $C_{1-4}$alkyl, halo$C_{1-4}$alkyl, halo; or $R_{14}$ is absent;
A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;
X is CH or N;
Y is $CR_{15}$ or N;

$R_{15}$ is H or $C_{1-4}$alkyl;
$R_4$ is H or $C_{1-4}$ alkyl;
wherein $R_2$ and $R_3$ may be attached to the same or a different ring atom; $R_2$ may be attached to a fused ring atom; and wherein $R_{13}$ and $R_{14}$ may be attached to the same or a different ring atom.

A compound of formula (I) may be provided in the form of a pharmaceutically acceptable salt and/or solvate thereof. In one embodiment of the invention a compound of formula (I) is provided in the form of a pharmaceutically acceptable salt.

The compounds of formula (I) may be used as medicaments, in particular for the prophylaxis or treatment of hearing disorders, including hearing loss and tinnitus, as well as schizophrenia, bipolar disorder, epilepsy and sleep disorders. Compounds of formula (I) may also be used as medicaments for the prophylaxis or treatment of spinocerebellar ataxia.

Further, there is provided a method for the prophylaxis or treatment of hearing disorders, including hearing loss and tinnitus, as well as schizophrenia, bipolar disorder, epilepsy and sleep disorders by administering to a subject a compound of formula (I). Still further, there is provided a method for the prophylaxis or treatment of spinocerebellar ataxia by administering to a subject a compound of formula (I).

Compounds of formula (I) may be used in the manufacture of a medicament for the prophylaxis or treatment of hearing disorders, including hearing loss and tinnitus, as well as schizophrenia, bipolar disorder, epilepsy and sleep disorders. Compounds of formula (I) may also be used in the manufacture of a medicament for the prophylaxis or treatment of spinocerebellar ataxia.

Also provided are pharmaceutical compositions containing a compound of formula (I) and a pharmaceutically acceptable carrier or excipient.

Additionally provided are prodrug derivatives of the compounds of formula (I).

DETAILED DESCRIPTION OF THE INVENTION

The present invention provides a compound of formula (I):

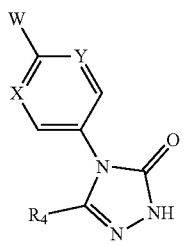

(I)

wherein:
W is group (Wa), group (Wb) or group (Wc):

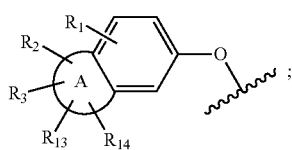

(Wa)

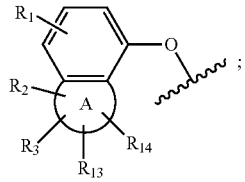

(Wb)

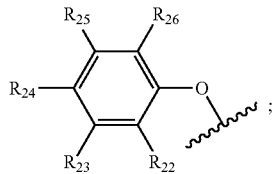

(Wc)

wherein:
$R_1$ is H, $C_{1-4}$alkyl, halo, halo$C_{1-4}$alkyl, CN, $C_{1-4}$alkoxy, or halo$C_{1-4}$alkoxy;
$R_2$ is H, $C_{1-4}$alkyl, $C_{3-5}$ spiro carbocyclyl, halo$C_{1-4}$alkyl or halo;
$R_3$ is H, $C_{1-4}$alkyl, halo$C_{1-4}$alkyl, halo; or $R_3$ is absent;
$R_{13}$ is H, $C_{1-4}$alkyl, halo$C_{1-4}$alkyl, halo; or $R_{13}$ is absent;
$R_{14}$ is H, $C_{1-4}$alkyl, halo$C_{1-4}$alkyl, halo; or $R_{14}$ is absent;
A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;
X is CH or N;
Y is $CR_{15}$ or N;
$R_{15}$ is H or $C_{1-4}$alkyl;
$R_{22}$ is H, Cl, F, $C_{1-4}$alkyl;
$R_{23}$ is H, $C_{1-4}$alkyl, Cl, $CF_3$, O—$C_{1-4}$alkyl, $OCF_3$ or $N(CH_3)_2$;
$R_{24}$ is H, Cl, F, $C_{1-4}$alkyl, O—$C_{1-4}$alkyl, CN, $OCF_3$ or $CF_3$;
$R_{25}$ is H, Cl, F, O—$C_{1-4}$alkyl or $C_{1-4}$alkyl; and
$R_{26}$ is H or $C_{1-4}$alkyl;
wherein for $R_{22}$ to $R_{26}$, $C_{1-4}$alkyl may be substituted by O-methyl;
with the provisos that:
not all of $R_{22}$ to $R_{26}$ may be H;
when $R_4$ is H, then $R_{23}$ is methyl or $CF_3$ and $R_{22}$, $R_{24}$, $R_{25}$ and $R_{26}$ are all H;
when one of $R_{22}$, $R_{24}$, $R_{25}$ or $R_{26}$ is F, then at least one of $R_{22}$ to $R_{26}$ cannot be H or F; and
when $R_{24}$ is not H, at least one of $R_{22}$ or $R_{23}$ is not H
$R_4$ is H or $C_{1-4}$ alkyl;
wherein $R_2$ and $R_3$ may be attached to the same or a different ring atom; $R_2$ may be attached to a fused ring atom; and wherein $R_{13}$ and $R_{14}$ may be attached to the same or a different ring atom.

Particular compounds of formula (I) are those wherein:
W is group (Wa) or group (Wb):

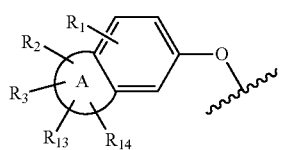

(Wa)

-continued

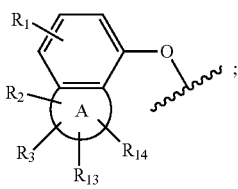
(Wb)

wherein:
R$_1$ is H, C$_{1-4}$alkyl, halo, haloC$_{1-4}$alkyl, CN, C$_{1-4}$alkoxy, or haloC$_{1-4}$alkoxy;
R$_2$ is H, C$_{1-4}$alkyl, C$_{3-5}$ spiro carbocyclyl, haloC$_{1-4}$alkyl or halo;
R$_3$ is H, C$_{1-4}$alkyl, haloC$_{1-4}$alkyl, halo; or R$_3$ is absent;
R$_{13}$ is H, C$_{1-4}$alkyl, haloC$_{1-4}$alkyl, halo; or R$_{13}$ is absent;
R$_{14}$ is H, C$_{1-4}$alkyl, haloC$_{1-4}$alkyl, halo; or R$_{14}$ is absent;
A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;
X is CH or N;
Y is CR$_{15}$ or N;
R$_{15}$ is H or C$_{1-4}$alkyl;
R$_4$ is H or C$_{1-4}$ alkyl;
wherein R$_2$ and R$_3$ may be attached to the same or a different ring atom; R$_2$ may be attached to a fused ring atom; and wherein R$_{13}$ and R$_{14}$ may be attached to the same or a different ring atom;
or a pharmaceutically acceptable salt and/or solvate thereof.

The present invention also provides a compound of formula (IA):

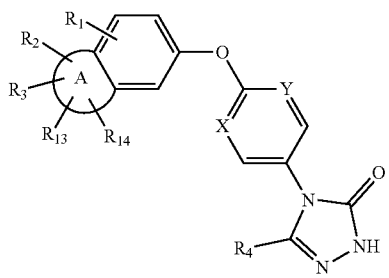
(IA)

wherein:
R$_1$ is H, C$_{1-4}$alkyl, halo, haloC$_{1-4}$alkyl, CN, C$_{1-4}$alkoxy, or haloC$_{1-4}$alkoxy;
R$_2$ is H, C$_{1-4}$alkyl, C$_{3-5}$ spiro carbocyclyl, haloC$_{1-4}$alkyl or halo;
R$_3$ is H, C$_{1-4}$alkyl, haloC$_{1-4}$alkyl, halo; or R$_3$ is absent;
R$_{13}$ is H, C$_{1-4}$alkyl, haloC$_{1-4}$alkyl, halo; or R$_{13}$ is absent;
R$_{14}$ is H, C$_{1-4}$alkyl, haloC$_{1-4}$alkyl, halo; or R$_{14}$ is absent;
A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;
X is CH or N;
Y is CR$_{15}$ or N;
R$_{15}$ is H or C$_{1-4}$alkyl;
R$_4$ is H or C$_{1-4}$ alkyl;
wherein R$_2$ and R$_3$ may be attached to the same or a different ring atom; R$_2$ may be attached to a fused ring atom; and wherein R$_{13}$ and R$_{14}$ may be attached to the same or a different ring atom;
or a pharmaceutically acceptable salt and/or solvate thereof.

The present invention also provides a compound of formula (IB):

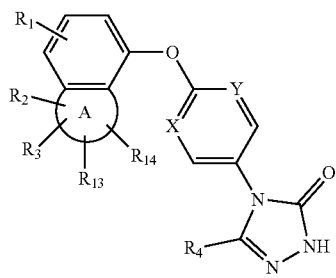
(IB)

wherein:
R$_1$ is H, C$_{1-4}$alkyl, halo, haloC$_{1-4}$alkyl, CN, C$_{1-4}$alkoxy, or haloC$_{1-4}$alkoxy;
R$_2$ is H, C$_{1-4}$alkyl, C$_{3-5}$ spiro carbocyclyl, haloC$_{1-4}$alkyl or halo;
R$_3$ is H, C$_{1-4}$alkyl, haloC$_{1-4}$alkyl, halo; or R$_3$ is absent;
R$_{13}$ is H, C$_{1-4}$alkyl, haloC$_{1-4}$alkyl, halo; or R$_{13}$ is absent;
R$_{14}$ is H, C$_{1-4}$alkyl, haloC$_{1-4}$alkyl, halo; or R$_{14}$ is absent;
A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;
X is CH or N;
Y is CR$_{15}$ or N;
R$_{15}$ is H or C$_{1-4}$alkyl;
R$_4$ is H or C$_{1-4}$ alkyl;
wherein R$_2$ and R$_3$ may be attached to the same or a different ring atom; R$_2$ may be attached to a fused ring atom; and wherein R$_{13}$ and R$_{14}$ may be attached to the same or a different ring atom;
or a pharmaceutically acceptable salt and/or solvate thereof.

The present invention also provides a compound of formula (IC):

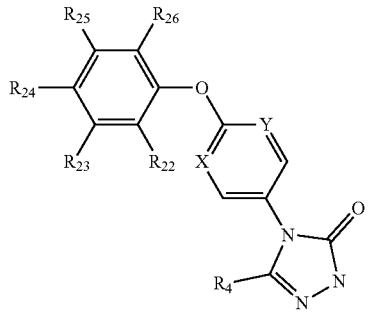
(IC)

wherein:
X is CH or N;
Y is CR$_{15}$ or N;
R$_{15}$ is H or C$_{1-4}$alkyl;
R$_{22}$ is H, Cl, F, C$_{1-4}$alkyl;

$R_{23}$ is H, $C_{1-4}$alkyl, Cl, $CF_3$, O—$C_{1-4}$alkyl, $OCF_3$ or $N(CH_3)_2$;

$R_{24}$ is H, Cl, F, $C_{1-4}$alkyl, O—$C_{1-4}$alkyl, CN, $OCF_3$ or $CF_3$;

$R_{25}$ is H, Cl, F, O—$C_{1-4}$alkyl or $C_{1-4}$alkyl; and $R_{26}$ is H or $C_{1-4}$alkyl;

wherein for $R_{22}$ to $R_{26}$, $C_{1-4}$alkyl may be substituted by O-methyl;

with the provisos that:

not all of $R_{22}$ to $R_{26}$ may be H;

when $R_4$ is H, then $R_{23}$ is methyl or $CF_3$ and $R_{22}$, $R_{24}$, $R_{25}$ and $R_{26}$ are all H;

when one of $R_{22}$, $R_{24}$, $R_{25}$ or $R_{26}$ is F, then at least one of $R_{22}$ to $R_{26}$ cannot be H or F; and when $R_{24}$ is not H, at least one of $R_{22}$ or $R_{23}$ is not H;

$R_4$ is H or $C_{1-4}$ alkyl;

or a pharmaceutically acceptable salt and/or solvate thereof.

Suitably, $R_1$ is H, $C_{1-4}$alkyl, halo or halo$C_{1-4}$alkyl. In another embodiment of the invention $R_1$ is H or methyl. In one embodiment of the invention $R_1$ is H. In another embodiment of the invention $R_1$ is $C_{1-4}$alkyl, in particular methyl. When W is group (Wa), suitably $R_1$ is H.

When W is group (Wb), suitably $R_1$ is H or methyl.

When W is group (Wb), suitably $R_1$ is positioned at the para position of the phenyl ring, as illustrated below:

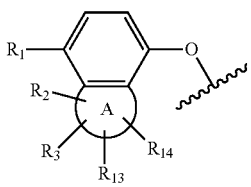

Suitably $R_2$ is H, $C_{1-4}$alkyl, $C_{3-5}$spiro carbocyclyl, or halo$C_{1-4}$alkyl. In one embodiment of the invention $R_2$ is $C_{1-4}$alkyl, in particular methyl, ethyl, isopropyl, tert-butyl or cyclopropyl, especially methyl, ethyl, isopropyl or tert-butyl. In one embodiment of the invention $R_2$ is $C_3$-5spiro carbocyclyl. In one embodiment of the invention $R_2$ is $C_3$spiro carbocyclyl. In another embodiment of the invention $R_2$ is $C_4$ spiro carbocyclyl. In a further embodiment of the invention $R_2$ is $C_5$spiro carbocyclyl. In one embodiment of the invention $R_2$ is halo$C_{1-4}$alkyl, in particular trifluoromethyl or 2,2,2-trifluoroethyl. In one embodiment of the invention $R_2$ is halo, in particular fluoro. In another embodiment of the invention $R_2$ is H.

In one embodiment of the invention $R_3$ is H, $C_{1-4}$alkyl, halo$C_{1-4}$alkyl or halo. Alternatively, $R_3$ is H, $C_{1-4}$alkyl, or halo$C_{1-4}$alkyl. Suitably $R_3$ is H or $C_{1-4}$alkyl. In one embodiment of the invention $R_3$ is H. In one embodiment of the invention $R_3$ is $C_{1-4}$alkyl, in particular methyl, ethyl, isopropyl, tert-butyl or cyclopropyl, especially methyl, ethyl, isopropyl or tert-butyl, such as methyl or ethyl. In one embodiment of the invention, $R_3$ is halo$C_{1-4}$alkyl, in particular trifluoromethyl or 2,2,2-trifluoroethyl. In one embodiment of the invention $R_3$ is halo, in particular fluoro. The skilled person will appreciate that, depending on the size, presence of heteroatoms and the degree of unsaturation of the A ring, $R_3$ may be absent. Consequently, in another embodiment of the invention $R_3$ is absent. In another embodiment of the invention $R_3$ is H. Suitably $R_3$ is H, methyl or trifluoromethyl.

In one embodiment of the invention $R_2$ may be H, $C_{1-4}$alkyl, halo$C_{1-4}$alkyl or $C_{3-5}$spiro carbocycyl and $R_3$ may be H, $C_{1-4}$alkyl, or halo$C_{1-4}$alkyl. In a particular embodiment of the invention, $R_2$ may be methyl, ethyl, isopropyl, tert-butyl, cyclopropyl, $C_{3-5}$spiro carbocyclyl, trifluoromethyl or 2,2,2-trifluoroethyl and $R_3$ may be H, methyl, ethyl or trifluoromethyl. In certain embodiments of the invention $R_3$ is H and $R_2$ is H, methyl, ethyl, isopropyl or $C_3$-4 spiro carbocyclyl. In further embodiments of the invention $R_3$ and $R_2$ are both fluoro (such as attached to the same ring carbon atom). In one embodiment of the invention $R_2$ is $C_{1-4}$alkyl and $R_3$ is H, for example $R_2$ is methyl, ethyl, tert-butyl or cyclopropyl. In one embodiment of the invention $R_2$ is $C_{1-4}$alkyl and $R_3$ is $C_{1-4}$alkyl, for example $R_2$ is methyl and $R_3$ is methyl, $R_2$ is ethyl and $R_3$ is ethyl or $R_2$ is methyl and $R_3$ is ethyl. In another embodiment of the invention $R_2$ is trifluoromethyl and $R_3$ is methyl.

In one embodiment of the invention $R_2$ and $R_3$ are attached to the same ring atom. In an alternative embodiment of the invention $R_2$ and $R_3$ are attached to different ring atoms.

In one embodiment of the invention $R_{13}$ is H, F or methyl. In one embodiment of the invention $R_{13}$ is H. In another embodiment of the invention $R_{13}$ is $C_{1-4}$alkyl, in particular methyl. In a further embodiment of the invention $R_{13}$ is halo, in particular fluoro. In an additional embodiment of the invention $R_{13}$ is halo$C_{1-4}$alkyl, such as trifluoromethyl. The skilled person will appreciate that, depending on the size, presence of heteroatoms and the degree of unsaturation of the A ring, $R_{13}$ may be absent. Consequently, in another embodiment of the invention $R_{13}$ is absent.

In one embodiment of the invention $R_{14}$ is H, F or methyl. In one embodiment of the invention $R_{14}$ is H. in another embodiment of the invention $R_{14}$ is $C_{1-4}$alkyl, in particular methyl. In a further embodiment of the invention $R_{14}$ is halo, in particular fluoro. In an additional embodiment of the invention $R_{13}$ is halo$C_{1-4}$alkyl, such as trifluoromethyl. The skilled person will appreciate that, depending on the size, presence of heteroatoms and the degree of unsaturation of the A ring, $R_{14}$ may be absent. Consequently, in another embodiment of the invention $R_{14}$ is absent.

In one embodiment of the invention $R_{13}$ and $R_{14}$ are attached to the same ring atom. In an alternative embodiment of the invention $R_{13}$ and $R_{14}$ are attached to different ring atoms. In certain embodiments of the invention $R_2$, $R_3$, $R_{13}$ and $R_{14}$ are each independently selected from H, $C_{1-4}$alkyl, halo$C_{1-4}$alkyl and halo, such as H, $C_{1-4}$alkyl and halo$C_{1-4}$alkyl. Suitably $R_2$, $R_3$, $R_{13}$ and $R_{14}$ are each independently selected from H, F, methyl and trifluoromethyl.

Suitably, A is a 5 or 6 membered saturated or unsaturated heterocycle, with at least one O atom; which heterocycle is optionally fused with a cyclopropyl group to form a tricycle when considered together with the phenyl. In one embodiment of the invention A is a 5 membered saturated or unsaturated heterocycle, with at least one O atom; which heterocycle is optionally fused with a cyclopropyl group, a cyclobutyl group or a cyclopentyl group to form a tricycle when considered together with the phenyl. In another embodiment of the invention A is a 6 membered saturated or unsaturated heterocycle, with at least one O atom; which heterocycle is optionally fused with a cyclopropyl group, a cyclobutyl group or a cyclopentyl group to form a tricycle when considered together with the phenyl.

In one embodiment of the invention A is a 5 membered saturated or unsaturated heterocycle with at least one O atom, which heterocycle is fused with a cyclopropyl group to form a tricycle when considered together with the phenyl. In another embodiment of the invention A is a 6 membered saturated or unsaturated heterocycle with at least one O atom, which heterocycle is fused with a cyclopropyl group to form a tricycle when considered together with the phenyl. In one embodiment of the invention A is a 5 membered saturated or unsaturated heterocycle with at least one O atom. In one embodiment of the invention A is a 6 membered saturated or unsaturated heterocycle with at least one O atom.

In certain embodiments of the invention the ring A contains one heteroatom. In other embodiments of the invention the ring A contains two heteroatoms (e.g. two oxygen atoms, one oxygen atom and one nitrogen atom, or one oxygen atom and one sulphur atom), in particular two oxygen atoms or one oxygen atom and one nitrogen atom.

Suitably, A is dihydrofuran, isoxazole, dihydropyran, 1,3-dioxolane, 1,3-oxazine or dihydropyran fused with a cyclopropyl group.

In one embodiment of the invention A is dihydrofuran. In one embodiment of the invention A is dihydropyran. In another embodiment of the invention A is dihydrofuran fused with a cyclopropyl group, a cyclobutyl group or a cyclopentyl group. In another embodiment of the invention A is dihydropyran fused with a cyclopropyl group, a cyclobutyl group or a cyclopentyl group. In a further embodiment the invention A is dihydrofuran fused with a cyclopropyl group. In still further embodiment the invention A is dihydropyran fused with a cyclopropyl group.

In one embodiment of the invention A is fused with a cyclopropyl group. In another embodiment A is fused with a cyclobutyl group. In a further embodiment of the invention A is fused with a cyclopentyl group. In one embodiment of the invention A is not fused with a cyclopropyl group, a cyclobutyl group or a cyclopentyl group.

In one embodiment of the invention W is group Wa:

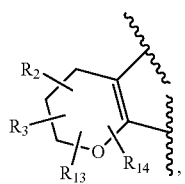

(Wa)

In one embodiment of the invention W is group Wb:

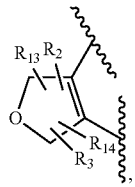

(Wb)

In one embodiment of the invention A is dihydrofuran, dihydropyran, furan, pyran, oxazole, isoxazole, oxazine, dioxine or 1,3-dioxalane. In another embodiment A is dihydrofuran, dihydropyran or 1,3-dioxalane.

In one embodiment of the invention A is:

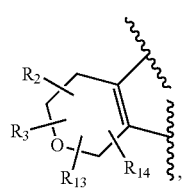

1

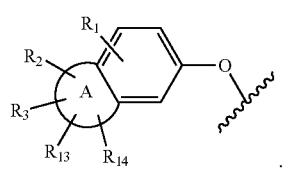

2

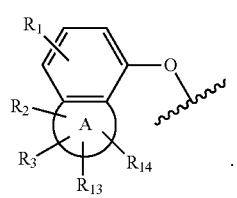

3

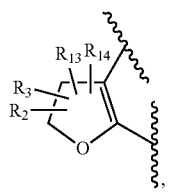

4

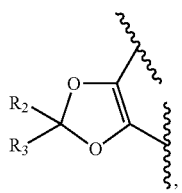

5

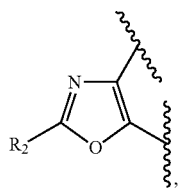

6

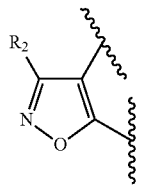

7

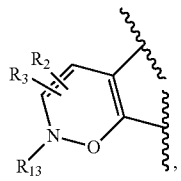

8

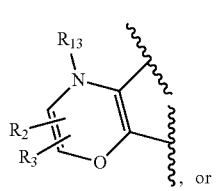

9

, or

-continued
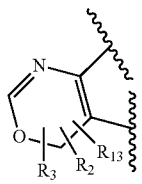
wherein
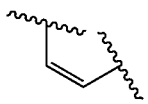
denotes a portion of the phenyl ring to which ring A is fused. In another embodiment of the invention A is:
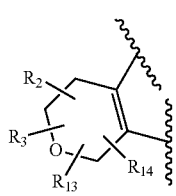
1
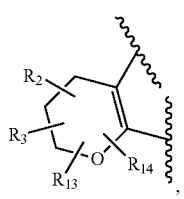
2
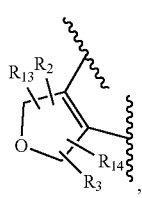
3
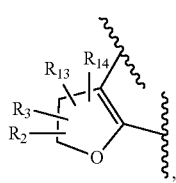
4
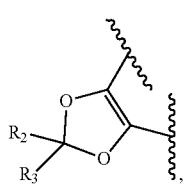
5
-continued
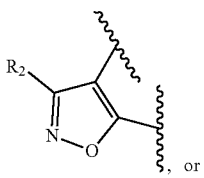
7
, or
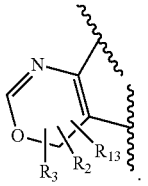
10
wherein
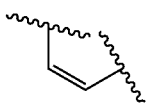 [SMILES: */C=C\*]
denotes a portion of the phenyl ring to which ring A is fused. In a further embodiment of the invention A is:
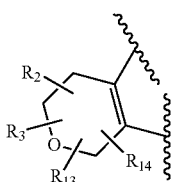
1
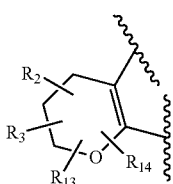
2
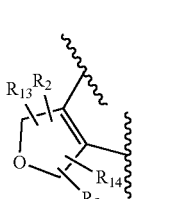
3
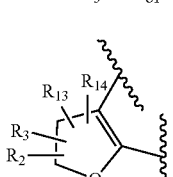
4
or
wherein
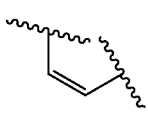
denotes a portion of the phenyl ring to which ring A is fused.

When A contains a 5 membered heterocycle containing one oxygen atom, suitably the heterocycle is dihydrofuran.

When A is a 5 membered heterocycle containing one oxygen atom, suitably the oxygen atom is located at the benzylic position relative to the phenyl ring.

When W is group Wa, suitably A is a 5 membered heterocycle containing one heteroatom, wherein the oxygen atom is located at the benzylic or para position relative to the phenyl ring.

When W is group Wb, suitably A is a 5 membered heterocycle containing one heteroatom, wherein the oxygen atom is located at the benzylic or meta position relative to the phenyl ring.

When W is group Wa, in one embodiment of the invention, Wa is:

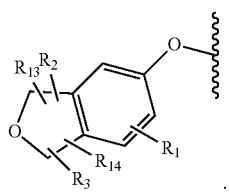

11

When W is group Wa, in another embodiment or the invention, Wa is:

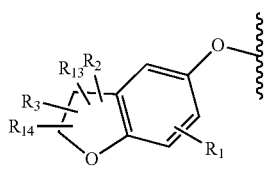

12

When W is group Wb, in one embodiment of the invention, Wb is:

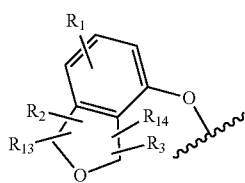

13

When W is group Wb, in another embodiment of the invention, Wb is:

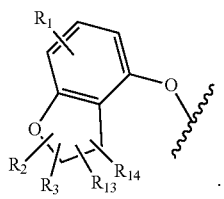

14

When W is group Wb, in a further embodiment of the invention, Wb is:

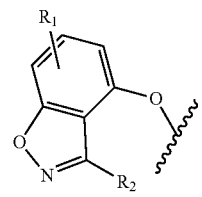

15

When A contains a 6 membered heterocycle containing one oxygen atom, suitably the heterocycle is dihydropyran.

When W is group Wa, suitably A is a 6 membered heterocycle containing one oxygen atom, wherein the oxygen atom is located at the para position relative to the phenyl ring.

When W is group Wb, suitably A contains a 6 membered heterocycle containing one oxygen atom, wherein the oxygen atom is located at the meta position relative to the phenyl ring.

When W is group Wa, in one embodiment of the invention, Wa is:

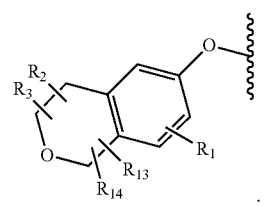

16

When W is group Wa, in another embodiment of the invention, Wa is:

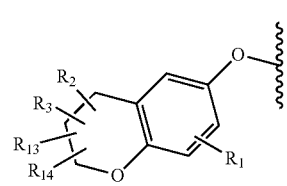

17

When W is group Wb, in one embodiment of the invention, Wb is:

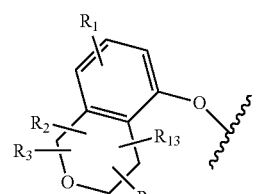

18

When W is group Wb, in one embodiment of the invention, Wb is:

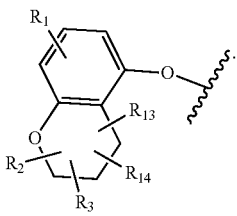

When W is group Wb, in one embodiment of the invention, Wb is:

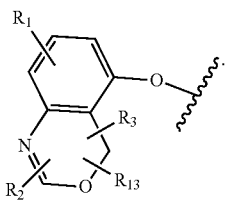

When W is group Wa, in one embodiment of the invention, A is:

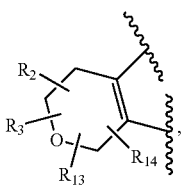

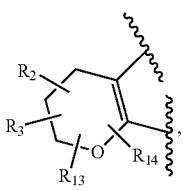

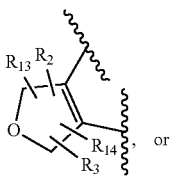

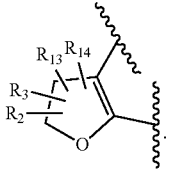

When W is group Wa, in one embodiment of the invention, A is:

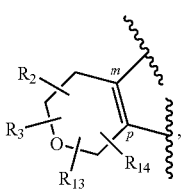

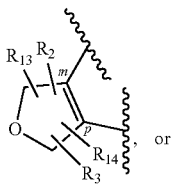

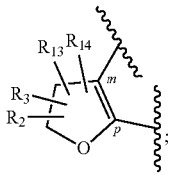

wherein m and p denote the meta and para positions, respectively, of ring A relative to the phenyl ring.

When W is group Wa, in a further embodiment of the invention, A is selected from the group consisting of:

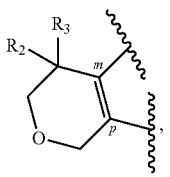

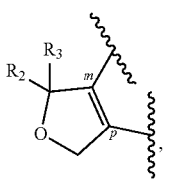

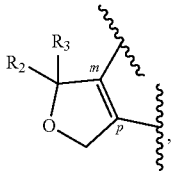

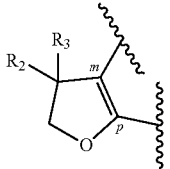, and

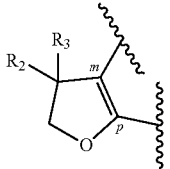

wherein m and p denote the meta and para positions, respectively, of ring A relative to the phenyl ring.

When W is group Wb, in one embodiment of the invention, A is:

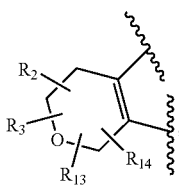

-continued
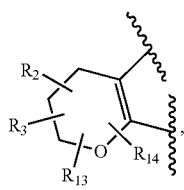
2
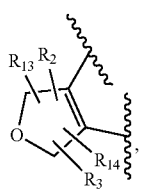
3
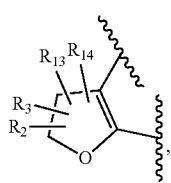
4
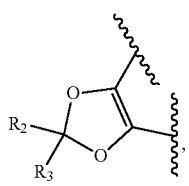
5
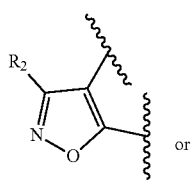
7
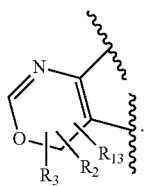
or
10
When W is group Wb, in one embodiment of the invention, A is:
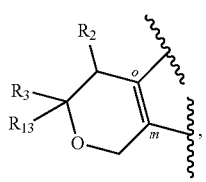
28
-continued
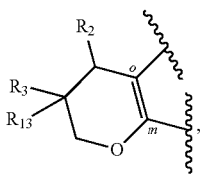
29
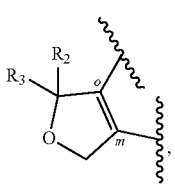
30
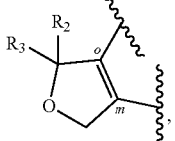
31
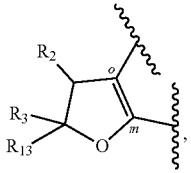
5
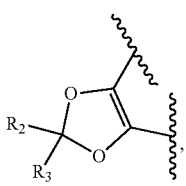
32
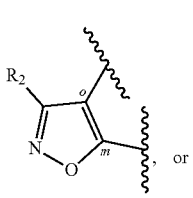
, or
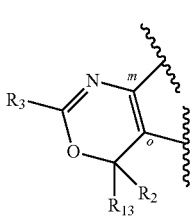
33
When W is group Wb, in one embodiment of the invention, A is:
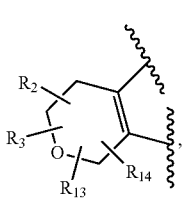
1

-continued

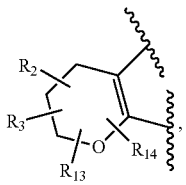

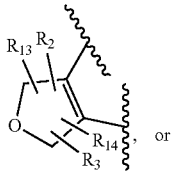

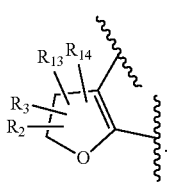

When W is group Wb, in another embodiment of the invention, A is:

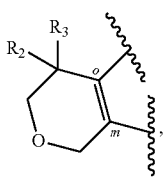

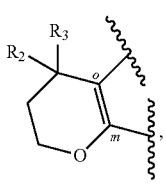

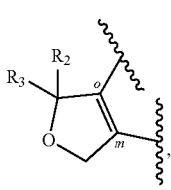

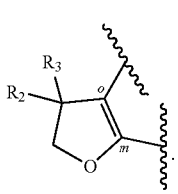

In one embodiment of the invention W is group Wc:

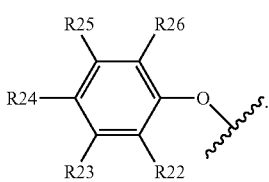

When W is group (Wc), suitably $R_{22}$, $R_{25}$ and $R_{26}$ are H. In one embodiment $R_{23}$ is $C_{1-4}$alkyl, Cl, $CF_3$, O—$C_{1-4}$alkyl, $OCF_3$ or $N(CH_3)_2$, such as $C_{1-2}$alkyl, $CF_3$, O—$C_{1-2}$alkyl or $OCF_3$, in particular $OCF_3$ and $R_{24}$ is H, Cl, F, $C_{1-4}$alkyl, O—$C_{1-4}$alkyl, CN, $OCF_3$, such as F, $C_{1-2}$alkyl, $CF_3$, O—$C_{1-2}$alkyl or $OCF_3$, in particular F or methyl and $R_{22}$, $R_{25}$ and $R_{26}$ are H.

Alternatively, when W is group (Wc), suitably four of $R_{22}$ to $R_{26}$ are H and one of $R_{22}$ to $R_{26}$, in particular $R_{22}$ or $R_{23}$, is other than H. When $R_{22}$ is other than H, suitably it is methyl. When $R_{23}$ is other than H, suitably it is $OCF_3$.

In one embodiment of the invention $R_4$ is H. In a further embodiment of the invention $R_4$ is $C_{1-4}$alkyl, in particular methyl, ethyl, isopropyl, tert-butyl or cyclopropyl. In one embodiment of the invention $R_4$ is methyl. In another embodiment of the invention $R_4$ is ethyl.

In one embodiment of the invention X is CH. In another embodiment of the invention X is N.

In one embodiment of the invention Y is $CR_{15}$. In another embodiment of the invention Y is N. In a further embodiment of the invention Y is $CR_{15}$, wherein $R_{15}$ is H. In a still further embodiment of the invention Y is $CR_{15}$, wherein $R_{15}$ is $C_{1-4}$alkyl, in particular methyl.

In one embodiment of the invention X is CH and Y is $CR_{15}$, wherein $R_{15}$ is H. In another embodiment of the invention X is N and Y is $CR_{15}$, wherein $R_{15}$ is H. In a further embodiment of the invention X is N and Y is $CR_{15}$, wherein $R_{15}$ is methyl. In a further embodiment of the invention X is CH and Y is $CR_{15}$, wherein $R_{15}$ is methyl. In a still further embodiment of the invention X is N and Y is N.

The invention provides a compound of formula (ICa):

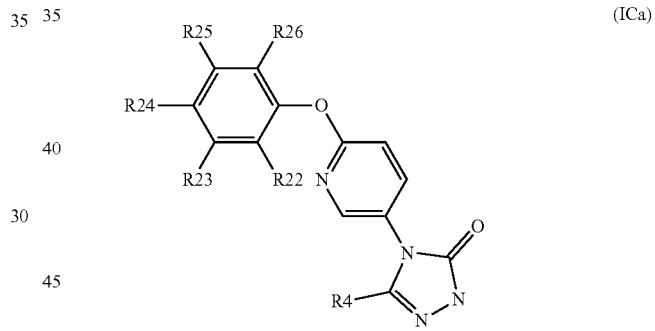

(ICa)

Wherein
$R_4$ is $CH_3$ or H;
$R_{22}$ is H, Cl, F, $C_{1-4}$alkyl;
$R_{23}$ is H, $C_{1-4}$alkyl, Cl, $CF_3$, O—$C_{1-4}$alkyl, $OCF_3$, $N(CH_3)_2$;
$R_{24}$ is H, Cl, F, $C_{1-4}$alkyl, O—$C_{1-4}$alkyl, CN, $OCF_3$, $CF_3$;
$R_{25}$ is H, Cl, F, O—$C_{1-4}$alkyl, $C_{1-4}$alkyl; and
$R_{26}$ is H, $C_{1-4}$alkyl;
wherein $C_{1-4}$alkyl may be substituted by O-methyl;
with the provisos that:
not all of $R_{22}$ to $R_{26}$ may be H;
when $R_4$ is H, then $R_{23}$ is methyl or $CF_3$ and $R_{22}$, $R_{24}$, $R_{25}$ and $R_{26}$ are all H;
when one of $R_{22}$, $R_{24}$, $R_{25}$ or $R_{26}$ is F, then $R_{22}$ to $R_{26}$ cannot be H or F; and
when $R_{24}$ is not H, at least one of $R_{22}$ or $R_{23}$ is not H;
or a pharmaceutically acceptable salt thereof.

In one embodiment of the compounds of formula (ICa) $R_4$ is H.

In one embodiment of the compounds of formula (ICa) $R_4$ is methyl.

In one embodiment of the compounds of formula (ICa) $R_{22}$ is H.

In one embodiment of the compounds of formula (ICa) $R_{22}$ is $C_{1-4}$alkyl. In another embodiment $R_{22}$ is methyl. In a further embodiment $R_{22}$ is ethyl. In a yet further embodiment $R_{22}$ is propyl.

In one embodiment of the compounds of formula (ICa) $R_{22}$ is Cl.

In one embodiment of the compounds of formula (ICa) $R_{22}$ is F.

In one embodiment of the compounds of formula (ICa) $R_{23}$ is H.

In one embodiment of the compounds of formula (ICa) $R_{23}$ is $C_{1-4}$ alkyl. In another embodiment of the compounds of formula (ICa) $R_{23}$ is methyl.

In one embodiment of the compounds of formula (ICa) $R_{23}$ is chloro.

In one embodiment of the compounds of formula (ICa) $R_{23}$ is methoxy. In another embodiment of the compounds of formula (ICa) $R_{23}$ is ethoxy.

In one embodiment of the compounds of formula (ICa) $R_{23}$ is trifluoromethyl.

In one embodiment of the compounds of formula (ICa) $R_{23}$ is trifluoromethoxy.

In one embodiment of the compounds of formula (ICa) $R_{23}$ is $N(CH_3)_2$.

In one embodiment of the compounds of formula (ICa) $R_{24}$ is H.

In one embodiment of the compounds of formula (ICa) $R_{24}$ is methyl.

In one embodiment of the compounds of formula (ICa) $R_4$ is chloro.

In one embodiment of the compounds of formula (ICa) $R_{24}$ is fluoro.

In one embodiment of the compounds of formula (ICa) $R_{25}$ is H.

In one embodiment of the compounds of formula (ICa) $R_{25}$ is methyl.

In one embodiment of the compounds of formula (ICa) $R_{25}$ is chloro.

In one embodiment of the compounds of formula (ICa) $R_{25}$ is fluoro.

In one embodiment of the compounds of formula (ICa) $R_{26}$ is H.

In one embodiment of the compounds of formula (ICa) $R_{26}$ is methyl.

The invention also provides a compound of formula (ICb):

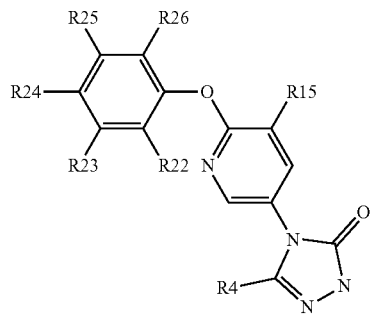

(ICb)

Wherein:
$R_4$ is H or Me
$R_{23}$ is $C_3-C_4$ alkyl or $OC_2-C_4$alkyl and $R_{22}$ is H, or $R_{22}$ and $R_{23}$ are both methyl;

$R_{24}$, $R_{25}$ and $R_{26}$ are H;
$R_{15}$ is H or methyl;
or a pharmaceutically acceptable salt thereof.

In one embodiment of the compounds of formula (ICb) $R_4$ is H.

In one embodiment of the compounds of formula (ICb) $R_4$ is methyl.

In one embodiment of the compounds of formula (ICb) $R_{22}$ is H.

In one embodiment of the compounds of formula (ICb) $R_{22}$ is methyl.

In one embodiment of the compounds of formula (ICb) $R_{23}$ is $C_3-C_4$ alkyl. In another embodiment of the compounds of formula (ICb) $R_{23}$ is propyl.

In one embodiment of the compounds of formula (ICb) $R_{23}$ is methyl.

In one embodiment of the compounds of formula (ICb) $R_{23}$ is $OC_2-C_4$alkyl. In another embodiment of the compounds of formula (ICb) $R_{23}$ is ethoxy.

In one embodiment of the compounds of formula (ICb) $R_{24}$ is H.

In one embodiment of the compounds of formula (ICb) $R_{25}$ is H.

In one embodiment of the compounds of formula (ICb) $R_{26}$ is H.

In one embodiment of the compounds of formula (ICb) $R_{15}$ is H.

In one embodiment of the compounds of formula (ICb) $R_{15}$ is methyl.

References to "formula (I)" should also be construed as also referring to formula (IA), formula (IB), formula (IC), formula (ICa), formula (ICb) as appropriate to the circumstances.

Suitably the compound of formula (I) is selected from:
4-{6-[(3,3-dimethyl-2,3-dihydro-1-benzofuran-4-yl)oxy]pyridin-3-yl}-5-methyl-2,4-dihydro-3H-1,2,4-triazol-3-one;
4-{6-[(3,3-diethyl-1,3-dihydro-2-benzofuran-5-yl)oxy]pyridin-3-yl}-5-methyl-2,4-dihydro-3H-1,2,4-triazol-3-one;
4-{6-[(3-tert-butyl-1,3-dihydro-2-benzofuran-5-yl)oxy]pyridin-3-yl}-5-methyl-2,4-dihydro-3H-1,2,4-triazol-3-one (enantiomer 1);
4-{6-[(3-tert-butyl-1,3-dihydro-2-benzofuran-5-yl)oxy]pyridin-3-yl}-5-methyl-2,4-dihydro-3H-1,2,4-triazol-3-one (enantiomer 2);
5-methyl-4-(6-{[3-methyl-3-(trifluoromethyl)-1,3-dihydro-2-benzofuran-5-yl]oxy}pyridin-3-yl)-2,4-dihydro-3H-1,2,4-triazol-3-one (enantiomer 1);
5-methyl-4-(6-{[3-methyl-3-(trifluoromethyl)-1,3-dihydro-2-benzofuran-5-yl]oxy}pyridin-3-yl)-2,4-dihydro-3H-1,2,4-triazol-3-one (enantiomer 2);
5-methyl-4-[6-(3H-spiro[2-benzofuran-1,1'-cyclobutan]-6-yloxy)pyridin-3-yl]-2,4-dihydro-3H-1,2,4-triazol-3-one;
5-methyl-4-[6-(3H-spiro[2-benzofuran-1,1'-cyclopentan]-6-yloxy)pyridin-3-yl]-2,4-dihydro-3H-1,2,4-triazol-3-one;
4-{6-[(3-tert-butyl-1,3-dihydro-2-benzofuran-4-yl)oxy]pyridin-3-yl}-5-methyl-2,4-dihydro-3H-1,2,4-triazol-3-one;
5-methyl-4-{6-[(3,3,7-trimethyl-2,3-dihydro-1-benzofuran-4-yl)oxy]-3-pyridinyl})-2,4-dihydro-3H-1,2,4-triazol-3-one;
4-{6-[(3,3-dimethyl-2,3-dihydro-1-benzofuran-4-yl)oxy]-5-methylpyridin-3-yl}-5-methyl-2,4-dihydro-3H-1,2,4-triazol-3-one;
5-methyl-4-[5-methyl-6-(spiro[1-benzofuran-3,1'-cyclopropan]-4-yloxy)pyridin-3-yl]-2,4-dihydro-3H-1,2,4-triazol-3-one;

5-methyl-4-{5-methyl-6-[(7-methylspiro[1-benzofuran-3,1'-cyclopropan]-4-yl)oxy]pyridin-3-yl}-2,4-dihydro-3H-1,2,4-triazol-3-one;

5-methyl-4-{6-[(7-methylspiro[1-benzofuran-3,1'-cyclopropan]-4-yl)oxy]pyridin-3-yl}-2,4-dihydro-3H-1,2,4-triazol-3-one;

5-methyl-4-[6-(spiro[1-benzofuran-3,1'-cyclopropan]-4-yloxy)pyridin-3-yl]-2,4-dihydro-3H-1,2,4-triazol-3-one; and 5-methyl-4-{2-[(7-methylspiro[1-benzofuran-3,1'-cyclopropan]-4-yl)oxy]pyrimidin-5-yl}-2,4-dihydro-3H-1,2,4-triazol-3-one.

In one embodiment of the invention the compound is selected from the group consisting of:

5-methyl-4-(4-{[4-methyl-3-(methyloxy)phenyl]oxy}phenyl)-2,4-dihydro-3H-1,2,4-triazol-3-one;

5-methyl-4-(4-{[3-(methyloxy)phenyl]oxy}phenyl)-2,4-dihydro-3H-1,2,4-triazol-3-one;

4-{4-[(3-ethylphenyl)oxy]phenyl}-5-methyl-2,4-dihydro-3H-1,2,4-triazol-3-one;

4-{4-[(2,6-dimethylphenyl)oxy]phenyl}-5-methyl-2,4-dihydro-3H-1,2,4-triazol-3-one;

4-(4-{[4-chloro-3-(methyloxy)phenyl]oxy}phenyl)-5-methyl-2,4-dihydro-3H-1,2,4-triazol-3-one;

4-(4-{[4-fluoro-3-(methyloxy)phenyl]oxy}phenyl)-5-methyl-2,4-dihydro-3H-1,2,4-triazol-3-one;

4-{4-[(3-chlorophenyl)oxy]phenyl}-5-methyl-2,4-dihydro-3H-1,2,4-triazol-3-one;

4-{4-[(3,4-dichlorophenyl)oxy]phenyl}-5-methyl-2,4-dihydro-3H-1,2,4-triazol-3-one;

4-{4-[(2,4-dichlorophenyl)oxy]phenyl}-5-methyl-2,4-dihydro-3H-1,2,4-triazol-3-one;

4-{4-[(3-chloro-2-fluorophenyl)oxy]phenyl}-5-methyl-2,4-dihydro-3H-1,2,4-triazol-3-one;

4-(4-{[3-chloro-5-(methyloxy)phenyl]oxy}phenyl)-5-methyl-2,4-dihydro-3H-1,2,4-triazol-3-one;

5-methyl-4-[4-({3-[(trifluoromethyl)oxy]phenyl}oxy)phenyl]-2,4-dihydro-3H-1,2,4-triazol-3-one;

4-{4-[(3-methylphenyl)oxy]phenyl}-5-methyl-2,4-dihydro-3H-1,2,4-triazol-3-one;

5-methyl-4-(4-{[3-(trifluoromethyl)phenyl]oxy}phenyl)-2,4-dihydro-3H-1,2,4-triazol-3-one;

4-{4-[(3-chloro-4-fluorophenyl)oxy]phenyl}-5-methyl-2,4-dihydro-3H-1,2,4-triazol-3-one;

4-{4-[(3-chloro-5-fluorophenyl)oxy]phenyl}-5-methyl-2,4-dihydro-3H-1,2,4-triazol-3-one;

4-{4-[(2,3-dimethylphenyl)oxy]phenyl}-5-methyl-2,4-dihydro-3H-1,2,4-triazol-3-one;

5-methyl-4-(4-{[2-methyl-5-(methyloxy)phenyl]oxy}phenyl)-2,4-dihydro-3H-1,2,4-triazol-3-one;

4-{4-[(3,4-dimethylphenyl)oxy]phenyl}-5-methyl-2,4-dihydro-3H-1,2,4-triazol-3-one;

4-{4-[(3,5-dimethylphenyl)oxy]phenyl}-5-methyl-2,4-dihydro-3H-1,2,4-triazol-3-one;

4-{4-[(2,5-dimethylphenyl)oxy]phenyl}-5-methyl-2,4-dihydro-3H-1,2,4-triazol-3-one;

5-methyl-4-{4-[(2-methylphenyl)oxy]phenyl}-2,4-dihydro-3H-1,2,4-triazol-3-one;

4-{4-[(2-ethylphenyl)oxy]phenyl}-5-methyl-2,4-dihydro-3H-1,2,4-triazol-3-one;

5-methyl-4-(4-{[3-(1-methylethyl)phenyl]oxy}phenyl)-2,4-dihydro-3H-1,2,4-triazol-3-one;

4-(4-{[3-(dimethylamino)phenyl]oxy}phenyl)-5-methyl-2,4-dihydro-3H-1,2,4-triazol-3-one;

4-{4-[(2-fluoro-6-methylphenyl)oxy]phenyl}-5-methyl-2,4-dihydro-3H-1,2,4-triazol-3-one;

5-methyl-4-(4-{[2-methyl-3-(methyloxy)phenyl]oxy}phenyl)-2,4-dihydro-3H-1,2,4-triazol-3-one;

4-(4-{[3-(ethyloxy)phenyl]oxy}phenyl)-5-methyl-2,4-dihydro-3H-1,2,4-triazol-3-one;

4-{4-[(3-methylphenyl)oxy]phenyl}-2,4-dihydro-3H1,2,4-triazol-3-one;

4-(4-{[3-trifluoromethyl)phenyl]oxy}phenyl)-2,4-dihydro-3H-1,2,4-triazol-3-one;

or a pharmaceutically acceptable salt thereof.

In another embodiment the compound is:

4-[4-[4-fluoro-3-(trifluoromethoxy)phenoxy]phenyl]-3-methyl-1H-1,2,4-triazol-5-one; or a pharmaceutically acceptable salt thereof.

In one embodiment of the invention the compound is selected from the group consisting of:

5-methyl-4-(5-methyl-6-{[3-(1-methylethyl)phenyl]oxy}-3-pyridinyl)-2,4-dihydro-3H-1,2,4-triazol-3-one;

4-(6-{[3-(ethyloxy)phenyl]oxy}-5-methyl-3-pyridinyl)-5-methyl-2,4-dihydro-3H-1,2,4-triazol-3-one;

4-{6-[(2,3-dimethylphenyl)oxy]-3-pyridinyl}-5methyl-2,4-dihydro-3H-,2,4-triazol-3-one;

4-(6-{[3-(1-methylethyl)phenyl]oxy}-3-pyridinyl)-2,4-dihydro-3H-1,2,4-triazol-3-one;

5-methyl-4-(6-{[3-(1-methylethyl)phenyl]oxy}-3-pyridinyl)-2,4-dihydro-3H-1,2,4-triazol-3-one;

4-(6-{[2-(1,1-dimethylethyl)phenyl]oxy}-3-pyridinyl)-5-methyl-2,4,dihydro-3H-1,2,4triazol-3-one;

or a pharmaceutically acceptable salt thereof.

In another embodiment the compound is:

5-methyl-4-{6-[4-methyl-3-(trifluoromethoxy)phenoxy]pyridin-3-yl}-2,4-dihydro-3H-1,2,4-triazol-3-one;

or a pharmaceutically acceptable salt thereof.

Suitably, the compound of formula (I) contains a W group corresponding to one of the following phenol groups:

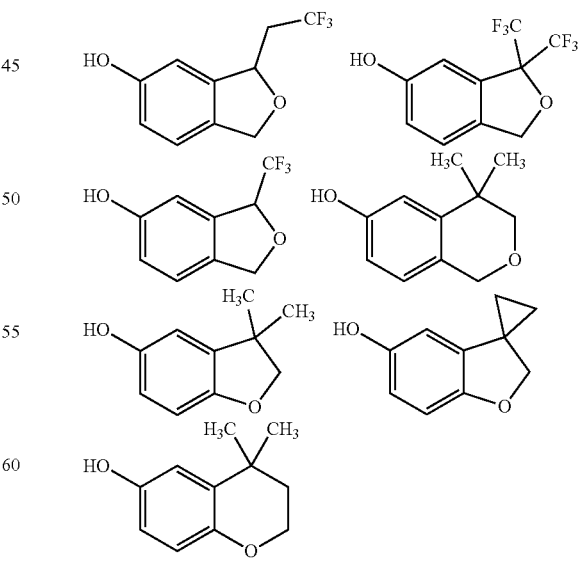

Suitably, the compound of formula (I) may contain a W group corresponding to one of the following phenol groups:

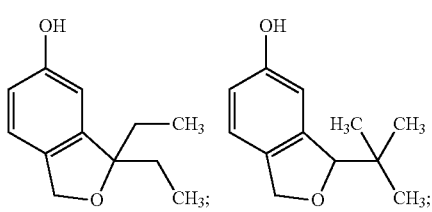

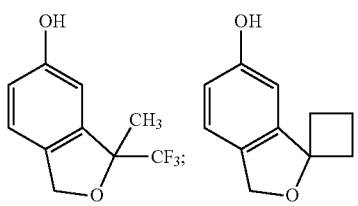

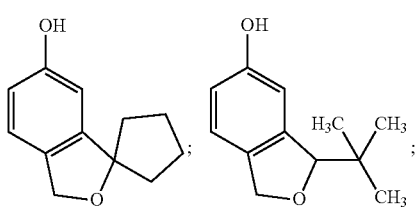

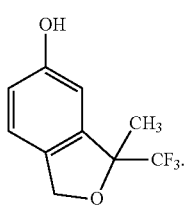

Suitably, the compound of formula (I) contains a W group corresponding to one of the following phenol groups:

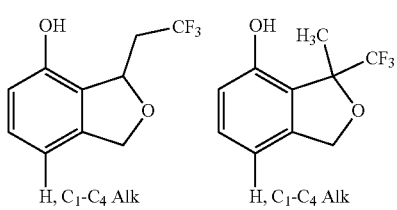

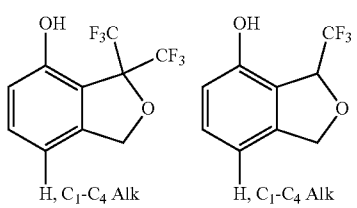

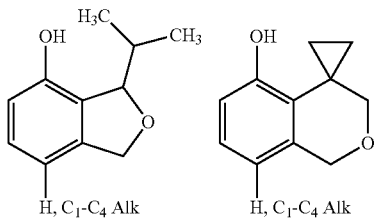

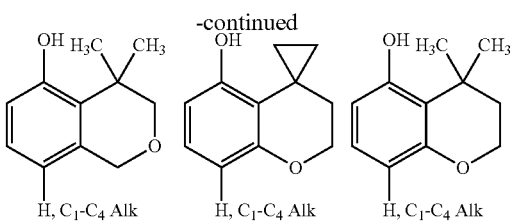

Alternatively, the compound of formula (I) contains a (Wb) group corresponding to one of the following phenol groups:

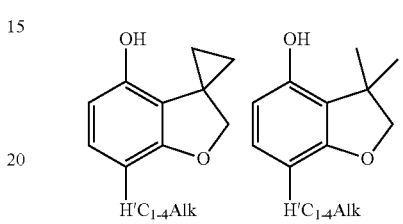

Alternatively, the compound of formula (I) may contain a (Wb) group corresponding to one of the following phenol groups:

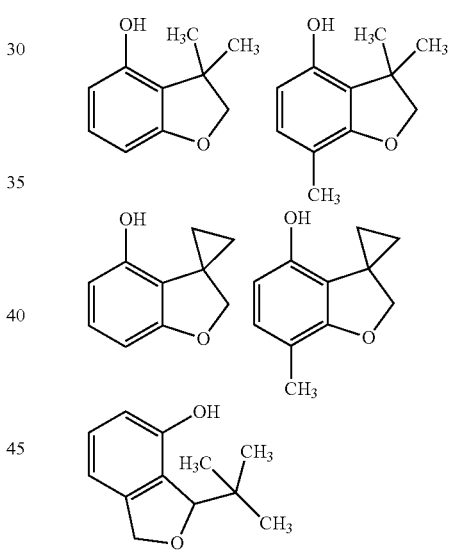

For the avoidance of doubt, the embodiments of any one feature of the compounds of the invention may be combined with any embodiment of another feature of compounds of the invention to create a further embodiment.

The term 'halo' or 'halogen' as used herein, refers to a fluorine, chlorine, bromine or iodine atom. Particular examples of halo are fluorine and chlorine, especially fluorine.

When the compound contains a $C_{1-4}$alkyl group, whether alone or forming part of a larger group, e.g. $C_{1-4}$alkoxy, the alkyl group may be straight chain, branched, cyclic, or a combination thereof. Examples of $C_{1-4}$alkyl are methyl, ethyl, n-propyl, isopropyl, n-butyl, isobutyl, sec-butyl, tert-butyl, cyclopropyl and cyclobutyl. A particular group of exemplary $C_{1-4}$alkyl groups are methyl, ethyl, n-propyl, isopropyl, n-butyl, isobutyl, sec-butyl, tert-butyl. An example of $C_{1-4}$alkoxy is methoxy.

When the compound contains a $C_{3-4}$alkyl group, whether alone or forming part of a larger group, e.g. $C_{2-4}$alkoxy, the alkyl group may be straight chain, branched, cyclic, or a combination thereof. Examples of $C_{3-4}$alkyl are n-propyl, isopropyl, n-butyl, isobutyl, sec-butyl, tert-butyl, cyclopropyl and cyclobutyl. An example of $C_{2-4}$alkoxy is ethoxy.

The term 'halo$C_{1-4}$alkyl' as used herein, includes straight chain, branched chain or cyclic alkyl groups containing 1 to 4 carbon atoms substituted by one or more halo atoms, for example fluoromethyl, difluoromethyl and trifluoromethyl. A particular group of exemplary halo$C_{1-4}$ alkyl include methyl and ethyl groups substituted with one to three halo atoms, in particular one to three fluoro atoms, such as trifluoromethyl or 2,2,2-trifluoroethyl.

The term 'halo$C_{1-4}$alkoxy' as used herein, includes straight chain, branched chain or cyclic alkoxy groups containing 1 to 4 carbon atoms substituted by one or more halo atoms, for example fluoromethoxy, difluoromethoxy and trifluoromethoxy. A particular group of exemplary halo$C_{1-4}$ alkyl include methoxy and ethoxy groups substituted with one to three halo atoms, in particular one to three fluoro atoms.

The term '5 or 6 membered saturated or unsaturated heterocycle, with at least one O atom' includes for example dihydrofuran, dihydropyran, furan, pyran, oxazole, isoxazole, oxazine, dioxine, morpholine or 1,3-dioxalane.

It will be appreciated that for use in medicine the salts of the compounds of formula (I) should be pharmaceutically acceptable. Suitable pharmaceutically acceptable salts will be apparent to those skilled in the art. Pharmaceutically acceptable salts include those described by Berge, Bighley and Monkhouse J. Pharm. Sci. (1977) 66, pp 1-19. Such pharmaceutically acceptable salts include acid addition salts formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates, may be used, for example in the isolation of compounds of formula (I) and are included within the scope of this invention.

Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form and, if crystalline, may optionally be solvated, e.g. as the hydrate. This invention includes within its scope stoichiometric solvates (e.g. hydrates) as well as compounds containing variable amounts of solvent (e.g. water).

It will be understood that the invention includes pharmaceutically acceptable derivatives of compounds of formula (I) and that these are included within the scope of the invention.

As used herein "pharmaceutically acceptable derivative" includes any pharmaceutically acceptable prodrug such as an ester or salt of such ester of a compound of formula (I) which, upon administration to the recipient is capable of providing (directly or indirectly) a compound of formula (I) or an active metabolite or residue thereof.

Suitably, a pharmaceutically acceptable prodrug is formed by functionalising the secondary nitrogen of the triazolone, for example with a group "L" as illustrated below:

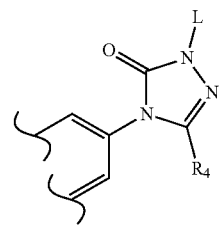

In one embodiment of the invention, a compound of formula (I) is functionalised via the secondary nitrogen of the triazolone with a group L, wherein L is selected from:
a) —PO(OH)O$^-$.M$^+$, wherein M$^+$ is a pharmaceutically acceptable monovalent counterion,
b) —PO(O$^-$)$_2$.2M$^+$,
c) —PO(O$^-$)$_2$.D$^{2+}$, wherein D$^{2+}$ is a pharmaceutically acceptable divalent counterion,
d) —CH(R$^X$)—PO(OH)O$^-$.M$^+$, wherein R$^X$ is hydrogen or $C_{1-3}$ alkyl,
e) —CH(R$^X$)—PO(O$^-$)$_2$.2M$^+$,
f) —CH(R$^X$)—PO(O$^-$)$_2$.D$^{2+}$
g) —SO$_3^-$.M$^+$,
h) —CH(R$^X$)—SO$_3^-$.M$^+$, and
i) —CO—CH$_2$CH$_2$—CO$_2$.M$^+$.

It is to be understood that the present invention encompasses all isomers of formula (I) and their pharmaceutically acceptable derivatives, including all geometric, tautomeric and optical forms, and mixtures thereof (e.g. racemic mixtures). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The subject invention also includes isotopically-labelled compounds which are identical to those recited in formula (I) but for the fact that one or more atoms are replaced by an atom having an atomic mass or mass number different from the atomic mass or mass number most commonly found in nature, or in which the proportion of an atom having an atomic mass or mass number found less commonly in nature has been increased (the latter concept being referred to as "isotopic enrichment"). Examples of isotopes that can be incorporated into compounds of the invention include isotopes of hydrogen, carbon, nitrogen, oxygen, fluorine, iodine and chlorine such as $^2$H (deuterium), $^3$H, $^{11}$C, $^{13}$C, $^{14}$C, $^{18}$F, $^{123}$I or $^{125}$I (e.g. $^3$H, $^{11}$C, $^{14}$C, $^{18}$F, $^{123}$I or $^{125}$I), which may be naturally occurring or non-naturally occurring isotopes.

Compounds of the present invention and pharmaceutically acceptable salts of said compounds that contain the aforementioned isotopes and/or other isotopes of other atoms are within the scope of the present invention. Isotopically labelled compounds of the present invention, for example those into which radioactive isotopes such as $^3$H or $^{14}$C have been incorporated, are useful in drug and/or substrate tissue distribution assays. Tritiated, i.e. $^3$H, and carbon-14, i.e. $^{14}$C, isotopes are particularly preferred for their ease of preparation and detectability. $^{11}$C and $^{18}$F isotopes are particularly useful in PET (positron emission tomography).

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis).

Impure preparations of the compounds may be used for preparing the more pure forms used in the pharmaceutical compositions.

According to a further aspect of the present invention there is provided a process for the preparation of compounds of formula (I) and derivatives thereof. The following schemes detail synthetic routes to compounds of the invention. In the following schemes reactive groups can be protected with protecting groups and deprotected according to well established techniques.

In general, the compounds of formula (I) may be made according to the organic synthesis techniques known to those skilled in this field, as well as by the representative methods set forth below, those in the Examples, and modifications thereof.

Patent applications WO2011/069951, WO2012/076877 and WO2012/168710 provide methods for the synthesis of intermediates which may be of use in the production of compounds of the present invention.

In the following description, the groups A, $R_1$, $R_2$, X, Y, $R_3$, $R_4$, $R_{13}$, $R_{14}$, $R_{15}$, $R_{22}$, $R_{23}$, $R_{24}$, $R_{25}$, $R_{26}$ have the meanings as previously defined for compounds of formula (I) unless otherwise stated.

microwave heating in a solvent, e.g. methanol or in a solvent free manner. Optionally, in a second stage, a base for example sodium methoxide can be added.

step (i): Compounds of formula (IV) are present as an isomers' mixture (E/Z) and can be prepared in situ or before by reaction of compounds of formula (V) wherein Ry is methyl or ethyl with alkyl carbazate of formula (VI) wherein Rx is methyl or ethyl in presence of a catalytic amount of p-toluensulfonic acid in a solvent e.g. methanol with heating e.g. at 60° C.

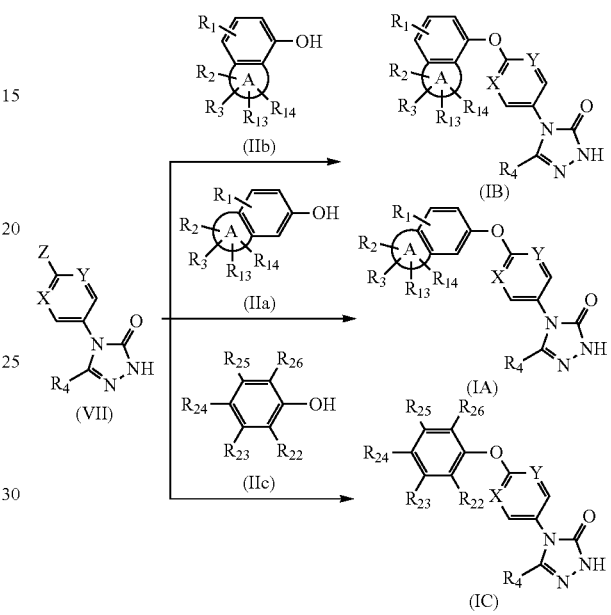

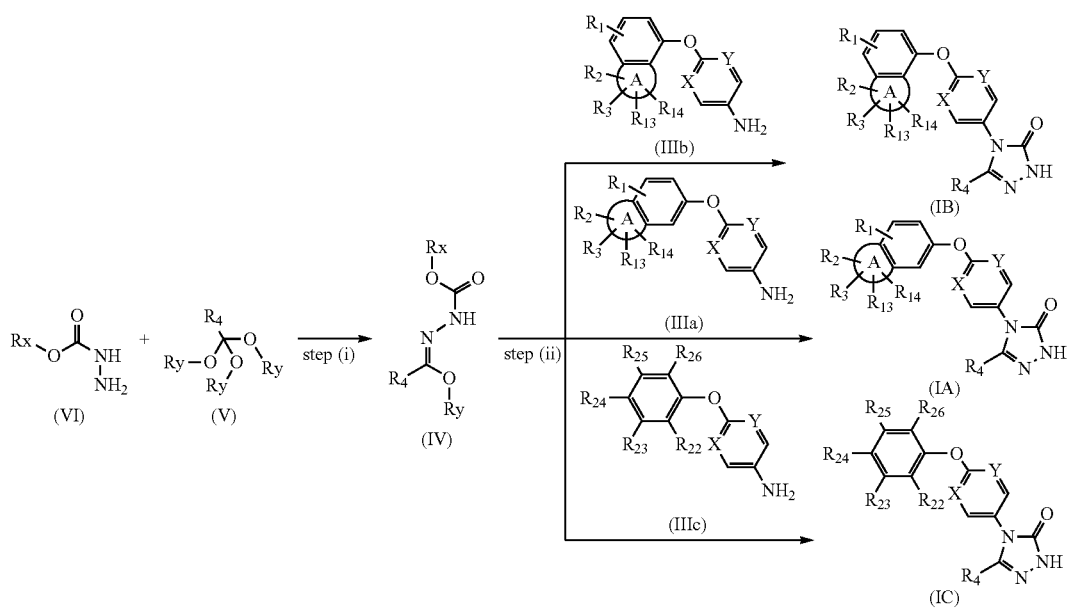

wherein Rx and Ry are methyl or ethyl.

step (ii): Compounds of formula (IA), (IB) and (IC) can be prepared by reaction of anilines of formula (IIIa) (IIIb) and (IIIc) with compounds of formula (IV) by heating at temperature ranging from 70° C. to 120° C. with regular or Compounds of formula (IA), (IB) and (IC) wherein X=N and Y=CR$_{15}$ or N can be prepared by nucleophilic aromatic substitution. In this reaction a pyridine or pyrimidine derivative of formula (VII) wherein Z=F or Cl and a phenol of formula (IIa), (IIb) or (IIc) are used in presence of a base such as potassium carbonate in a solvent e.g. in N,N-dimethylformamide or acetonitrile or N-Methylpyrrolidone with regular heating or microwave one at temperature ranging from 60° C. to reflux.

Alternatively, compounds of formula (IA), (IB) and (IC) wherein X=N or C and Y=CR$_{15}$ or N can be prepared from a phenyl, pyridine or pyrimidine derivative of formula (VII) wherein Z=I, Br or Cl and a phenol of formula (IIa), (IIb) or (IIc) using Ullmann-coupling conditions.

Scheme 3

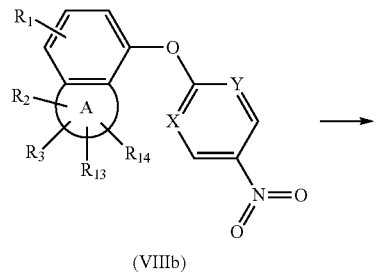

(VIIIb)

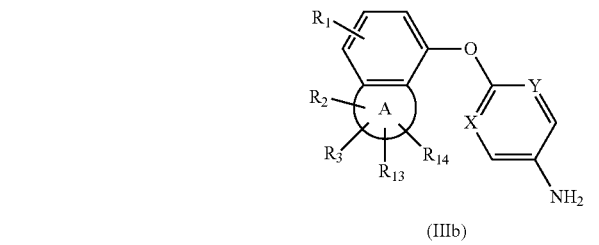

(IIIb)

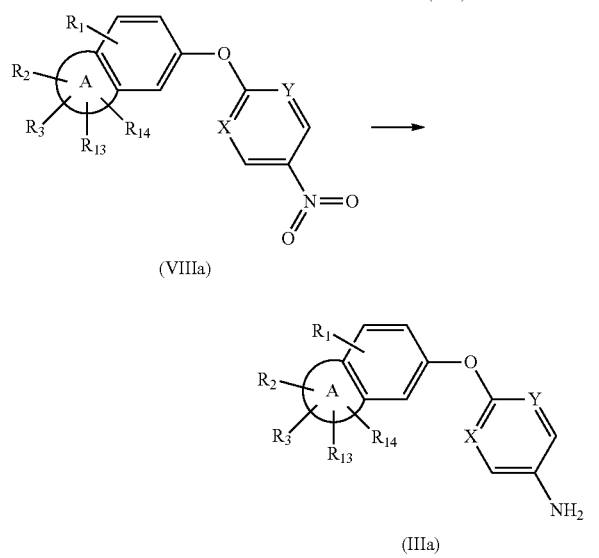

(VIIIa)

(IIIa)

(VIIIc)

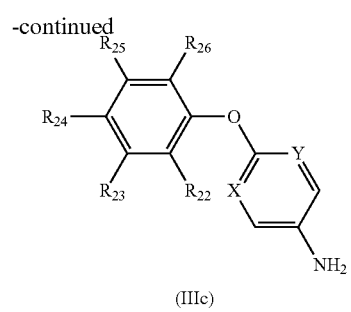

(IIIc)

Anilines of formula (III) can be prepared from the nitro compounds (VIII). Suitable reaction conditions to transform (VIII) into (III) are for example:
- reduction in presence of Fe powder and ammonium chloride in a solvent such as a mixture THF/water for example at room temperature
- reduction with tin chloride hydrate in a solvent such as ethanol with heating for example at reflux
- reduction in presence of Fe powder and hydrochloric acid in a solvent such as a mixture Ethanol/water at temperature ranging from room temperature to reflux.

Scheme 4

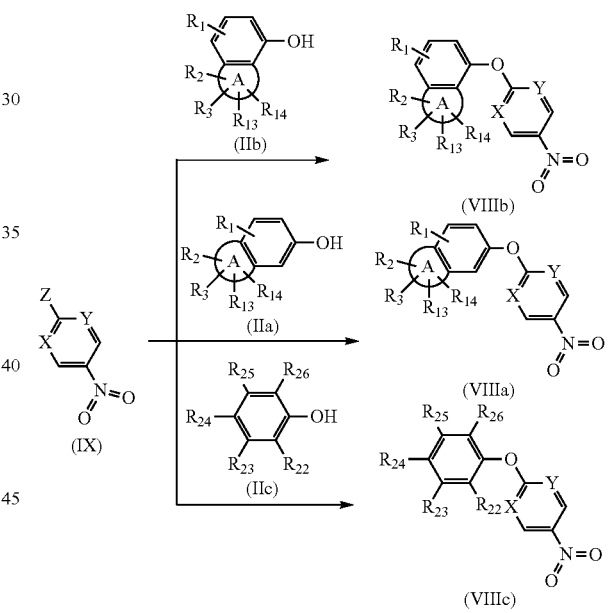

Compounds of formula (VIIIa), (VIIIb) and (VIIIc) can be prepared by nucleophilic aromatic substitution. In this reaction a nitro derivative of formula (IX) wherein Z=F or Cl and a phenol of formula (IIa), (IIb) or (IIc) are used in presence of a base such as potassium carbonate in a solvent e.g. in N,N-dimethylformamide or in acetonitrile with regular heating or microwave heating at a temperature ranging from room temperature to reflux.

Scheme 5

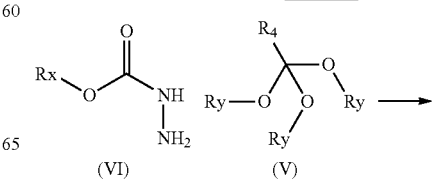

(VI)        (V)

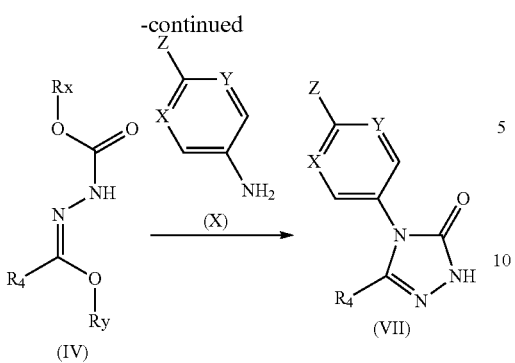

step (ii): Compounds of formula (VII) can be prepared by reaction of anilines of formula (X) with compounds of formula (IV) heating at temperature ranging from 70° C. to 120° C. with regular or microwave heating in a solvent, e.g. methanol or in a solvent free manner. Optionally, in a second stage, a base for example sodium methoxide can be added.

step (i): Compounds of formula (IV) are present as an isomers' mixture (E/Z) and can be prepared as described in Scheme 1.

step (vi): Compound of formula (XVIII) can be prepared from compound of formula (XIX) by a Mitsonobu reaction using triphenylphosine in a solvent such as tetrahydrofuran and adding diisopropyl azodicarboxylate at room temperature.

step (v): Compound of formula (XIX) can be prepared from compound of formula (XX) in a sequential manner
- deprotection in acidic conditions such as HCl 2N in water in ethanol
- evaporation of the solvent and use of a strong base such as NaH in a solvent such as THF at 0° C.
- addition of MOMCl at 0° C.
- reduction with lithium aluminium hydride at 0° C.

step (iv): Compound of formula (XX) can be prepared from compound of formula (XXI) using a Corey-Chaykovsky cyclopropanation reaction carried out at room temperature. To pre-form the dimethyloxosulfonium methylide, trimethylsulfoxonium iodide can be used in presence of a base such as NaH in a solvent such as DMSO, the compound of formula (XXI), (prediluted in DMSO) being added in a second stage.

step (iii): Compound of formula (XXI) can be prepared from compound of formula (XXII) using a Wittig reaction.

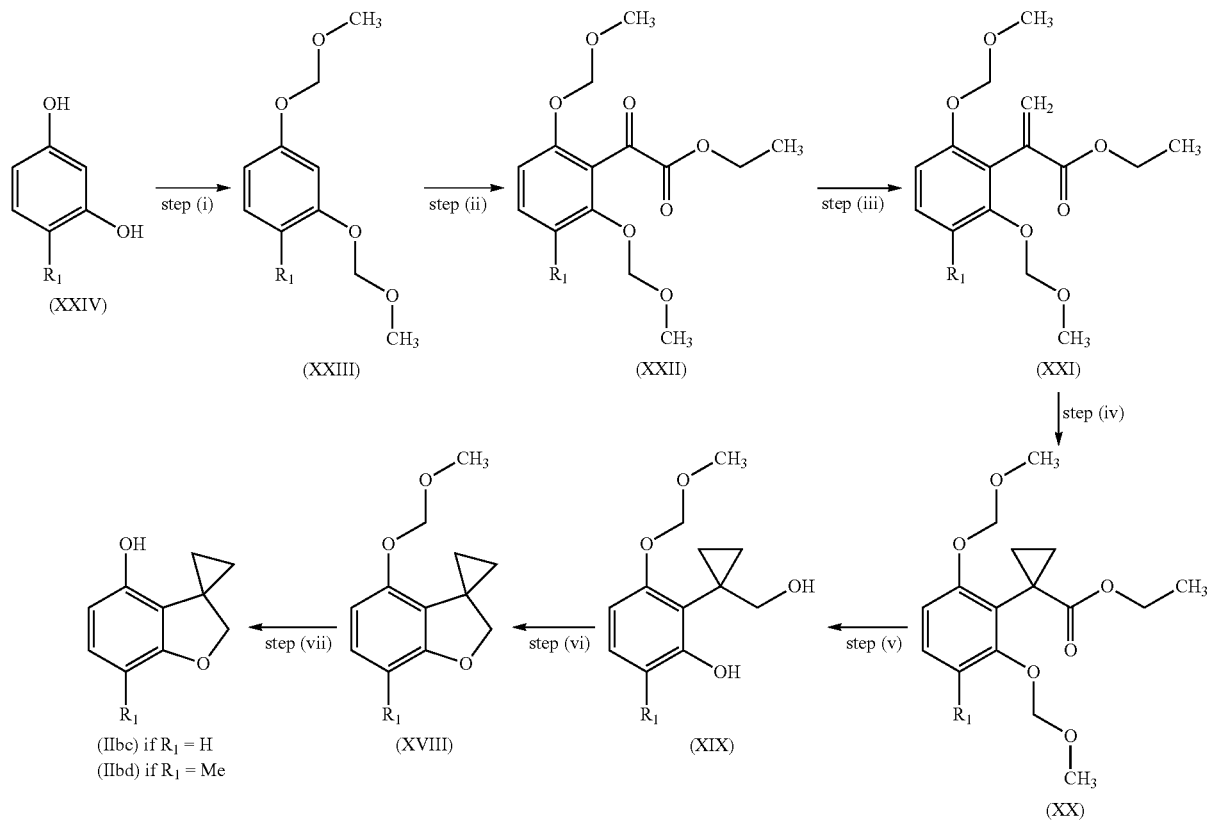

Scheme 6 step (vii): Phenol of formula (IIbc) and (IIbd) corresponding to compound of formula (IIb) wherein $R_1$ is H or methyl can be prepared from compound of formula (XVIII) by removal of the MOM protective group under acidic conditions using for example aqueous HCl in a solvent such as methanol heating e.g. at 50° C.

In order to pre-form the ylide, a phosphonium salt such as methyltriphenylphosphonium bromide and a strong base such as KHMDS can be used in a solvent such as THF from 0° C. to room temperature. The compound of formula (XXII) prediluted in a solvent such as THF can be added in a second stage at 0° C.

step (ii): Compound of formula (XXII) can be prepared from compound (XXIII) by lithiation using BuLi in a solvent such as hexane at room temperature, this solution being added in a second stage at −78° C. to the electrophile e.g. ethyl chloro(oxo)acetate (prediluted e.g. in THF).

step (i): Compound of formula (XXIII) can be prepared from phenol of formula (XXIV) using a base such as NaH and chloro(methyloxy)methane in a solvent such as DMF or THF for example from 0° C. to room temperature.

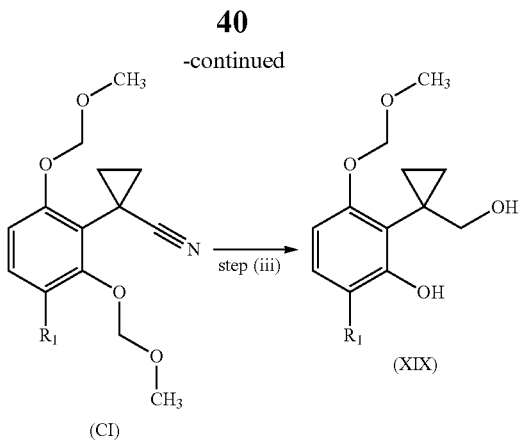

step (iii): Compound of formula (XIX) can alternatively be prepared from a compound of formula (CI) in a sequential manner
- deprotection in acidic conditions such as HCl 2N in water (or HCl in methanol) in a solvent such as ethanol or methanol
- evaporation of the solvent and use of MOMCl and a strong base such as NaH in a solvent such as THF at 0° C.
- reduction with lithium aluminium hydride at 0° C.

step (ii): Compound of formula (CI) can be prepared from a compound of formula (CII) using cyclopropane carbonitrile and a strong base such as KHMDS in toluene at temperature ranging from room temperature to reflux.

step (i): Compound of formula (CII) can be prepared from compound (XXIII) by lithiation using BuLi in a solvent such as hexane or THF at room temperature, this solution being added in a second stage at −10° C. to the electrophile e.g. N-Fluorobenzenesulfonimide (prediluted e.g. in THF).

Scheme 7

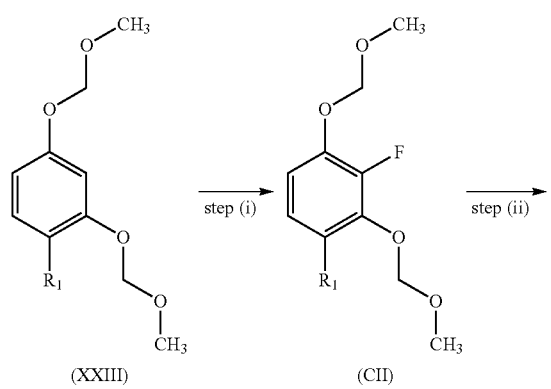

Scheme 8

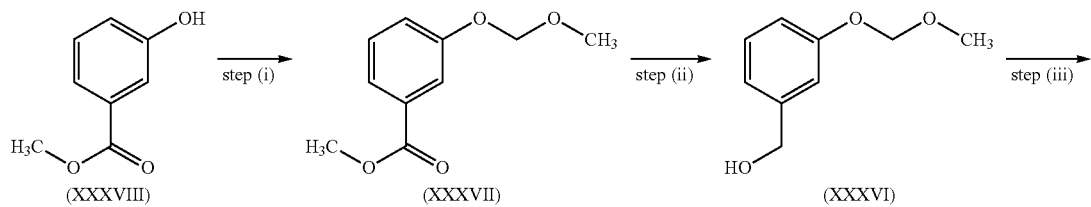

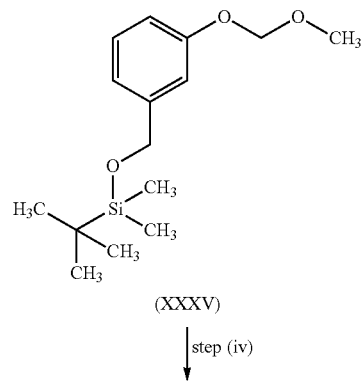

step (iv)

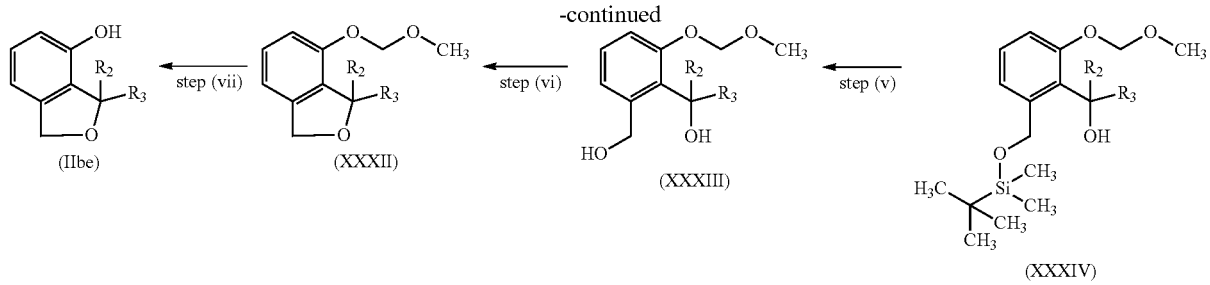

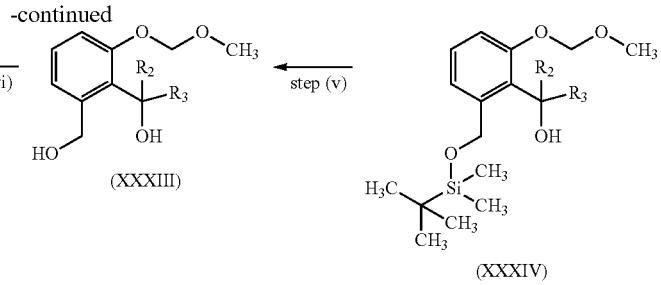

step (vii): Phenol of formula (IIbe) can be prepared from a compound of formula (XXXII) by removal of the MOM protective group under acidic conditions using for example aqueous HCl in a solvent such as methanol heating at a temperature ranging from room temperature to 60° C.

step (vi): Compound of formula (XXXII) can be prepared by cyclization of a compound of formula (XXXIII) using a base such as BuLi in a solvent such as hexane e.g. at 0° C., adding in a second stage 4-methylbenzenesulfonyl chloride e.g. at 0° C., then in a third stage a second equivalent of a base such as nBuLi e.g. at 0° C.

step (v): Compound of formula (XXXIII) can be prepared from a compound of formula (XXXIV) using a desilylating agent such as TBAF in a solvent such as THF at temperature ranging from 0° C. to room temperature.

step (iv): Compound of formula (XXXIV) can be prepared from a compound of formula (XXXV)
- by lithiation using for example nBuLi in a solvent such as hexane at room temperature
- adding in a second stage the appropriate aldehyde or ketone for example at 0° C. and warming up the reaction mixture for example to room temperature.

step (iii): Compound of formula (XXXV) can be prepared from a compound of formula (XXXVI) by silylation, using for example chloro(1,1-dimethylethyl)dimethylsilane, 1H imidazole in a solvent such as dichloromethane at room temperature.

step (ii): Compounds of formula (XXXVI) can be prepared from esters of formula (XXXVII) using a suitable reducing agent typically LiAlH$_4$ in a solvent such as tetrahydrofuran at a temperature such as 0° C.

step (i): Compounds of formula (XXXVII) can be prepared from phenols of formula (XXXVIII) using chloro(methyloxy)methane, a base such as DIPEA in a solvent such as dichloromethane or a base such as sodium hydride in a solvent such as DMF or THF for example from 0° C. to room temperature.

Scheme 9

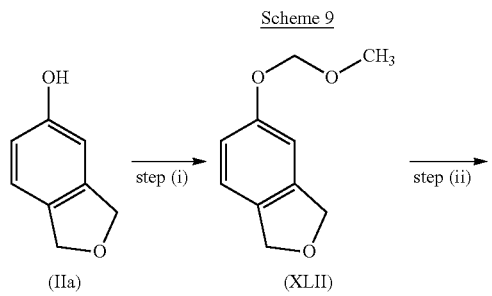

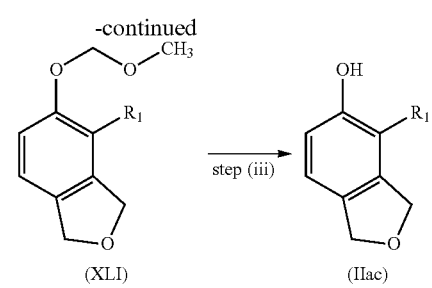

step (iii): Phenols of formula (IIac) can be prepared from compounds of formula (XLI) by cleaving the MOM protecting group with aqueous HCl in a polar solvent such as methanol at temperature ranging from 0° C. to reflux.

step (ii): Compounds of formula (XLI) can be synthesized by deprotonating the ortho-position of compound of formula (XLII) with a base such as butyllithium in a solvent such as THF or diethyl ether at temperature ranging from −78° C. to 0° C. followed by the addition of an appropriate alkylating agent such as R$_1$Cl, R$_1$Br, RdI.

step (i): compound of formula (XLII) can be synthesized by nucleophilic substitution by reacting compound of formula (IIa) with MOMCl in presence of a base in a suitable solvent such as
- triethylamine in DCM; or
- potassium carbonate in DMF or acetonitrile; or
- sodium hydride in DMF or THF.

Scheme 10

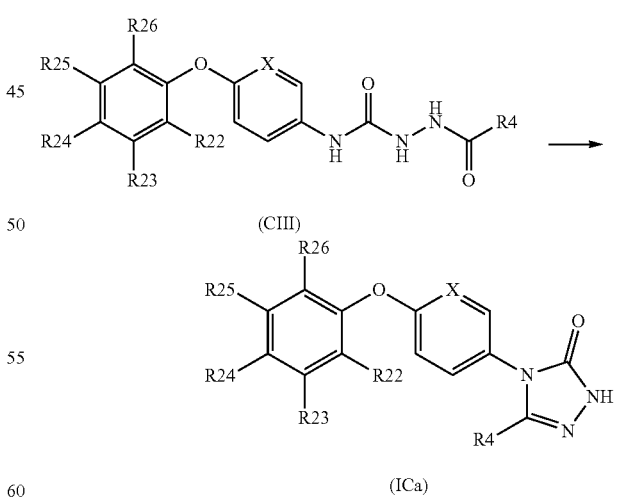

Compounds of formula (ICa) can be prepared by intramolecular condensation of compounds of formula (CIII) in the presence of a base for example aqueous sodium hydroxide, potassium hydroxide, in the presence of a solvent for example water, methanol, heating at high temperature (for example at reflux) with regular heating or microwave irradiation.

Scheme 11

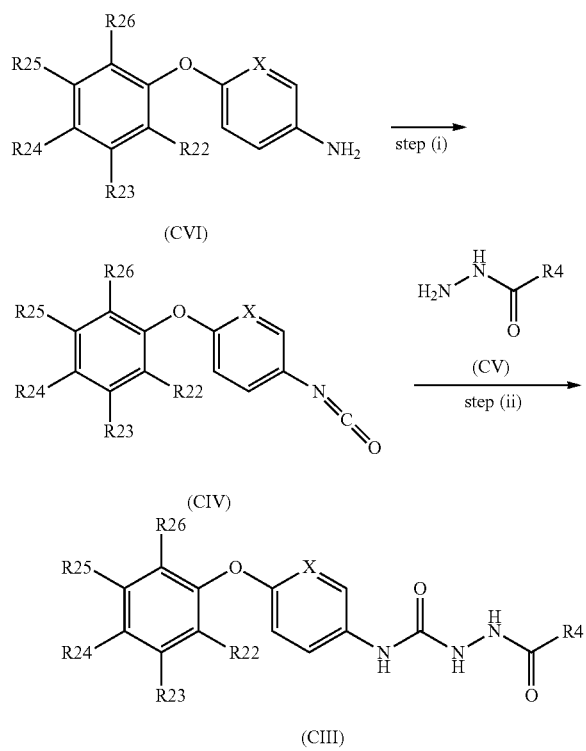

step (ii): Compounds of formula (CIII) can be prepared by reaction of isocyanates of formula (CIV) and hydrazides of formula (CV) in a solvent such as dichloromethane, THF optionally in presence of a base such as triethylamine.

step (i): Isocyanates of formula (CIV) can be prepared from the anilines of formula (CVI) in a solvent such as dichloromethane, with a carbonylating agent such as triphosgene, using a base e.g. triethylamine.

Optionally, the two steps (i) and (ii) can be carried out in a sequential one-pot fashion.

Scheme 12

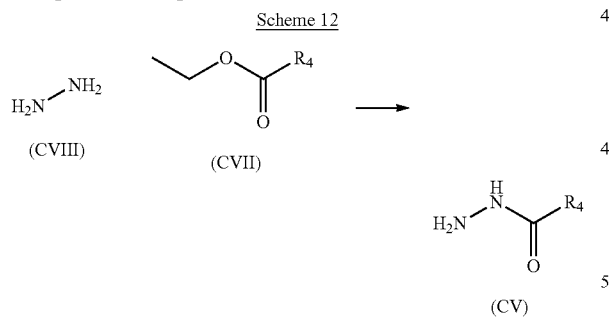

Compounds of formula (CV), corresponding to compounds of formula (CV) wherein $R^4$ is H, methyl can be prepared by reaction of ethyl esters of formula (CVII) with hydrazine (CVIII) in a suitable solvent such as ethanol at room temperature.

Scheme 13

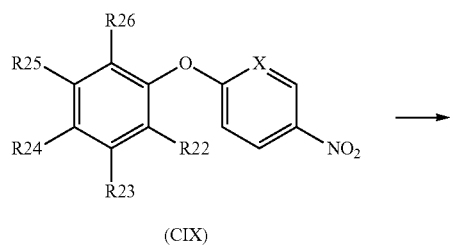

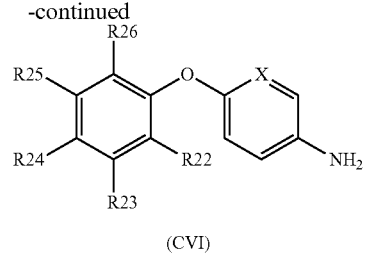

Anilines of formula (CVI) can be prepared from the nitro compounds of formula (CIX). Suitable reactions conditions to transform (CIX) into (CVI) are for example:

- hydrogenation with $H_2$ with a catalyst such as Pd/C or Ni-Raney in a solvent such as methanol, ethanol, THF, a mixture methanol/ethyl acetate with heating or not
- reduction with hydrazine hydrate and a catalytic amount of Pd/C in a solvent such as ethanol with heating
- reduction in presence of Fe powder and ammonium chloride in a solvent such as ethanol or a mixture THF/water with heating or not
- reduction in presence of Zn powder and ammonium chloride in a solvent such as ethanol or a mixture THF/water with heating or not
- reduction with tin chloride hydrate in a solvent such as ethyl acetate, ethanol with heating for example at reflux.

Scheme 14

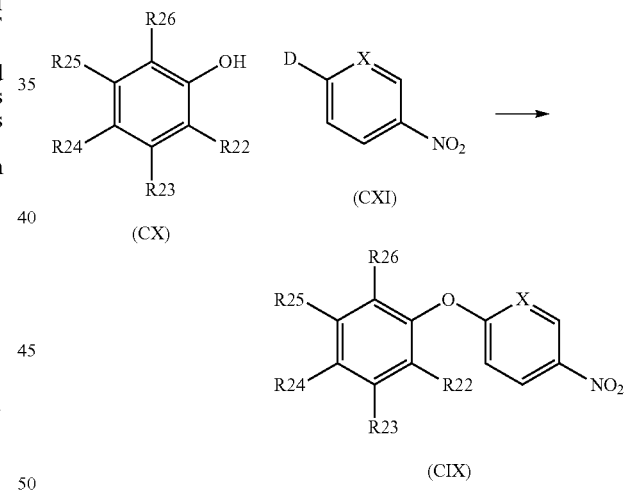

Compounds of formula (CIX) can be prepared by nucleophilic aromatic substitution. In this reaction are used a phenol of formula (CX) and a nitro derivative of formula (X) wherein D is fluoro or chloro in presence of a base in a solvent such as
- potassium carbonate e.g. in N,N-dimethylformamide or in acetonitrile, at temperature ranging from room temperature to reflux
- potassium tertiary-butoxide e.g. in DMSO,
- sodium hydride e.g. in N,N-dimethylformamide with a regular heating e.g. at reflux or with a microwave irradiation. Optionally, before addition of the nitro derivative (CXI), the phenol (CX) can be pre-stirred in presence of the solvent and the base.

Some phenols (CX) are commercially available; other phenols can be prepared with an ad hoc synthesis.

Scheme 15

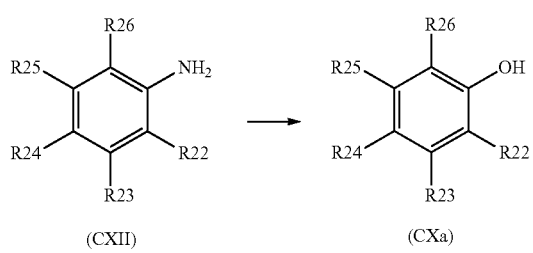

Phenols of formula (CXa), wherein R22-R26 are groups non sensitive to typical nitrosation conditions, can be prepared using the corresponding anilines of formula (CXII) with sodium nitrite in presence of an excess of acid such as sulphuric acid in a solvent such as water, at 0° C. or 0° C.-5° C. in a first time and under heating in a second time.

Scheme 16

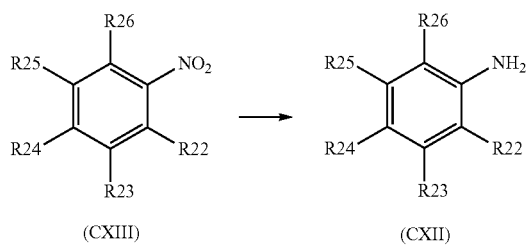

Some anilines of formula (CXII) are commercially available; Other anilines (CXII) can be prepared from the nitro derivatives of formula (CXIII) using reduction conditions for example
- hydrogenation with $H_2$ with a catalyst such as Pd/C or Ni-Raney in a solvent such as methanol, ethanol, THF, a mixture methanol/ethyl acetate with heating or not
- reduction with hydrazine hydrate and a catalytic amount of Pd/C in a solvent such as ethanol with heating
- reduction in presence of Fe powder and ammonium chloride in a solvent such as ethanol or a mixture THF/water with heating or not
- reduction in presence of Zn powder and ammonium chloride in a solvent such as ethanol or a mixture THF/water with heating or not
- reduction with tin chloride hydrate in a solvent such as ethyl acetate, ethanol with heating for example at reflux.

Scheme 17

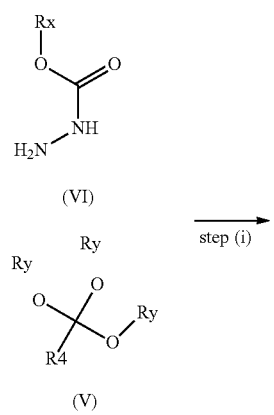

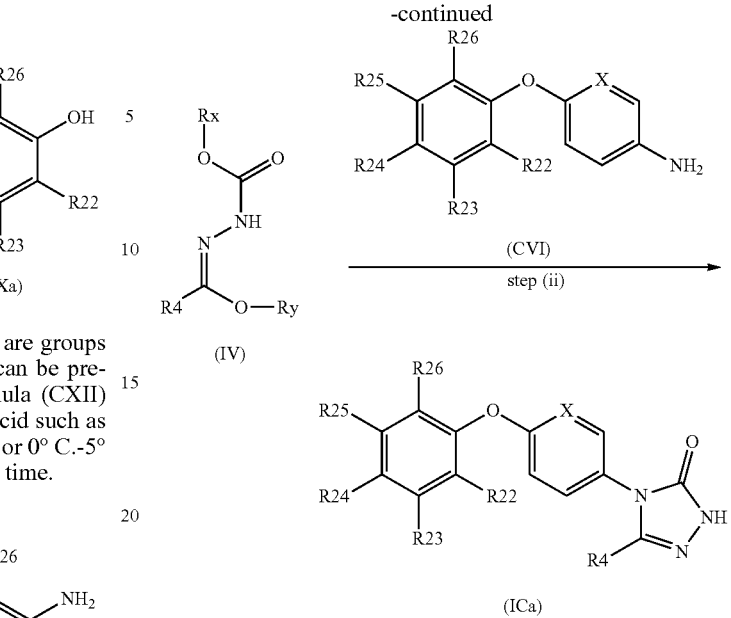

step (ii): Alternatively, compounds of formula (ICa) can be prepared by reaction of anilines of formula (CVI) with compounds of formula (IV) (having Ry=Me or Et and Rx=Me or Et) heating at temperature ranging from 70° C. to 120° C. with a regular or a microwave heating in a solvent, e.g. methanol. Optionally, in a second time, a base for example sodium methoxide can be added.

step (i): Compounds of formula (IV) are present as an isomers' mixture (E/Z) and can be prepared in situ or before by reaction of compounds of formula (V) with alkyl carbazate of formula (VI) in presence of a catalytic amount of p-toluensulfonic acid in a solvent e.g. methanol with heating e.g. at 60° C.

Scheme 18

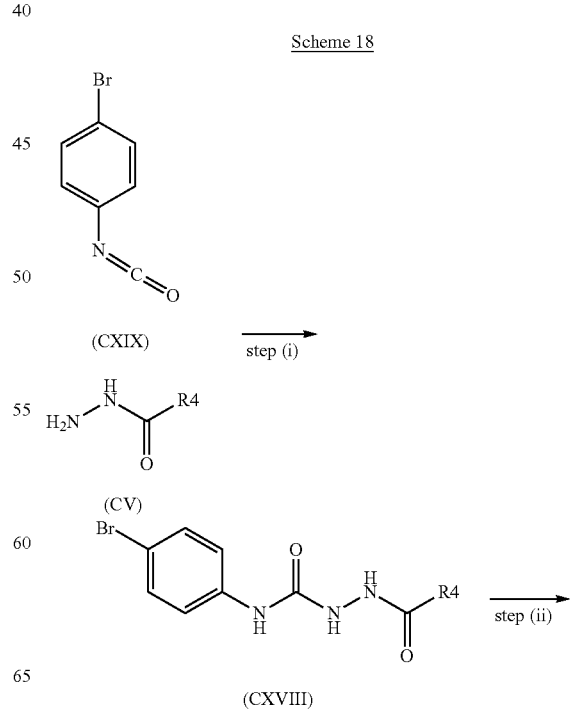

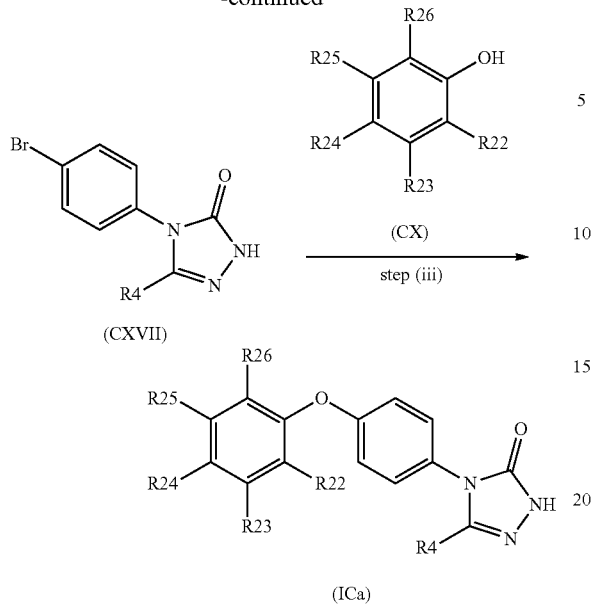

step (iii): Compounds of formula (ICa) can also be prepared from compounds of formula (CXVII) using a coupling reaction with phenols of formula (CX), catalyzed by copper chloride in presence of a base e.g cesium carbonate and of a ligand e.g 2,6,6,tetramethyl-3,5-heptanedione, heating in a high boiling point solvent e.g NMP for example at 120° C.

step (ii): Compound of formula (CXVII) can be prepared by intramolecular condensation of compounds of formula (CXVIII) as described in Scheme 10.

step (i): Compounds of formula (CXVIII) can be prepared by reaction of isocyanates of formula (CXIX) and hydrazides of formula (CV) as described in Scheme 11.

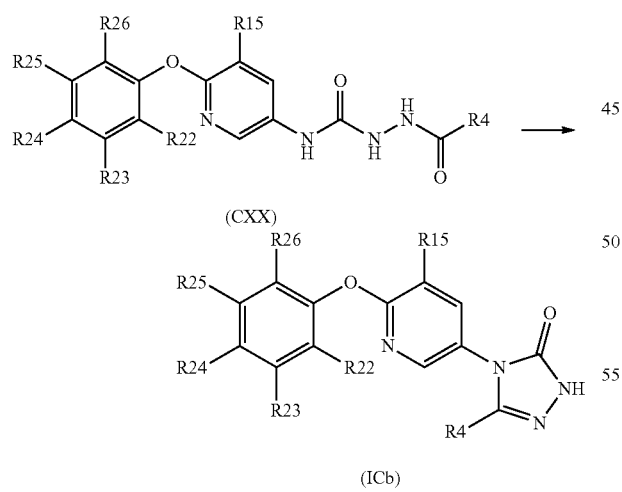

Compounds of formula (ICb) can be prepared by intramolecular condensation of compounds of formula (CXX) in the presence of a base for example aqueous sodium hydroxide, potassium hydroxide, in the presence of a solvent for example water, methanol, heating at high temperature (for example at reflux) with regular heating or microwave irradiation.

step (ii): Compounds of formula (CXX) can be prepared by reaction of isocyanates of formula (CXXI) and hydrazides of formula (CV) in a solvent such as dichloromethane, THF optionally in presence of a base such as triethylamine.

step (i): Isocyanates of formula (CXXI) can be prepared from the anilines of formula (CXXII) in a solvent such as dichloromethane, with a carbonylating agent such as triphosgene, using a base e.g. triethylamine.

Optionally, the two steps (i) and (ii) can be carried out in a sequential one-pot fashion.

Anilines of formula (CXXII) can be prepared from the nitro compounds of formula (CXXIII). Suitable reactions conditions to transform (CXXIII) into (CXXII) are for example:

hydrogenation with $H_2$ with a catalyst such as Pd/C or Ni-Raney in a solvent such as methanol, ethanol, THF, a mixture methanol/ethyl acetate with heating or not reduction with hydrazine hydrate and a catalytic amount of Pd/C in a solvent such as ethanol with heating reduction in presence of Fe powder and ammonium chloride in a solvent such as ethanol or a mixture THF/water with heating or not reduction in presence of Zn powder and ammonium chloride in a solvent such as ethanol or a mixture THF/water with heating or not reduction with tin chloride hydrate in a solvent such as ethyl acetate, ethanol with heating for example at reflux.

Scheme 22

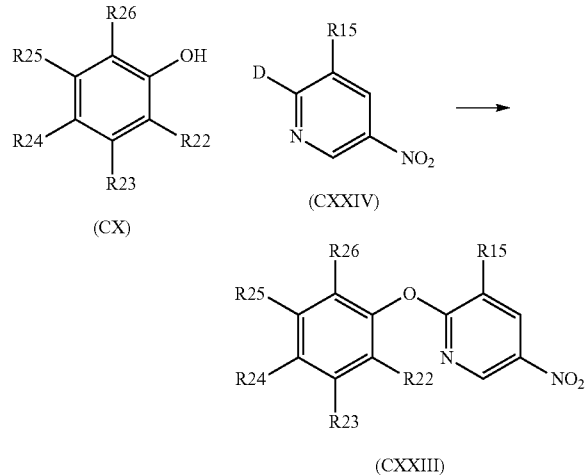

Compounds of formula (VIII) can be prepared by nucleophilic aromatic substitution. In this reaction are used a phenol of formula (CX) and a nitro derivative of formula (CXXIV) wherein D is fluoro or chloro in presence of a base in a solvent such as potassium carbonate e.g. in N,N-dimethylformamide or in acetonitrile, at temperature ranging from room temperature to reflux potassium tertiary-butoxide e.g. in DMSO, sodium hydride e.g. in N,N-dimethylformamide with a regular heating e.g. at reflux or with a microwave irradiation. Optionally, before addition of the nitro derivative (CXXIV), the phenol (CX) can be pre-stirred in presence of the solvent and the base.

Some phenols (CX) are commercially available; other phenols can be prepared with an ad hoc synthesis.

Scheme 23

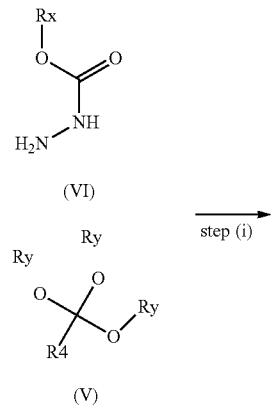

step (ii): Alternatively, compounds of formula (ICb) can be prepared by reaction of anilines of formula (CXXII) with compounds of formula (IV) (having Ry=Me or Et and Rx=Me or Et) heating at temperature ranging from 70° C. to 120° C. with a regular or a microwave heating in a solvent, e.g. methanol. Optionally, in a second time, a base for example sodium methoxide can be added.

step (i): Compounds of formula (IV) are present as an isomers' mixture (E/Z) and can be prepared in situ or before by reaction of compounds of formula (V) with alkyl carbazate of formula (VI) in presence of a catalytic amount of p-toluensulfonic acid in a solvent e.g. methanol with heating e.g. at 60° C.

The present invention provides compounds of formula (I) or a pharmaceutically acceptable salt thereof for use in therapy.

The compounds of formula (I) or their pharmaceutically acceptable salts and/or solvates may be of use for the treatment or prophylaxis of a disease or disorder where a modulator of the Kv3.1 or Kv3.2 or Kv3.1 and Kv3.2 channels is required. As used herein, a modulator of Kv3.1 or Kv3.2 or Kv 3.1 and Kv3.2 is a compound which alters the properties of these channels, either positively or negatively. Compounds of the invention may be tested in the assay of Biological Example 1 to determine their modulatory properties.

In one embodiment of the invention the compounds of formula (I) or their pharmaceutically acceptable salts and/or solvates are selective for modulation of Kv3.1 channels over modulation of Kv3.2 channels. By selective, is meant that compounds demonstrate, for example, at least a 2 fold, 5 fold or 10 fold activity for Kv3.1 channels than for Kv3.2 channels. The activity of a compound is suitably quantified by its potency as indicated by an Ec50 value.

In another embodiment of the invention, the compounds of formula (I) or their pharmaceutically acceptable salts and/or solvates are selective for modulation of Kv3.2 channels over modulation of Kv3.1 channels. Once again, by selective is meant that compounds demonstrate, for example at least a 2 fold, 5 fold or 10 fold activity for Kv3.2 channels than for Kv3.1 channels. Compounds of formula (I) or their pharmaceutically acceptable salts and/or solvates wherein W is Wb and $R_1$ is H may demonstrate greater activity for the Kv3.2 channel over the Kv3.1 channel. Example 15 is a compound of the invention which demonstrates selectivity for Kv3.2 channels.

In a further embodiment of the invention the compounds of formula (I) or their pharmaceutically acceptable salts and/or solvates demonstrate comparable activity between modulation of Kv3.1 and Kv3.2 channels, for example the activity for one channel is less than 2 fold that for the other channel, such as less than 1.5 fold or less than 1.2 fold. Compounds of formula (I) or their pharmaceutically acceptable salts and/or solvates wherein W is Wb $R_1$ is $C_{1-4}$alkyl, in particular methyl, in the para position may demonstrate comparable activity between modulation of Kv3.1 and Kv3.2 channels. Example 14 is a compound of the invention which demonstrates a comparable activity between modulation of Kv3.1 and Kv3.2 channels.

In certain disorders it may be of benefit to utilise a modulator of Kv3.3 or Kv3.1 which demonstrates a particular selectivity profile between the two channels. For example a compound may be selective for modulation of Kv3.3 channels over modulation of Kv3.1 channels demonstrating, for example, at least a 2 fold, 5 fold or 10 fold activity for Kv3.3 channels than for Kv3.1 channels. Alternatively, a compound may be selective for modulation of Kv3.3 channels over modulation of Kv3.2 channels demonstrating, for example, at least a 2 fold, 5 fold or 10 fold activity for Kv3.3 channels than for Kv3.2 channels. In other cases a compound may demonstrate comparable activity between modulation of Kv3.3 and Kv3.1 channels, for example the activity for each channel is less than 2 fold that for the other channel, such as less than 1.5 fold or less than 1.2 fold. In other cases a compound may demonstrate comparable activity between modulation of Kv3.3 and Kv3.2 channels, for example the activity for each channel is less than 2 fold that for the other channel, such as less than 1.5 fold or less than 1.2 fold.

In other cases a compound may demonstrate comparable activity between modulation of Kv3.3, Kv3.2 and Kv3.1 channels, for example the activity for each channel is less than 2 fold that for any other channel, such as less than 1.5 fold or less than 1.2 fold. The activity of a compound is suitably quantified by its potency as indicated by an $EC_{50}$ value.

Compounds of the invention may be tested in the assay of Biological Example 1 to determine their modulatory properties for the Kv3.3 channel.

Diseases or conditions that may be mediated by modulation of Kv3.1 and/or Kv3.2 channels may be selected from the list below. The numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10).

The compounds of formula (I) or their pharmaceutically acceptable salts and/or solvates may be of use for the treatment or prophylaxis of depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90); Seasonal affective disorder.

The compounds of formula (I) or their pharmaceutically acceptable salts and/or solvates (e.g. salts) may be of use for the treatment or prophylaxis of schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

The compounds of formula (I) or their pharmaceutically acceptable salts and/or solvates (e.g. salts) may be of use for the treatment or prophylaxis of anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00).

The compounds of formula (I) or their pharmaceutically acceptable salts and/or solvates (e.g. salts) may be of use for the treatment or prophylaxis of substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

The compounds of formula (I) or their pharmaceutically acceptable salts and/or solvates (e.g. salts) may be of use for the enhancement of cognition including the treatment of cognition impairment in other diseases such as schizophrenia, bipolar disorder, depression, other psychiatric disorders and psychotic conditions associated with cognitive impairment, e.g. Alzheimer's disease. Alternatively, the compounds of formula (I) or their pharmaceutically acceptable salts and/or solvates may be of use for the prophylaxis of cognition impairment, such as may be associated with in diseases such as schizophrenia, bipolar disorder, depression, other psychiatric disorders and psychotic conditions associated with cognitive impairment, e.g. Alzheimer's disease.

The compounds of formula (I) or their pharmaceutically acceptable salts and/or solvates (e.g. salts) may be of use for the treatment or prophylaxis of sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome.

The compounds of formula (I) or their pharmaceutically acceptable salts and/or solvates (e.g. salts) may be of use for the treatment or prophylaxis of eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50).

The compounds of formula (I) or their pharmaceutically acceptable salts and/or solvates (e.g. salts) may be of use for the treatment or prophylaxis of Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

The compounds of formula (I) or their pharmaceutically acceptable salts and/or solvates (e.g. salts) may be of use for the treatment or prophylaxis of Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23).

The compounds of formula (I) or their pharmaceutically acceptable salts and/or solvates (e.g. salts) may be of use for the treatment or prophylaxis of Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9).

The compounds of formula (I) or their pharmaceutically acceptable salts and/or solvates (e.g. salts) may be of use for the treatment or prophylaxis of Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

The compounds of formula (I) or their pharmaceutically acceptable salts and/or solvates (e.g. salts) may be of use for the treatment or prophylaxis of Impulse control disorder including: Intermittent Explosive Disorder (312.34), Kleptomania (312.32), Pathological Gambling (312.31), Pyromania (312.33), Trichotillomania (312.39), Impulse-Control Disorders Not Otherwise Specified (312.3), Binge Eating, Compulsive Buying, Compulsive Sexual Behaviour and Compulsive Hoarding.

The compounds of formula (I) or their pharmaceutically acceptable salts and/or solvates (e.g. salts) may be of use for the treatment or prophylaxis of hearing disorders including auditory neuropathy, auditory processing disorder, hearing loss, which includes sudden hearing loss, noise induced hearing loss, substance-induced hearing loss, and hearing loss in adults over 60 (presbycusis), and tinnitus.

The compounds of formula (I) or their pharmaceutically acceptable salts and/or solvates (e.g. salts) may be of use for the treatment or prophylaxis of Meniere's disease, disorders of balance, and disorders of the inner ear.

The compounds of formula (I) or their pharmaceutically acceptable salts and/or solvates (e.g. salts) may be of use for the treatment or prophylaxis of hyperacusis and disturbances of loudness perception, including Fragile-X syndrome and autism.

The compounds of formula (I) or their pharmaceutically acceptable salts and/or solvates (e.g. salts) may be of use for the treatment or prophylaxis of Epilepsy, (including, but not limited to, localization-related epilepsies, generalized epilepsies, epilepsies with both generalized and local seizures, and the like), seizures associated with Lennox-Gastaut syndrome, seizures as a complication of a disease or condition (such as seizures associated with encephalopathy, phenylketonuria, juvenile Gaucher's disease, Lundborg's progressive myoclonic epilepsy, stroke, head trauma, stress, hormonal changes, drug use or withdrawal, alcohol use or withdrawal, sleep deprivation, fever, infection, and the like), essential tremor, restless limb syndrome, partial and generalised seizures (including tonic, clonic, tonic-clonic, atonic, myoclonic, absence seizures), secondarily generalized seizures, temporal lobe epilepsy, absence epilepsies (including childhood, juvenile, myoclonic, photo- and pattern-induced), severe epileptic encephalopathies (including hypoxia-related and Rasmussen's syndrome), febrile convulsions, epilepsy partialis continua, progressive myoclonus epilepsies (including Unverricht-Lundborg disease and Lafora's disease), post-traumatic seizures/epilepsy including those related to head injury, simple reflex epilepsies (including photosensitive, somatosensory and proprioceptive, audiogenic and vestibular), metabolic disorders commonly associated with epilepsy such as pyridoxine-dependent epilepsy, Menkes' kinky hair disease, Krabbe's disease, epilepsy due to alcohol and drug abuse (e.g. cocaine), cortical malformations associated with epilepsy (e.g. double cortex syndrome or subcortical band heterotopia), chromosomal anomolies associated with seizures or epilepsy such as Partial monosomy (15Q)/Angelman syndrome)

Disease or disorders that may be mediated by modulation of Kv3.3 channels may be selected from:
    ataxia, in particular spinocerebellar ataxia, especially ataxia associated with R420H, R423H or F448L mutations;
    hearing disorders, including tinnitus (as described above).

In one embodiment of the invention, there is provided a compound of formula (I) or a pharmaceutically acceptable salt and/or solvate (e.g. salt) thereof for the treatment or prophylaxis of depression and mood disorders, hearing disorders, schizophrenia, substance abuse disorders, sleep disorders or epilepsy.

In one embodiment of the invention, there is provided a compound of formula (I) or a pharmaceutically acceptable salt and/or solvate (e.g. salt) thereof for the treatment or prophylaxis of spinocerebellar ataxia, including spinocerebellar ataxia associated with R420H, R423H or F448L mutations of the Kv3.3 channel.

In one embodiment of the invention the disorder to be treated results from a R420H mutation of the Kv3.3 channel. In another embodiment of the invention the disorder to be treated results from a R423H mutation of the Kv3.3 channel. In a further embodiment of the invention the disorder to be treated results from a F448L mutation of the Kv3.3 channel.

In one embodiment of the invention, there is provided a compound of formula (I) or a pharmaceutically acceptable salt and/or solvate (e.g. salt) thereof for the treatment or prophylaxis of bipolar disorder or mania.

The term "treatment" or "treating" as used herein includes the control, mitigation, reduction, or modulation of the disease state or its symptoms.

The term "prophylaxis" is used herein to mean preventing symptoms of a disease or disorder in a subject or preventing recurrence of symptoms of a disease or disorder in an afflicted subject and is not limited to complete prevention of an affliction.

The invention also provides a method of treating or preventing a disease or disorder where a modulator of Kv3.1, Kv3.2 or Kv3.3 is required, for example those diseases and disorders mentioned hereinabove, which comprises administering to a subject in need thereof an effective amount of a compound of formula (I) or a pharmaceutically acceptable salt and/or solvate (e.g. salt) thereof.

The invention also provides a compound of formula (I), or a pharmaceutically acceptable salt and/or solvate (e.g. salt) thereof, for use in the treatment or prophylaxis of a disease or disorder where a modulator of Kv3.1, Kv3.2 or Kv3.3 is required, for example those diseases and disorders mentioned hereinabove.

The invention also provides the use of a compound of formula (I), or a pharmaceutically acceptable salt and/or solvate thereof (e.g. salt), in the manufacture of a medicament for the treatment or prophylaxis of a disease or disorder where a modulator of Kv3.1, Kv3.2 or Kv3.3 is required, for example those diseases and disorders mentioned hereinabove.

The invention also provides a method of treating depression and mood disorders, schizophrenia, substance abuse disorders, sleep disorders or epilepsy, for example for those indications mentioned hereinabove, which comprises administering to a subject in need thereof an effective amount of a Kv3.1, Kv3.2 or Kv3.3 modulator or a pharmaceutically acceptable salt and/or solvate (e.g. salt) thereof.

For use in therapy the compounds of the invention are usually administered as a pharmaceutical composition. The invention also provides a pharmaceutical composition comprising a compound of formula (I), or a pharmaceutically acceptable salt and/or solvate (e.g. salt) thereof, and a pharmaceutically acceptable carrier.

The compounds of formula (I) or their pharmaceutically acceptable salts and/or solvates thereof may be administered by any convenient method, e.g. by oral, parenteral, buccal, sublingual, nasal, rectal or transdermal administration, and the pharmaceutical compositions adapted accordingly. Other possible routes of administration include intratympanic and intracochlear.

The compounds of formula (I) or their pharmaceutically acceptable salts and/or solvates thereof which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, *arachis* oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment the composition is in unit dose form such as a tablet, capsule or ampoule.

The composition may contain from 0.1% to 100% by weight, for example from 10 to 60% by weight, of the active material, depending on the method of administration. The composition may contain from 0% to 99% by weight, for example 40% to 90% by weight, of the carrier, depending on the method of administration. The composition may contain from 0.05 mg to 1000 mg, for example from 1.0 mg to 500 mg, of the active material, depending on the method of administration. The composition may contain from 50 mg to 1000 mg, for example from 100 mg to 400 mg of the carrier, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 500 mg, and such unit doses may be administered more than once a day, for example two or three a day. Such therapy may extend for a number of weeks or months.

As described above, acute noise-induced hearing loss may be caused by events such as exposure to loud noise or a blast. In these cases, where it is anticipated that a future event may result in acute noise-induced hearing loss, the compound of formula (I) or a pharmaceutically acceptable salt, solvate and/or derivative thereof may be administered before the event in order to prevent or reduce acute noise-induced hearing loss. The administration of compound (I) or a pharmaceutically acceptable salt, solvate and/or derivative thereof may prevent any acute noise-induced hearing loss, or may reduce the severity of the acute noise-induced hearing loss or may mitigate other symptoms arising from acute noise-induced hearing loss, such as tinnitus.

"Acute hearing loss" is defined as hearing loss which occurs rapidly over a period of hours or days. For example, hearing loss may occur over a period of minutes, hours or days (for example over a period of up to 1 day, such as up to 2 days, 3 days, 4 days, 5 days, 6 days or 7 days). Acute hearing loss will typically be caused by exposure to loud sound or blast. Hearing loss caused by exposure to loud sound or blast is referred to herein as "noise-induced induced hearing loss". "Acute noise induced hearing loss" is therefore hearing loss which occurs rapidly over a period of hours or days caused by exposure to loud sound or blast.

Important symptoms of acute hearing loss include:
1. a shift in the auditory threshold, i.e. an increase in the minimum sound level of a pure tone that can be heard with no other sound present;
2. tinnitus; and
3. degradation in central auditory processing, for example auditory temporal processing and/or speech understanding.

A "loud" noise or blast may be at least 90 dB, for example, at least 100 dB, at least 110 dB, at least 120 dB or at least 130 dB. However, it will be appreciated that the frequency and duration of the noise or blast will also determine whether or not acute noise-induced hearing loss could be anticipated to occur. For example, a noise or blast of lower intensity may still result in acute hearing loss if of sufficient duration. Furthermore, different individuals will have different sensitivity to noise exposure.

In one embodiment, administration of the compound of formula (I) or a pharmaceutically acceptable salt, solvate and/or derivative thereof is initiated before an event which is anticipated to cause noise-induced acute hearing loss. For example, administration of the compound of formula (I) or a pharmaceutically acceptable salt, solvate and/or derivative thereof may be initiated up to 2 weeks in advance, such as up to 1 week, 6 days, 5 days, 4 days, 3 days, 2 days, 24 hours, 12 hours, 6 hours, 5 hours, 4 hours, 3 hours, 2 hours, 1 hour, 30 minutes or up to 15 minutes in advance of an event which is anticipated to cause noise-induced acute hearing loss. The compound of formula (I) or a pharmaceutically acceptable salt, solvate and/or derivative thereof may be administered on multiple occasions before event which is anticipated to cause noise-induced acute hearing loss.

In one embodiment, administration of the compound of formula (I) or a pharmaceutically acceptable salt, solvate and/or derivative thereof is initiated before an event which is anticipated to cause acute noise-induced hearing loss.

Thus, in one embodiment, a compound of formula (I) or a pharmaceutically acceptable salt, solvate and/or derivative thereof is administered in advance of potential exposure to a noise or blast which is anticipated to cause acute noise-induced hearing loss, for preventing or reducing the development of permanent tinnitus.

In another embodiment, a compound of formula (I) or a pharmaceutically acceptable salt, solvate and/or derivative thereof is administered in advance of potential exposure to a noise or blast which is anticipated to cause acute noise-induced hearing loss, for preventing or reducing the development of a permanent shift in auditory thresholds.

In a further embodiment, a compound of formula (I) or a pharmaceutically acceptable salt, solvate and/or derivative thereof is administered in advance of potential exposure to a noise or blast which is anticipated to cause acute noise-induced hearing loss, for preventing or reducing the development of permanently degraded central auditory processing, including for example auditory temporal processing and/or speech understanding.

It will be appreciated that administration in advance may be in circumstances where the subject is considered to be at risk of exposure to a noise or blast which is anticipated to cause acute noise-induced hearing loss and is not limited to those circumstances where such exposure ultimately occurs.

Alternatively, administration of the compound of formula (I) or a pharmaceutically acceptable salt, solvate and/or derivative thereof may be initiated during an event which is anticipated to result in noise-induced acute hearing loss.

In one embodiment, administration of the compound of formula (I) or a pharmaceutically acceptable salt, solvate and/or derivative thereof is initiated during an event which is anticipated to cause noise-induced acute hearing loss. The compound of formula (I) or a pharmaceutically acceptable salt, solvate and/or derivative thereof may be administered on multiple occasions during an event which is anticipated to cause noise-induced acute hearing loss.

Thus, in one embodiment, a compound of formula (I) or a pharmaceutically acceptable salt, solvate and/or derivative thereof is initially administered during a noise or blast which is anticipated to cause acute noise-induced hearing loss, for preventing or reducing the development of permanent tinnitus.

In another embodiment, a compound of formula (I) or a pharmaceutically acceptable salt, solvate and/or derivative thereof is initially administered during a noise or blast which is anticipated to cause acute noise-induced hearing loss, for preventing or reducing the development of a permanent shift in the auditory threshold.

In a further embodiment, a compound of formula (I) or a pharmaceutically acceptable salt, solvate and/or derivative thereof is initially administered during a noise or blast which is anticipated to cause acute noise-induced hearing loss, for preventing or reducing the development of permanently degraded central auditory processing, including for example auditory temporal processing and/or speech understanding.

Alternatively, administration of the compound of formula (I) or a pharmaceutically acceptable salt, solvate and/or derivative thereof may be initiated after an event which is anticipated to result in noise-induced acute hearing loss, whether noise-induced acute hearing loss was observed or not.

In one embodiment, administration of the compound of formula (I) or a pharmaceutically acceptable salt, solvate and/or derivative thereof is initiated after an event which is anticipated to cause acute noise-induced hearing loss.

Thus, in one embodiment, a compound of formula (I) or a pharmaceutically acceptable salt, solvate and/or derivative thereof is initially administered after a noise or blast which is anticipated to cause acute noise-induced hearing loss, for preventing or reducing the development of permanent tinnitus.

In another embodiment, a compound of formula (I) or a pharmaceutically acceptable salt, solvate and/or derivative thereof is initially administered after a noise or blast which is anticipated to cause acute noise-induced hearing loss, for preventing or reducing the development of a permanent shift in the auditory threshold.

In a further embodiment, a compound of formula (I) or a pharmaceutically acceptable salt, solvate and/or derivative thereof is initially administered after a noise or blast which is anticipated to cause acute noise-induced hearing loss, for preventing or reducing the development of permanently degraded central auditory processing, including for example auditory temporal processing and/or speech understanding.

When the compound of formula (I) is administered after an event which is anticipated to cause acute noise-induced hearing loss in order to prevent or reduce the development of tinnitus and/or the development of a permanent shift in the auditory threshold and/or the development of permanently degraded central auditory processing (including for example auditory temporal processing and/or speech understanding), such administration is normally undertaken during the "acute phase" i.e. before the hearing loss has become established.

In one embodiment, administration of the compound of formula (I) or a pharmaceutically acceptable salt, solvate and/or derivative thereof is initiated after an event which is anticipated to cause noise-induced acute hearing loss. For example, administration of the compound of formula (I) or a pharmaceutically acceptable salt, solvate and/or derivative thereof may be initiated up to 2 months after an event, such as up to 1 month, 2 weeks, 1 week, 6 days, 5 days, 4 days, 3 days, 2 days, 24 hours, 12 hours, 6 hours, 5 hours, 4 hours, 3 hours, 2 hours, 1 hour, 30 minutes or up to 15 minutes after an event which is anticipated to cause acute noise-induced hearing loss. In respect of methods intended to prevent or reduce the onset of tinnitus resulting from noise-induced hearing loss administration of the compound of formula (I) or a pharmaceutically acceptable salt, solvate and/or derivative thereof may be initiated up to 6 months after an event, such as up to 2 months, 1 month, 1 week, 6 days, 5 days, 4 days, 3 days, 2 days, 24 hours, 12 hours, 6 hours, 5 hours, 4 hours, 3 hours, 2 hours, 1 hour, 30 minutes or up to 15 minutes after an event which is anticipated to cause noise-induced acute hearing loss. The compound of formula (I) or a pharmaceutically acceptable salt, solvate and/or derivative thereof may be administered on multiple occasions after an event which is anticipated to cause noise-induced acute hearing loss.

Administration of the compound of formula (I) or a pharmaceutically acceptable salt, solvate and/or derivative thereof will be continued for as long as required to achieve the benefit of the invention. Typically, administration will be for a period of at least 1 week, such as at least 2 weeks, 1 month, 2 months, 6 months, 1 year or indefinitely.

The compound of formula (I) or a pharmaceutically acceptable salt, solvate and/or derivative thereof may be administered over a period of up to 7 days (for example, up to 1 day, up to 2 days, up to 3 days, up to 4 days, up to 5 days, up to 6 days or up to 7 days), for 1-2 weeks (for example, 7-8 days, 7-9 days, 7-10 days, 7-11 days, 7-12 days, 7-13 days or 7-14 days), for 2-4 weeks (for example, 2-3 weeks or 2-4 weeks) or for 1-2 months (for example, 4-6 weeks or 4-8 weeks).

The compound of formula (I) or a pharmaceutically acceptable salt, solvate and/or derivative thereof may initially be administered up to 1 day in advance, such as up to 2 days in advance, up to 3 days in advance, up to 5 days in advance, up to 1 week in advance, up to 2 weeks in advance or up to 1 month in advance of a noise or blast which is anticipated to cause acute noise-induced hearing loss, administration which is initiated at any point in advance exposure to a noise or blast which is anticipated to cause acute noise-induced hearing loss will typically continue for up to 2 months after exposure to the noise or blast which is anticipated to cause acute noise-induced hearing loss, such as for up to 1 month after, up to 3 weeks after, up to two weeks after, up to 1 week after, up to 5 days after, up to 3 days after, up to 2 days after, or up to 1 day after.

Administration which is initiated during exposure to a noise or blast which is anticipated to cause acute noise-induced hearing loss will typically continue for up to 2 months after exposure to the noise or blast which is anticipated to cause acute noise-induced hearing loss, such as for up to 1 month after, up to 3 weeks after, up to two weeks after, up to 1 week after, up to 5 days after, up to 3 days after, up to 2 days after, or up to 1 day after. The compound of formula (I) or a pharmaceutically acceptable salt, solvate and/or derivative thereof may be initiated up to 2 weeks after an event, such as up to 1 week, 6 days, 5 days, 4 days, 3 days, 2 days, 24 hours, 12 hours, 6 hours, 5 hours, 4 hours, 3 hours, 2 hours, 1 hour, 30 minutes or up to 15 minutes after the noise or blast which is anticipated to cause acute noise-induced hearing loss, administration which is initiated after exposure to a noise or blast which is anticipated to cause acute noise-induced hearing loss will typically continue for up to 2 months after exposure to the noise or blast which is anticipated to cause acute noise-induced hearing loss, such as for up to 1 month after, up to 3 weeks after, up to two weeks after, up to 1 week after, up to 5 days after, up to 3 days after, up to 2 days after, or up to 1 day after.

The ability of a compound of formula (I) or a pharmaceutically acceptable salt, solvate and/or derivative thereof to prevent permanent noise induced hearing loss may be quantified at a reasonable time period after the exposure to the noise or blast which is anticipated to cause acute noise-induced hearing loss using appropriate testing methodologies known to the skilled person. For example, it is suitably quantified 2 weeks to 2 months after the exposure to the noise or blast which is anticipated to cause acute noise-induced hearing loss, for example about 4 weeks after the exposure to the noise or blast which is anticipated to cause acute noise-induced hearing loss.

Suitably, quantifying permanent noise induced hearing loss is undertaken at least one week after administration of the a compound of formula (I) or a pharmaceutically acceptable salt, solvate and/or derivative thereof has been ceased, such as at least two weeks after, for example 2-4 weeks after, or at least one month after, for example one to two months after. The ability of a compound of formula (I) or a pharmaceutically acceptable salt, solvate and/or derivative thereof to reduce the development of a of a permanent shift in the auditory threshold is suitably quantified by method similar to those provided in Biological Example 2, such as measurement of hearing thresholds for pure tones at one or more frequencies between 500 Hz and 12 kHz.

Thus, in one embodiment is provided a compound of formula (I) or a pharmaceutically acceptable salt, solvate and/or derivative thereof for use in preventing or reducing the development of a permanent shift in the auditory threshold, wherein the permanent shift in auditory threshold is reduced by at least 10 dB, such as at least 15 dB, at least 20 dB, at least 30 dB, at least 40 dB, or completely.

The ability of a compound of formula (I) or a pharmaceutically acceptable salt, solvate and/or derivative thereof to reduce the development of permanent tinnitus is suitably quantified using, for example, the Tinnitus Handicap Inventory (Arch Otolaryngol Head Neck Surg. 1996 February; 122(2):143-8 and Development of the Tinnitus Handicap Inventory; Newman C W, Jacobson G P, Spitzer J B) and/or the Tinnitus Functional Index (Meikle et al. Ear Hear. 2012 March-April; 33(2):153-76. doi: 10.1097/AUD.0b013e31822f67c0) and/or assessment of minimum masking level (e.g. Jastreboff et al. Hear Res. 1994 November; 80(2):216-32).

Thus, in one embodiment is provided a compound of formula (I) or a pharmaceutically acceptable salt, solvate and/or derivative thereof for use in preventing or reducing the development of permanent tinnitus, wherein the permanent tinnitus is reduced by at least 10 points on the Tinnitus Handicap Inventory, and/or at least 10 points on the Tinnitus Functional Index, and/or at least 5 dB in minimum masking level. One method for evaluating whether tinnitus is experienced as a symptom may be of acute noise-induced hearing loss may be a gap detection model, such as provided in the examples.

The ability of a compound of formula (I) or a pharmaceutically acceptable salt, solvate and/or derivative thereof to reduce the development of permanently degraded central auditory processing is suitably quantified using a speech-in-noise test such as the Hearing In Noise Test (Nilsson et al., J Acoust Soc Am. 1994 February; 95(2):1085-99). An alternative method to quantify the development of central auditory processing deficits is a gap detection model, such as provided in the examples.

Thus, in one embodiment is provided a compound of formula (I) or a pharmaceutically acceptable salt, solvate and/or derivative thereof for use in preventing or reducing the development of permanently degraded central auditory processing (including for example auditory temporal processing and/or speech understanding), wherein the permanently degraded central auditory processing as measured using the Hearing In Noise Test is reduced by at least 2 dB.

The invention provides, in a further aspect, a combination comprising a compound of formula (I) or a pharmaceutically acceptable, salt, solvate and/or derivative thereof (e.g. a combination comprising a compound of formula (I) or a pharmaceutically acceptable derivative thereof) together with a further therapeutic agent or agents.

The invention provides a compound of formula (I), for use in combination with a further therapeutic agent or agents.

When the compounds are used in combination with other therapeutic agents, the compounds may be administered either sequentially or simultaneously by any convenient route. Alternatively, the compounds may be administered separately.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations. The individual components of combinations may also be administered separately, through the same or different routes.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

The present invention also provides Kv3 modulators, or their pharmaceutically acceptable salts and/or solvates (e.g. salts) thereof, for use in the treatment or prophylaxis of depression and mood disorders, hearing disorders, schizophrenia, substance abuse disorders, sleep disorders or epilepsy.

The present invention also provides Kv3.3 modulators or their pharmaceutically acceptable salts and/or solvates thereof (e.g. salts), for use in the treatment or prophylaxis of spinocerebellar ataxia.

In particular Kv3 modulators or their pharmaceutically acceptable salts and/or solvates (e.g. salts) may be particularly useful in the treatment or prophylaxis of depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90), Seasonal affective disorder.

The invention also provides a method of treating depression and mood disorders, hearing disorders, schizophrenia, substance abuse disorders, sleep disorders or epilepsy, including for example those disorders mentioned hereinabove, which comprises administering to a subject in need thereof an effective amount of Kv3 modulator or a pharmaceutically acceptable salt and/or solvate (e.g. salt) thereof.

The invention also provides a method for the treatment or prophylaxis of spinocerebellar ataxia, which comprises administering to a subject in need thereof an effective amount of Kv3.3 modulator or a pharmaceutically acceptable salt and/or solvate (e.g. salt) thereof.

The invention also provides a Kv3 modulator, or a pharmaceutically acceptable salt and/or solvate (e.g. salt) thereof, for use in the treatment or prophylaxis of depression and mood disorders, hearing disorders, schizophrenia, substance abuse disorders, sleep disorders or epilepsy, including for example those disorders mentioned hereinabove.

The invention also provides the use of a Kv3 modulator, or a pharmaceutically acceptable salt and/or solvate (e.g. salt) thereof, in the manufacture of a medicament for the treatment or prophylaxis of depression and mood disorders, hearing disorders, schizophrenia, substance abuse disorders, sleep disorders or epilepsy, including for example those disorders mentioned hereinabove.

The invention also provides the use of a Kv3.3 modulator, or a pharmaceutically acceptable salt and/or solvate (e.g. salt) thereof, in the manufacture of a medicament for the treatment or prophylaxis of spinocerebellar ataxia.

For use in therapy the Kv3 modulators are usually administered as a pharmaceutical composition for example a composition comprising a Kv3 modulator or a pharmaceutically acceptable salt and/or solvate (e.g. salt) thereof, and a pharmaceutically acceptable carrier. Examples of such compositions, and methods of administration thereof, which compositions comprise a compound of formula (I) or a pharmaceutically acceptable salt thereof, are described hereinabove. Such compositions and methods of administration may also be used for other Kv3 modulators or pharmaceutically acceptable salts and/or solvates thereof (e.g. salts), in the treatment of depression and mood disorders, hearing disorders, schizophrenia, substance abuse disorders, sleep disorders or epilepsy, including for example those disorders mentioned hereinabove. Such compositions and methods of administration may also be used for Kv3.3 modulators or pharmaceutically acceptable salts and/or solvates (e.g. salts) thereof, in the treatment of spinocerebellar ataxia.

Furthermore, the invention relates to a method for manufacturing compounds of formula (I), to novel intermediates of use in the manufacture of compounds of formula (I) and to the manufacture of such intermediates.

Particular intermediates of interest include intermediates of formula (VII):

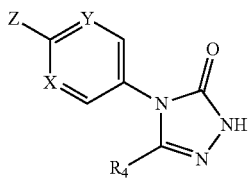

(VII)

wherein:
Z is F, Cl, Br or I;
X is CH or N;
Y is CR$_{15}$ or N;
R$_{15}$ is H or C$_{1-4}$alkyl; and
R$_4$ is H or C$_{1-4}$ alkyl.

Specifically mentioned embodiments for each of groups X, Y, R$_{15}$ and R$_4$ as described above in respect of the compounds of the invention apply equally to formula (VII). Suitably R$_{15}$ is C$_{1-4}$alkyl. Alternatively, R$_4$ is C$_{1-4}$alkyl and at least one of X or Y is N.

Suitably the compounds of formula (VII) do not include those wherein: R$_4$ is H, X is CH and Y is CH, or R$_4$ is methyl, X is CH, Y is CH and Z is Br, or R$_4$ is H, X is CH, Y is N and Z is Cl.

Other intermediates of interest are the phenols:

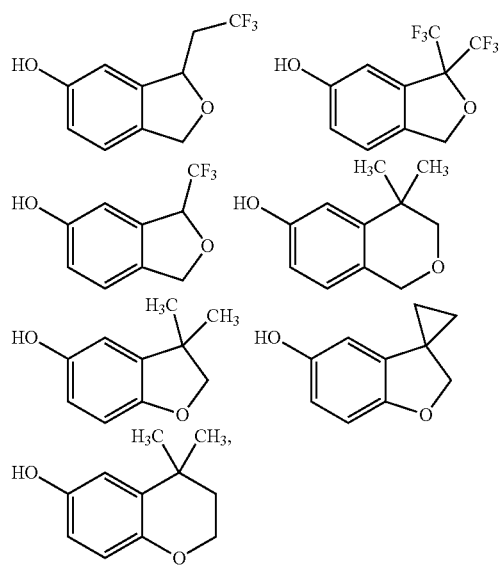

in particular the phenols

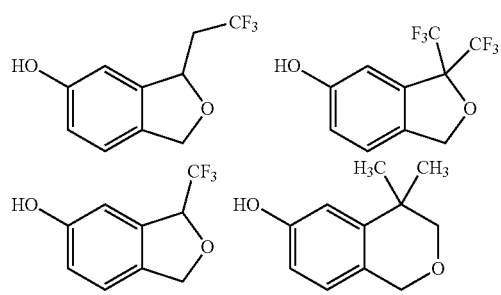

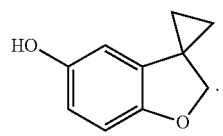

Also the phenols:

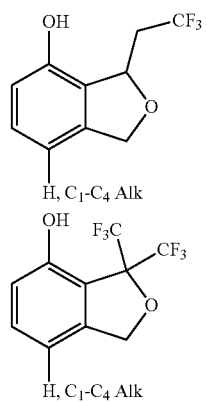
H, C$_1$-C$_4$ Alk

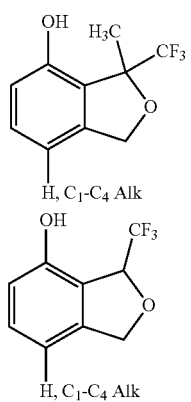
H, C$_1$-C$_4$ Alk

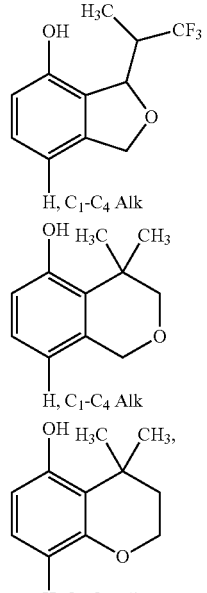
H, C$_1$-C$_4$ Alk in particular

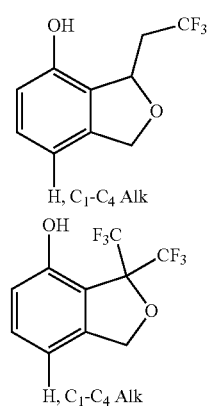
H, C$_1$-C$_4$ Alk

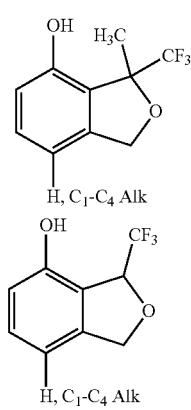
H, C$_1$-C$_4$ Alk

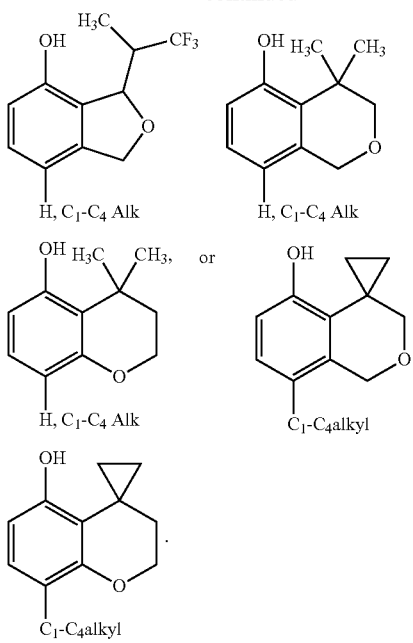

Further, the phenols:

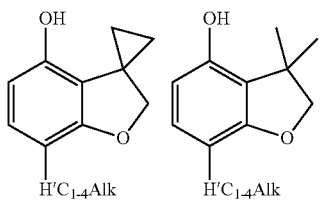

The process of Scheme 6 is described in the prior art. Scheme 7 provides a surprisingly advantageous approach to the preparation of compounds of formula (XIX) which may provide the benefits of a smaller number of process steps, intermediate products which are more easily purified and a more robust process with reproducabile yields. Consequently, the present invention provides a method for the preparation of a compound of formula (CI)

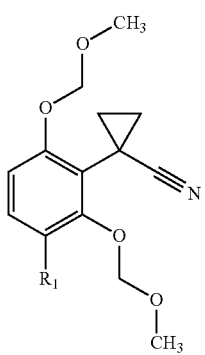

said method comprising reacting the compound of formula (CII):

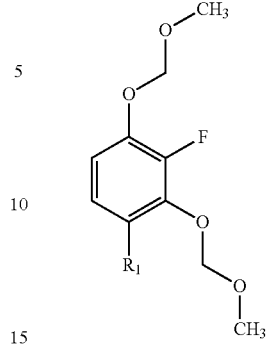

with cyclopropane carbonitrile under appropriate conditions, such as in the presence of a strong base (for example KHMDS) and a suitable solvent (for example toluene) at a temperature from 20° C. to reflux.

The present invention also provides a method for the preparation of a compound of formula (XIX):

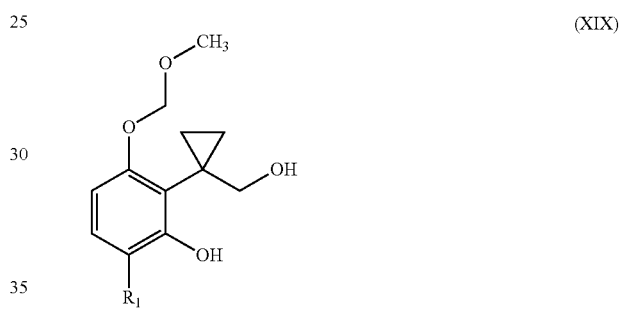

said method comprising modifying a compound of formula (CI):

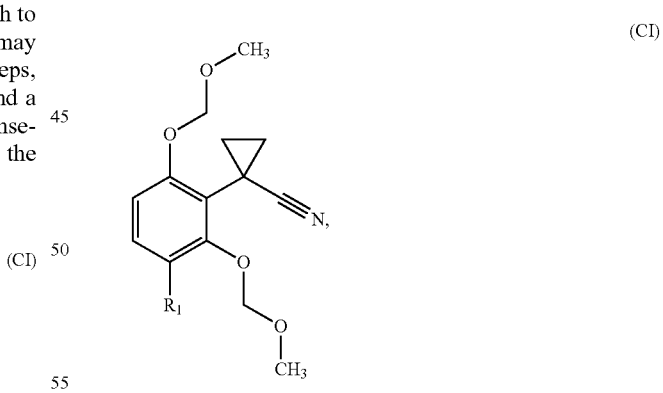

such as by:
(i) deprotection and cyclisation into a lactone, such as under acidic conditions, for example HCl 2N in water (or HCl in methanol) in a solvent such as ethanol or methanol;
(ii) reprotection of the resulting hydroxyl group, such as using MOMCl and a strong base such as NaH in a solvent such as THF at reduced temperature (e.g. 0° C.)
(iii) reduction of the lactone ring, for example using lithium aluminium hydride at at reduced temperature (e.g. 0° C.).

EXPERIMENTAL

The invention is illustrated by the Compounds described below. The following examples describe the laboratory synthesis of specific compounds of the invention and are not meant to limit the scope of the invention in any way with respect to compounds or processes. It is understood that, although specific reagents, solvents, temperatures and time periods are used, there are many possible equivalent alternatives that can be used to produce similar results. This invention is meant to include such equivalents.

Analytical Equipment

Starting materials, reagents and solvents were obtained from commercial suppliers and used without further purification unless otherwise stated. Unless otherwise stated, all compounds with chiral centres are racemic. Where reactions are described as having been carried out in a similar manner to earlier, more completely described reactions, the general reaction conditions used were essentially the same. Work up conditions used were of the types standard in the art, but may have been adapted from one reaction to another. The starting material may not necessarily have been prepared from the batch referred to. Compounds synthesised may have various purities, ranging from for example 85% to 99%. Calculations of number of moles and yield are in some cases adjusted for this.

Proton Magnetic Resonance (NMR) spectra were recorded either on Varian instruments at 300, 400, 500 or 600 MHz, or on Bruker instruments at 400 MHz. Chemical shifts are reported in ppm (δ) using the residual solvent line as internal standard. Splitting patterns are designed as s (singlet), br.s (broad singlet), d (doublet), t (triplet), q (quartet), dd (doublet of doublets), dt (doublet of triplets) and m (multiplet). The NMR spectra were recorded at temperatures ranging from 25 to 60° C.

Direct infusion Mass spectra (MS) were run on an Agilent 1100 Series LC/MSD Mass Spectrometer, operating in ES (+) and ES (−) ionization mode [ES (+): Mass range: 100-1000 amu. Infusion solvent: water+0.1% HCO2H/CH3CN 50/50. ES (−): Mass range: 100-1000 amu. Infusion solvent: water+0.05% NH$_4$OH/CH3CN 50/50]. The use of this methodology is indicated by "MS_1 (ESI)" in the analytic characterization of the described compounds. HPLC-Mass spectra (HPLC-MS) were taken on an Agilent 1100 Series LC/MSD Mass Spectrometer coupled with HPLC instrument Agilent 1100 Series, operating in positive electrospray ionization mode and in acidic gradient conditions.

Quality Control (8 Minutes Method):

LC/MS-ES+ under acidic conditions was performed on a Phenomenex Luna C18 column (3 m 2×50 mm). Mobile phase: A: (H2O+0.05% TFA by vol.)/B: (CH3CN+0.05% TFA by vol). Gradient: t=0 min 0% (B). From 0 to 95% (B) in 8 min. 95% (B) for 0.5 min. From 95 to 100% (B) in 0.5 min. 100% (B) for 0.5 min. From 100% to 0% (B) in 0.1 min. Stop time 11 min. Column T=40° C. Flow rate: 1.0 ml/min. Mass range ES+: (100-1000 amu, F=60). UV detection wavelengths: DAD 1A=220.8, DAD 1B=254.8. The use of this methodology is indicated by "LC/MS: QC_8 MIN" in the analytic characterization of the described compounds.

Quality Control (3 Minutes Method):

LC/MS-ES+ under acidic conditions was performed on a Zorbax SB C18 column (1.8 m 3×50 mm). Mobile phase: A: (H2O+0.05% TFA by vol.)/B: (CH3CN+0.05% TFA by vol). Gradient: t=0 min 0% (B), from 0 to 95% (B) in 2.5 min, 95% (B) for 0.2 min, from 95 to 100% (B) in 0.2 min, 100% (B) for 0.4 min, From 100% to 0% (B) in 0.1 min. Stop time 4 min. Column T=60° C. Flow rate: 1.5 ml/min. Mass range ES+: (100-1000 amu, F=60). UV detection wavelengths: DAD 1A=220.8, DAD 1B=254.8. The use of this methodology is indicated by "LC/MS: QC_3_MIN" in the analytic characterization of the described compounds.

Ultra Performance Liquid Chromatography with an Acidic Gradient:

Total ion current (TIC) and DAD UV chromatographic traces together with MS and UV spectra associated with the peaks were taken on a UPLC/MS Acquity™ system equipped with 2996 PDA detector and coupled to a Waters Micromass ZQ™ mass spectrometer operating in positive or negative electrospray ionisation mode [LC/MS–ES (+ or −): analyses were performed using an Acquity™ UPLC BEH C18 column (50×2.1 mm, 1.7 m particle size). General Method: Mobile phase: A: (water+0.1% HCO2H)/B: (CH3CN+0.06% HCO2H). Gradient: t=0 min 3% (B), t=0.05 min 6% (B), t=0.57 min 70% (B), t=1.06 min 99% (B) lasting for 0.389 min, t=1.45 min 3% (B), stop time 1.5 min. Column T=40° C. Flow rate=1.0 mL/min. Mass range: ES (+): 100-1000 amu. ES (−): 100-800 amu. UV detection range: 210-350 nm. The use of this methodology is indicated by "UPLC_A" in the analytic characterization of the described compounds.

Ultra Performance Liquid Chromatography with a Basic Gradient:

Total ion current (TIC) and DAD UV chromatographic traces together with MS and UV spectra associated with the peaks were taken on a UPLC/MS Acquity™ system equipped with PDA detector and coupled to a Waters SQD mass spectrometer operating in positive and negative alternate electrospray ionisation mode [LC/MS–ES+/−: analyses were performed using an Acquity™ UPLC BEH C18 column (50×2.1 mm, 1.7 m particle size). Mobile phase: A: (10 mM aqueous solution of NH4HCO3 (adjusted to pH 10 with ammonia))/B: CH3CN. Gradient: t=0 min 3% (B), t=1.06 min 99% (B) lasting for 0.39 min, t=1.46 min 3% (B), stop time 1.5 min. Column T=40° C. Flow rate=1.0 mL/min. Mass range: ES (+): 100-1000 amu. ES (−): 100-1000 amu. UV detection range: 220-350 nm. The use of this methodology is indicated by "UPLC_B" in the analytic characterization of the described compounds.

In a number of preparations, purification was performed using manual flash chromatography, semi automatic flash chromatography (Biotage Flash Master Personal) or automatic flash chromatography (Biotage SP1 and SP4).

Flash chromatographies on silica gel were carried out on pre-packed Biotage silica cartridges (e.g. Biotage SNAP cartridge KP-Sil). Reverse phase C18 Flash Chromatographies were carried out using VARIAN MEGA BE-C18 cartridges, or pre-packed Biotage C18 cartridges (e.g. Biotage SNAP cartridge KP-C18-HS).

Abbreviations
BuLi Butyllithium
CDCl$_3$ deutrated chloroform
cHex cyclohexane
CV column volume
DCM dichloromethane
DIPEA N,N-diisopropylethylamine
DIAD Diisopropylazodicarboxylate
DMF N,N-dimethylformamide
DMSO dimethylsulfoxide
DMSO-d$_6$ deutrated dimethylsulfoxide
Et$_2$O diethyl ether
EtOAc ethyl acetate
Fe Iron
h hours H₂ gaseous hydrogen
HCl hydrogen chloride
H₂SO₄ sulfuric acid
K₂CO₃ potassium carbonate
KHDMS potassium hexamethyldisilazide
KOH potassium hydroxide
LiAlH₄ Lithium aluminum hydride
MeCN/CH₃CN acetonitrile
MeOH methanol
MeOD deutrated methanol
MDAP mass-directed autopurification
MgSO₄ magnesium sulfate
MOM methoxymethyl
MOMCl chloromethyl methyl ether
N₂ gaseous nitrogen
NaHCO₃ sodium hydrogenocarbonate
Na₂CO₃ sodium carbonate
NaH sodium hydride
Na₂SO₄ sodium sulfate
Na₂S₂O₃ sodium thiosulfate
NaOH sodium hydroxide
NaCl sodium chloride
NBS N-Bromosuccinimide
NMP N-methyl-2-pyrrolidone
NMR Nuclear Magnetic Resonance
Pd/C palladium on charcoal
PE petroleum ether
POCl₃ phosphoryl chloride
r.t. room temperature
tBuOK potassium tert-butoxide
TBAF tetrabutylammonium fluoride
TBDMS tert-Butyldimethylsilyl
TEA triethylamine
TFA trifluoroacetic acid
THF tetrahydrofuran
TiPS Triisopropylsilyl
TsOH 4-methylbenzenesulfonic acid, p-toluenesulfonic acid
Zn Zinc Intermediate 1

Phenyl {6-[(3,3,7-trimethyl-2,3-dihydro-1-benzo-furan-4-yl)oxy]-3-pyridinyl}carbamate

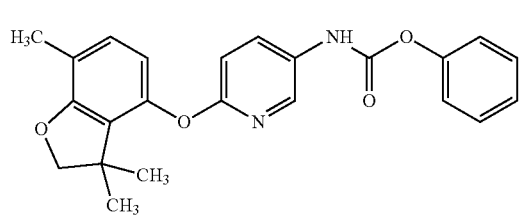 [SMILES: Cc1ccc(Oc2ccc(NC(=O)Oc3ccccc3)cn2)c2c1OCC2(C)C]

6-{[3,3,7-trimethyl-6-(trifluoromethoxy)-2,3-dihydro-1-benzofuran-4-yl]oxy}pyridin-3-amine (WO2012/076877 Intermediate 186, 405 mg, 1.14 mmol) was dissolved in DCM (4 mL). Pyridine (2.28 mmol) and a solution of phenyl chloroformate (1.14 mmol) in DCM (2 mL) was added dropwise. At the end of addition complete conversion was obtained. The mixture was diluted with DCM and treated with an aqueous saturated solution of ammonium chloride. Two phases were separated and the organic layer was washed with brine, dried over Na₂SO₄ and evaporated to dryness to afford the title compound as crude material.

¹H-NMR (400 MHz, DMSO-d₆): δ ppm 10.33 (br. s, 1H), 8.26 (d, 1H, J=2.20 Hz), 7.95 (dd, 1H, J=8.78, 2.64 Hz), 7.46-7.38 (m, 2H), 7.28-7.22 (m, 3H), 6.99 (d, 1H, J=8.78 Hz), 6.94 (d, 1H, J=8.34 Hz), 6.39 (d, 1H, J=8.34 Hz), 4.19 (s, 2H), 2.12 (s, 2H), 1.25 (s, 6H); UPLC_A: 1.27 min, 391.20 [M+H]+, 389.28 [M−H]−.

Intermediate 2

N-{6-[(3,3,7-trimethyl-2,3-dihydro-1-benzofuran-4-yl)oxy]-3-pyridinyl}hydrazinecarboxamide

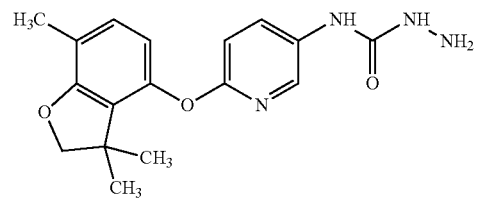 [SMILES: Cc1ccc(Oc2ccc(NC(=O)NN)cn2)c2c1OCC2(C)C]

Phenyl {6-[(3,3,7-trimethyl-2,3-dihydro-1-benzofuran-4-yl)oxy]-3-pyridinyl}carbamate (Intermediate 1, 640 mg, 1.64 mmol) was dissolved in dioxane (7 mL) and hydrazine monohydrate (8.2 mmol) was added. The reaction mixture was stirred for 30 minutes at room temperature and then at 70° C. for 1 hour. Water was added and the resulting suspension was stirred for 1 hour and then filtered. The solid was collected, washed with water and dried under vacuum at 25° C. affording the title compound (340 mg) as off-white solid.

¹H-NMR (400 MHz, DMSO-d₆): δ ppm 8.75 (br. s, 1H, 8.24 (d, 1H, J=2.63 Hz), 8.03 (dd, 1H, J=8.78, 2.64 Hz), 7.50 (br. s, 1H), 6.92 (d, 1H, J7.90 Hz), 5.88 (d, 1H, J=8.78 Hz), 6.35 (d, 1H, J=8.34 Hz), 4.36 (br. s, 2H), 4.19 (s, 2H), 2.11 (s, 3H), 1.26 (s, 6H). ¹³C-NMR (200 MHz, DMSO-d6): δ 158.5, 158.0, 157.5, 149.3, 137.5, 132.6, 130.8, 129.8, 125.6, 114.8, 113.6, 110.5, 83.7, 42.2, 26.0, 14.4. UPLC_A: 0.85 min, 329.16 [M+H]+.

Intermediate 3

1-[2-(hydroxymethyl)-6-(methoxymethoxy)phenyl]-2,2-dimethyl-propan-1-ol

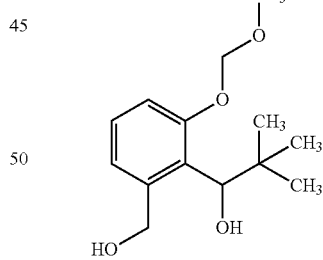

To a solution of tert-butyl-[[3-(methoxymethoxy)phenyl]methoxy]-dimethyl-silane (WO2012/076877 Intermediate 103, 500 mg, 1.77 mmol) in dry Hexane (5 mL), at room temperature, butyllithium 1.6M solution in Hexane (1.33 ml, 2.12 mmol) was slowly added and the reaction mixture was stirred for 2 hours at the same temperature. 2,2-dimethylpropanal (152.5 mg, 1.77 mmol) was added and the reaction mixture was stirred for further 30 minutes at the same temperature. The reaction was quenched with water (5 ml), diluted with an aqueous saturated solution of ammonium chloride (20 ml), and extracted with ethyl acetate (2×50 ml). The organic layer was dried (Na₂SO₄), filtered and evaporated. The residue was dissolved in THF (10 mL) and a 1M solution in THF of tetrabutylammonium fluoride (1.77 ml, 1.77 mmol) was added. The reaction mixture was stirred for 30 minutes at room temperature. The reaction was diluted with an aqueous saturated solution of ammonium chloride (20 ml), and extracted with ethyl acetate (2×50 ml). The organic layer was dried (Na₂SO₄), filtered and evaporated and the residue was purified by flash chromatography (Biotage system) on silica gel using a SNAP 25 g as column and cyclohexane/ethyl acetate from 100:0 to 70:30 as eluent affording the title compound (300 mg) as colorless oil.

LC/MS: QC_8_MIN: Rt=4.793 min; 277 [M+Na]+, 531 [2M+Na]⁺

Intermediate 4

1-tert-butyl-7-(methoxymethoxy)-1,3-dihydroisobenzofuran

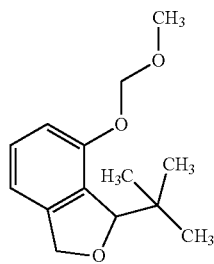 [SMILES: COCOc1cccc2c1C(C(C)(C)C)OC2]

To a solution of 1-[2-(hydroxymethyl)-6-(methoxymethoxy)phenyl]-2,2-dimethyl-propan-1-ol (Intermediate 3, 300 mg, 1.18 mmol) in dry THF (5 mL) at 0 C butyllithium 1.6M solution in hexane (0.74 ml, 1.18 mmol) was slowly added and the reaction mixture was stirred for 5 minutes at the same temperature. 4-methylbenzenesulfonyl chloride (224.89 mg, 1.18 mmol) dissolved in THF (1 ml) was slowly added and the reaction mixture was stirred for 5 minutes at the same temperature. Butyllithium 1.6M solution in hexane (0.74 ml, 1.18 mmol) was slowly added and the reaction mixture was stirred for 30 minutes at at 0° C. The reaction was quenched with water (1 ml), diluted with brine (10 ml) and extracted with ethyl acetate (2×15 ml). The organic layer was dried (Na₂SO₄), filtered and evaporated and The residue was purified by flash chromatography (Biotage system) on silica gel using a SNAP 25 g as column and cyclohexane/ethyl acetate from 100:0 to 70:30 as eluent affording the title compound (260 mg) as colorless oil.

LC/MS: QC_8_MIN: Rt=5.961 min; 473 [2M+H]+.

Intermediate 5

3-tert-butyl-1,3-dihydroisobenzofuran-4-ol

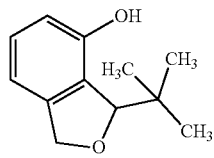

To a solution of 1-tert-butyl-7-(methoxymethoxy)-1,3-dihydroisobenzofuran (Intermediate 4, 260 mg, 1.10 mmol) in Methanol (10 mL) a 6N aqueous solution of hydrogen chloride (0.18 ml, 1.10 mmol) was added and the reaction mixture was stirred for 10 hours at 50° C. Volatiles were removed under reduced pressure and the residue was partitioned between water (10 ml) and ethyl acetate (20 ml). The organic layer was dried (Na₂SO₄), filtered and evaporated affording the title compound (220 mg) as white solid.

LC/MS: QC_3_MIN: Rt=1.764 min; 175 [(M−H₂O)+H]+.

Intermediate 6 methyl (2E/Z)-2-(1-ethoxyethylidene)hydrazinecarboxylate

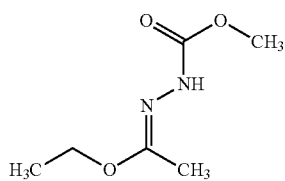

A mixture of methyl hydrazinocarboxylate (3.5 g, 38.8 mmol) and p-toluensulfonic acid (148 mg, 0.78 mmol) in Ethanol (7 ml) was purged with N2 and triethyl orthoacetate (7.45 g, 40.8 mmol) was added. The mixture was stirred at 60° C. for 4 h. TLC shows the complete consumption of the starting material. To the solution was added NaHCO₃ (65 mg, 0.78 mmol) and the volatiles were evaporated in vacuo to give the title compound (5.6 g) as a waxy, colourless material. This compound was a mixture of E/Z isomers.

LC/MS: QC_3_MIN: Rt=0.227 min, 0.338 min.

Intermediate 7 methyl (2E/Z)-2-{1-[(2-chloropyrimidin-5-yl)amino]ethylidene}hydrazinecarboxylate

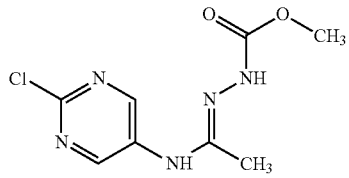 [SMILES: COC(=O)N/N=C(\C)Nc1cnc(Cl)nc1]

5-amino-2-chloro pyrimidine (260 mg, 2 mmol) was dissolved in DCM (5 ml), TEA (0.557 ml, 4 mmol) was added and the reaction mixture was stirred at 0° C. for 15 min. Acetyl chloride (0.213 ml, 3 mmol) was added dropwise at 0° C. and the reaction mixture was stirred for 45 min. The reaction was quenched with an aqueous saturated solution of NaHCO₃. The phases were separated and the aqueous phase was basified by adding solid K₂CO₃ while the pH was allowed to reach ~9-10 and extracted with dichloromethane. Combined organic phases were dried over Na₂SO₄ and evaporated in vacuo to afford N-(2-chloropyrimidin-5-yl)acetamide (340 mg) as a crude product.

It was suspended in POCl₃ (10 ml) and methyl hydrazinocarboxylate (198 mg, 2.2 mmol) was added. The mixture was heated to 60° C. and stirred for 4 h. The reaction was cooled to room temperature and the solution was poured into ice, followed by addition of K₂CO₃ solid until pH ~9.

Aqueous layer was extracted with ethyl acetate and the organic phase was dried over Na$_2$SO$_4$ and evaporated in vacuo to afford the title compound (420 mg) as a crude product.

LC/MS: QC_3_MIN: Rt=0.315 min; 244-246 [M+H]+.

Intermediate 8

4-(6-fluoropyridin-3-yl)-5-methyl-2,4-dihydro-3H-1,2,4-triazol-3-one

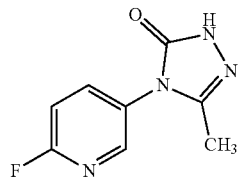

6-fluoropyridin-3-amine (500 mg, 4.4603 mmol) and methyl (2E/Z)-2-(1-ethoxyethylidene)hydrazinecarboxylate (Intermediate 6, 1072 mg, 6.69 mmol) were dissolved in Ethanol (3 mL). The mixture was heated to reflux to evaporate solvent and to obtain a slurry that was heated to 120° C. for 8 hours. After cooling ethyl acetate (5 mL) was added to form a precipitate. The solid was collected and purified by flash chromatography on silica gel (Biotage system) using a SNAP 25 g as column and dichloromethane/methanol from 99.5:0.5 to 93:7 as eluent affording the title compound (215 mg)

LC/MS: QC_3_MIN: Rt=0.426 min; 195[M+H]+.

Intermediate 9

4-(6-fluoro-5-methylpyridin-3-yl)-5-methyl-2,4-dihydro-3H-1,2,4-triazol-3-one

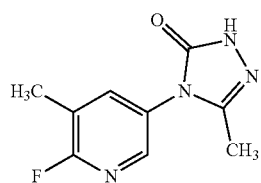

methyl (2E/Z)-2-(1-ethoxyethylidene)hydrazinecarboxylate (Intermediate 6, 705 mg, 4.40 mmol) and 6-fluoro-5-methyl-pyridin-3-amine (370 mg, 2.93 mmol) were dissolved in Ethanol (2 mL). The reaction was mechanically stirred at 100° C. to evaporate solvent. Obtained slurry was stirred solventless for 40 hours. After cooling ethyl acetate (3 mL) was added to obtain a precipitate. The solid was filtered, collected and dried in vacuo to afford the title compound (150 mg).

LC/MS: QC_3_MIN: Rt=0.711 min; 209 [M+H]+.

Intermediate 10

4-fluoro-3-(methyloxy)phenol

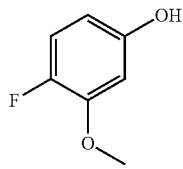

To a solution of 4-fluoro-3-(methyloxy)benzaldehide (1.54 g, 10 mmol) in DCM (30 mL) meta-chloroperbenzoic acid (2.59 g, 15 mmol) was added portionwise and the reaction mixture was stirred for 3 hours at room temperature. A second portion of m-CPBA (2.59 g, 15 mmol) was added and the reaction mixture was stirred for further 18 hrs. The mixture was diluted with DCM (100 mL), washed with an aqueous saturated solution of Na$_2$S$_2$O$_3$ (2×100 mL) and then with an aqueous saturated solution of NaHCO$_3$ (50 mL), dried over Na$_2$SO$_4$ and concentrated in vacuo to yield a yellow gum, which was re-dissolved in MeOH (20 mL) and Triethylamine (0.1 ml) was added. The reaction mixture was stirred for 18 hrs at room temperature and concentrated in vacuo. The residue was re-dissolved in Et$_2$O (100 mL) and extracted with an aqueous 1N solution of NaOH (50 mL). The aqueous layer was acidified with aqueous 2N HCl to pH=1 and extracted with Et$_2$O (2×50 mL). The combined organic layers were dried over Na2SO4 and concentrated in vacuo to afford the title compound (830 mg, yield: 35%).

$^1$HNMR (400 MHz, CDCl$_3$): δ ppm 6.81-6.85 (1H, t), 6.40-6.43 (1H, m), 6.21-6.24 (1H, m), 4.61 (1H, s), 3.76 (3H, s).

Intermediate 11

4-{[4-methyl-3-(methyloxy)phenyl]oxy}aniline

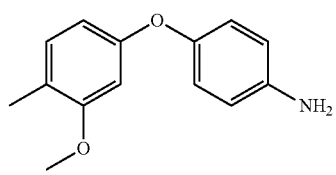 [SMILES: COc1cc(Oc2ccc(N)cc2)ccc1C]

To a solution of 4-methyl-3-(methyloxy)phenol (WO2012/076877 Intermediate 18, 0.800 g) in dry acetonitrile (60 mL) potassium carbonate (1.600 g, 11.58 mmol) and then 1-fluoro-4-nitrobenzene (817 mg, 5.79 mmol) were added and the reaction mixture was refluxed for 6 hours. The solid was filtered off and the solvent evaporated affording the nitro intermediate (1.43 g) as an orange solid. It was dissolved in tetrahydrofuran (65 mL)/water (32.5 mL) and iron (1.540 g, 27.6 mmol) and then ammonium chloride (1.475 g, 27.6 mmol) were added and the reaction mixture was stirred for 5 hours at room temperature. The catalyst was filtered off and the solution was diluted with a saturated solution of Na$_2$CO$_3$ (10 mL) and extracted with ethyl acetate (2 times 60 mL). Combined organic layers were dried over sodium sulphate, filtered and evaporated to afford the title compound (1.25 g) as a brown/red solid.

$^1$H-NMR (400 MHz, DMSO-d$_6$) δ ppm: 7.00 (1H, d), 6.77-6.70 (2H, m), 6.60-6.51 (3H, m), 6.24 (1H, dd), 4.94 (2H, br. s), 3.71 (3H, s), 2.06 (3H, s); UPLC_B: 0.86 min, 230 [M+H]+.

The following compounds were prepared using the foregoing methodology, replacing 4-methyl-3-(methyloxy)phenol with the appropriate phenol as described in the foregoing Reaction Schemes. Final products were purified, when needed, by flash-chromatography (Silica cartridge; Cyclohexane/EtOAc, dichloromethane/methanol or other appropriate solvent system).

| Int. | Structure | Name | Phenol | Mass |
|---|---|---|---|---|
| 12 | 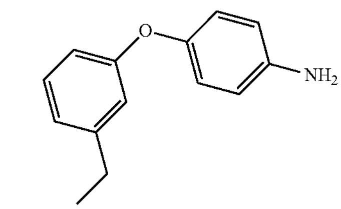 [SMILES: CCc1cccc(Oc2ccc(N)cc2)c1] | 4-{[3-ethylphenyl]oxy}aniline | 3-ethylphenol | MS_1 (ESI) m/z calcd. For $C_{15}H_{17}NO$ 213.28, found 214.0 (MH$^+$). |
| 13 | 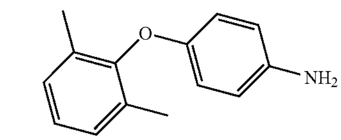 [SMILES: Cc1cccc(C)c1Oc1ccc(N)cc1] | 4-{[2,6-dimethylphenyl]oxy}aniline | 2,6-dimethylphenol | MS_1 (ESI) m/z calcd. For $C_{15}H_{17}NO$ 213.28, found 214.0 (MH$^+$). |
| 14 | 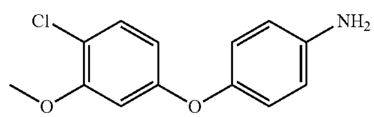 [SMILES: COc1cc(Oc2ccc(N)cc2)ccc1Cl] | 4-{[4-chloro-3-(methyloxy)phenyl]oxy}aniline | 4-chloro-3-(methyloxy)phenol | MS_1 (ESI) m/z calcd. For $C_{13}H_{12}ClNO_2$ 249.69 (M), found 250 (MH$^+$). |
| 15 | 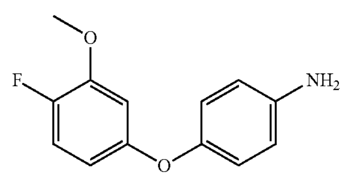 [SMILES: COc1cc(Oc2ccc(N)cc2)ccc1F] | 4-{[4-fluoro-3-(methyloxy)phenyl]oxy}aniline | 4-fluoro-3-(methyloxy)phenol (Intermediate 10) | MS_1 (ESI) m/z calcd for $C_{13}H_{12}FNO_2$ 233.24, found 234 (M + H$^+$). |
| 16 | 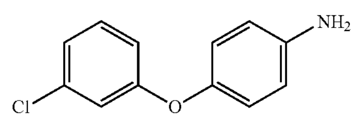 [SMILES: Nc1ccc(Oc2cccc(Cl)c2)cc1] | 4-{[3-chlorophenyl]oxy}aniline | 3-chlorophenol | MS_1 (ESI) m/z calcd. For $C_{12}H_{10}ClNO$ 219.67, found 220 (M + H$^+$). |
| 17 | 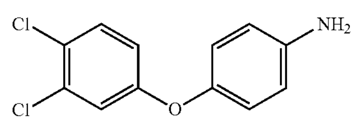 [SMILES: Nc1ccc(Oc2ccc(Cl)c(Cl)c2)cc1] | 4-{[3,4-dichlorophenyl]oxy}aniline | 3,4-dichlorophenol | MS_1 (ESI) m/z calcd. For $C_{12}H_9Cl_2NO$ 254.11, found 255 (M + H$^+$). |
| 18 | 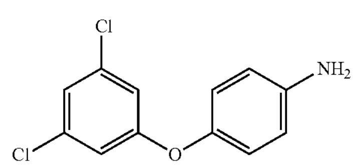 [SMILES: Nc1ccc(Oc2cc(Cl)cc(Cl)c2)cc1] | 4-{[3,5-dichlorophenyl]oxy}aniline | 3,5-dichlorophenol | MS_1 (ESI) m/z calcd. For $C_{12}H_9Cl_2NO$ 254.11, found 255 (M + H$^+$). |
| 19 | 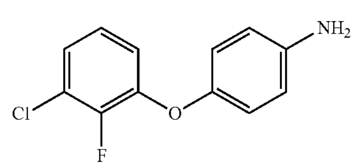 [SMILES: Nc1ccc(Oc2cccc(Cl)c2F)cc1] | 4-{[3-chloro-2-fluorophenyl]oxy}aniline | 3-chloro-2-fluorophenol | MS_1 (ESI) m/z calcd. For $C_{12}H_9ClFNO$ 237.66, found 238 (M + H$^+$). |
| 20 | 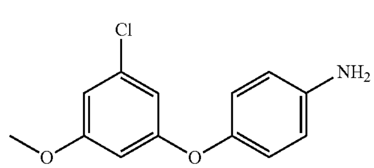 [SMILES: COc1cc(Cl)cc(Oc2ccc(N)cc2)c1] | 4-{[5-chloro-3-(methyloxy)phenyl]oxy}aniline | 5-chloro-3-(methyloxy)phenol | MS_1 (ESI) m/z calcd. For $C_{13}H_{12}ClNO_2$ 249.69 (M), found 250 (MH$^+$). |

Intermediate 21 methyl (2E and 2Z)-2-[1-(methyloxy)ethylidene]hydrazinecarboxylate

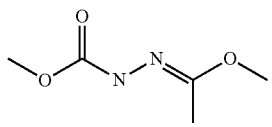

A mixture of methyl carbazate (7 g, 78 mmol, 1 equiv) and TsOH (0.296 g, 1.554 mmol, 0.02 equiv) in methanol (14 mL) was purged with $N_2$ and trimethyl orthoacetate (9.8 g, 82 mmol, 1.05 equivl) was added. The mixture was shaken at 60° C. for 3.5 h. To the resulting clear coulourless solution was added $NaHCO_3$ (169 mg, 0.02 mmol) and volatiles were evaporated in vacuo to give the title compound as a mixture of E,Z isomers.

MS_1 (ESI) m/z calcd for $C_5H_{10}N_2O_3$ 146.14, found 147 (MH+).

Intermediate 22

4-(4-bromophenyl)-5-methyl-2,4-dihydro-3H-1,2,4-triazol-3-one

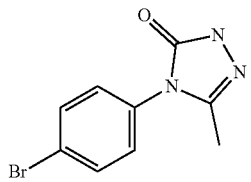

A large microwave tube was filled in with 2-acetyl-N-(4-bromophenyl)hydrazinecarboxamide (1.8 g, 6.62 mmol) and 2M aqueous NaOH (9 mL, 18 mmol). The reaction mixture was heated under microwave irradiation for 20 min at 130° C. Water (ca 18 mL) was added and the pH was adjusted to 4 by dropwise addition of aqueous HCl, with stirring. The thick precipitate was collected by filtration, washed with small amounts of cold water and dried. A small amount (220 mg) was purified by analytical preparation leading to 195 mg of the title compound.

$^1$H-NMR (400 MHz; MeOD): δ ppm 7.74 (2H, d), 7.36 (2H, d), 2.16 (3H, s).

Intermediate 23

4-[4-fluoro-3-(trifluoromethoxy)phenoxy]aniline

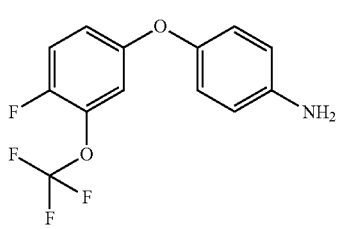 [SMILES: Nc1ccc(Oc2ccc(F)c(OC(F)(F)F)c2)cc1]

A mixture of 1-fluoro-4-nitro-benzene (144 mg, 1.02 mmol), 4-fluoro-3-(trifluoromethoxy)phenol (200 mg, 1.02 mmol) and Potassium carbonate (212 mg, 1.53 mmol) in DMF (3 mL) was stirred at 80° C. for 2 h. After this time the reaction was diluted with H2O (5 mL) and EtOAc (8 mL), phases were separated and organics were dried over $Na_2SO_4$, filtered and evaporated in vacuo to afford the nitro intermediate that was dissolved in Ethanol (5 mL), Iron (399 mg, 7.14 mmol) and 6N HCl in water (0.17 ml, 0.02 mmol) were added and the resulting mixture was stirred at 80° C. for 1.5 h. After this time the mixture was cooled down to room temperature and filtered, the residue was treated with $NaHCO_3$ (aq) sat. until basic pH. EtOAc (10 mL) was added and phases were separated. Organics were dried over $Na_2SO_4$, filtered and evaporated in vacuo to afford the title compound that was used in the next step without further purifications.

LC/MS: QC_3_MIN: Rt=2.094 min; 288 [M+H]+.

Intermediate 24

3-methyl-5-nitro-2-{[3-(2-methylethyl)phenyl]oxy}-pyridine

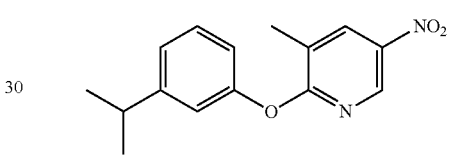

To a solution of 3-isopropylphenol (174 mg, 1.28 mmol) in DMSO (5 mL) tBuOK (143 mg, 1.28 mmol) was added and the reaction mixture was stirred at 20° C. for 30 mins. 2-chloro-3-methyl-5-nitropyridine (200 mg, 1.16 mmol) was added and the resulting mixture was stirred at 120° C. for 2 hrs. The reaction mixture was cooled to r. t., poured into ice-water (20 ml) and extracted with DCM (3×50 mL). The combined organic layer was dried over $Na_2SO_4$, filtered and concentrated to afford the title compound (279 mg) as a light red oil.

MS_1 (ESI) m/z calcd. For $C_{15}H_{16}N_2O_3$ 272.31, found 273 (M+H).

Intermediate 25

3-methyl-5-nitro-2-{[3-(ethyloxy)phenyl]oxy}-pyridine

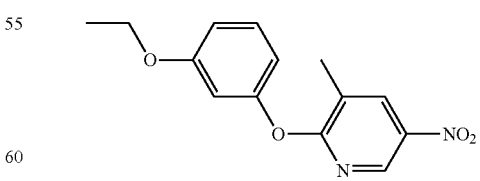

The title compound was prepared in a similar way with respect to Intermediate 24 replacing 3-isopropylphenol with 3-ethoxyphenol.

MS_1 (ESI) m/z calcd. For $C_{14}H_{14}N_2O_4$ 274.10, found 275.1 (M+H+).

Intermediate 26

5-amino-3-methyl-2-{[3-(2-methylethyl)phenyl]oxy}-pyridine

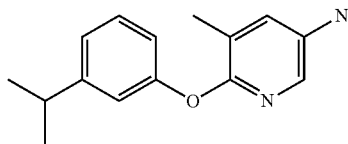 [SMILES: Cc1cc(N)cnc1Oc1cccc(C(C)C)c1]

To a solution of 3-methyl-5-nitro-2-{[3-(2-methylethyl)phenyl]oxy}-pyridine (Intermediate 24, 279 mg, 1.03 mmol) in MeOH (20 mL) and EtOAc (20 mL) Pd/C (10%, 28 mg, 0.1 wet. e.q.) was added and the flask was evacuated and backfilled with H2. The resulting mixture was stirred at r. t. under $H_2$ atmosphere overnight and filtered through a pad of Celite. The filtrate was concentrated in vacuo to afford the title compound (200 mg) as a grey solid.

MS_1 (ESI) m/z m/z calcd. For $C_{15}H_{18}N_2O$ 242.32, found 243 (M+H+).

Intermediate 27

5-amino-3-methyl-2-{[3-(ethyloxy)phenyl]oxy}-1-pyridine

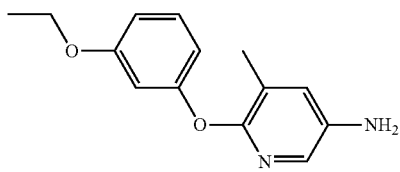 [SMILES: CCOc1cccc(Oc2ncc(N)cc2C)c1]

The title compound was prepared in a similar way with respect to Intermediate 26 replacing 3-methyl-5-nitro-2-{[3-(2-methylethyl)phenyl]oxy}-pyridine (Intermediate 24) with 3-methyl-5-nitro-2-{[3-(ethyloxy)phenyl]oxy}-pyridine (Intermediate 25).

MS_1 (ESI) m/z calcd. For $C_{14}H_{16}N_2O_2$ 244.12, found 245.0 (M+H+).

Intermediate 28 methyl (2E and 2Z)-2-[1-(methyloxy)methylidene]hydrazinecarboxylate

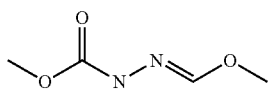

The title compound was prepared in a similar way with respect to Intermediate 21 replacing trimethyl orthoacetate with trimethyl orthoformate.

MS_1 (ESI) m/z calcd for $C_4H_8N_2O_3$ 132, found 133 (MH+).

Intermediate 29

4-methyl-3-(trifluoromethoxy)phenol

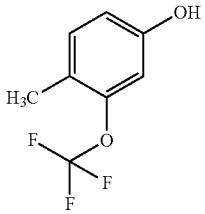

A solution of 4-hydroxy-2-(trifluoromethoxy)benzaldehyde (210 g, 1 equiv) in ethanol: acetic acid 3:1 (1050 Lt) was treated with Pd/C 5% catalyst −50% wet (21 g) and stirred at 800 rpm under 5 bar of hydrogen for 2.5 hrs. A second aliquot of Pd/C 5% catalyst −50% wet (33.6 g) was then added and the mixture subjected to the same hydrogenation conditions until reaching 22 hrs in total. The reaction mixture was filtered on a charcoal cartridge and washed with ethanol (525 mL). The resulting clear solution was concentrated to ca. 420 mL and the residue diluted with ethyl acetate (1050 Lt) and an aqueous 10% solution of ammonium chloride (525 mL). The phases were allowed separating and the organic one washed with water (2×525 mL), dried over sodium sulfate, filtered and concentrated to dryness. The title compound was obtained as colorless oil (196 g).

1H-NMR (400 MHz, CDCl$_3$): δ ppm (d, 1H), 6.75 (s, 1H), 6.70 (dd, 1H), 2.23 (s, 3H).

Intermediate 30

2-[4-methyl-3-(trifluoromethoxy)phenoxy]-5-nitropyridine

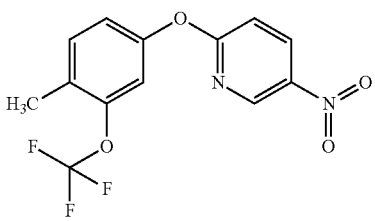 [SMILES: Cc1ccc(Oc2ccc([N+](=O)[O-])cn2)cc1OC(F)(F)F]

To a suspension of 4-methyl-3-(trifluoromethoxy)phenol (Intermediate 29, 364 mg, 1.89 mmol) and 2 chloro-5-nitropyridine (300 mg, 1.89 mmol) in acetonitrile (4 mL) was added K2CO3 (653 mg, 4.72 mmol) at room temperature. The mixture was heated at reflux for 18 hrs until completion. The resulting mixture was cooled down to room temperature, diluted with water (10 mL) and ethyl acetate (10 mL). Phases were separated, the organic layer was washed with an aqueous 10% solution of ammonium chloride (10 mL) and aqueous 13% solution of NaCl (10 mL). The organic layer was dried over $Na_2SO_4$ and evaporated to dryness to give the title compound (594 mg) as pale brown oil.

$^1$H-NMR (400 MHz, DMSO-d6): δ ppm 9.01 (d1H), 8.62 (dd, 1H), 7.47 (d, 1H), 7.31-7.25 (m, 2H), 7.21 (dd, 1H), 2.29 (s, 3H).

Intermediate 31

6-[4-methyl-3-(trifluoromethoxy)phenoxy]pyridin-3-amine

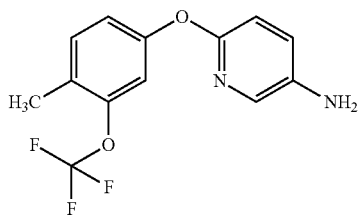 [SMILES: Cc1ccc(Oc2ccc(N)cn2)cc1OC(F)(F)F]

A suspension of 2-[4-methyl-3-(trifluoromethoxy)phenoxy]-5-nitropyridine (Intermediate 30, 594 mg, 1.89 mmol) and Pd/C 5% w/w (40 mg) in THF (3 mL) was hydrogenated under 5 bar of $H_2$, at 35° C. for 18 hrs. The mixture was filtered to remove the catalyst, diluted with ethyl acetate (10 mL) and washed with an aqueous 13% solution of NaCl (10 mL). The organic layer, dried over $Na_2SO_4$, was evaporated to give the title compound (475 mg) as brown oil.

$^1$H-NMR (400 MHz, DMSO-d6): δ ppm 7.54-7.51 (m, 1H), 7.31 (dd, 1H), 7.07 (dd, 1H), 6.92-6.87 (m, 2H), 6.79 (d, 1H), 5.14 (s, 2H), 2.21 (s, 3H).

Intermediate 32

N-{6-[4-methyl-3-(trifluoromethoxy)phenoxy]pyridin-3-yl}acetamide

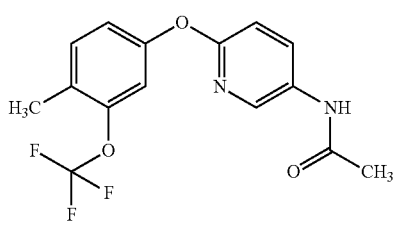 [SMILES: CC(=O)Nc1ccc(Oc2ccc(C)c(OC(F)(F)F)c2)nc1]

To a solution of 6-[4-methyl-3-(trifluoromethoxy)phenoxy]pyridin-3-amine (Intermediate 31, 475 mg, 1.67 mmol) and TEA (0.28 mL) in 5 mL of dry DCM under nitrogen at 0° C., acetyl chloride (0.13 mL) dissolved in 2 mL of dry DCM was added drop wise. The ice bath was then removed and the resulting solution was allowed to stir at room temperature for 30 minutes until complete conversion. Water was added and phases were separated. The organic phase was then washed with an aqueous 15% solution of $NaHCO_3$, dried over $Na_2SO_4$, filtered and concentrated to give the title compound (502 mg) as yellow oil.

$^1$H-NMR (400 MHz, DMSO-d$_6$): δ ppm 10.09 (1H, s), 8.28 (1H, d), 8.05 (1H, dd), 7.38 (1H, d), 6.97-7.13 (3H, m), 2.25 (3H, s), 2.03 (3H, s).

Intermediate 33

Methyl-2-[1-({6-[4-methyl-3-(trifluoromethoxy)phenoxy]pyridin-3-yl}amino)ethylidene]hydrazinecarboxylate

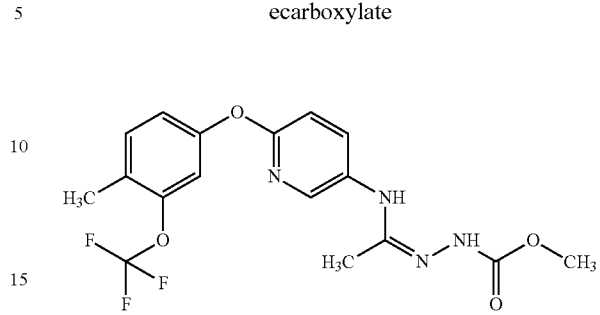

To a solution of N-{6-[4-methyl-3-(trifluoromethoxy)phenoxy]pyridin-3-yl}acetamide (Intermediate 32, 500 mg, 1.53 mmol) in 2.2 mL of $POCl_3$, methyl carbazate (152 mg) was added. The resulting mixture was heated at 60° C. for 7 hrs and overnight at room temperature. After additional heating for 5 hrs, further methyl carbazate (30 mg, 0.2 equiv) was added. The mixture was cooled to 0° C. and water was cautiously added, followed by a saturated solution of $K_2CO_3$ and then solid $K_2CO_3$ until pH=8 was reached. Ethyl acetate (50 mL) was then added and phases were separated. The aqueous phase was then back-extracted with ethyl acetate (2×50 mL). The combined organics were dried over $Na_2SO_4$, filtered and concentrated to give 520 mg of crude as orange foam which was purified by silica flash-chromatography, eluant cyclohexane/ethyl acetate, gradient from 50/50 to 20/80 v/v giving the title compound (360 mg) as white foam.

$^1$H-NMR (400 MHz, DMSO d$_6$): δ ppm 9.18-9.34 (1H, m), 8.64 (1H, s), 8.51 (1H, d), 8.11-8.26 (1H, m), 7.36 (1H, d), 6.93-7.06 (3H, m), 3.59 (3H, s), 2.24 (3H, s), 2.00 (3H, s).

Intermediate 34

2-fluoro-1,3-bis(methoxymethoxy)-4-methyl-benzene

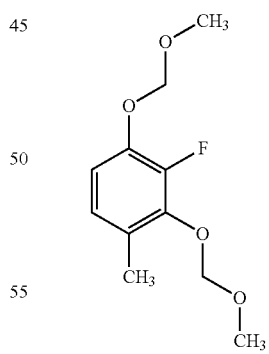

To a solution of 2,4-bis(methoxymethoxy)-1-methyl-benzene (WO2012/076877 Intermediate 150, 2000 mg, 9.4233 mmol) in dry THF (20 mL) butyllithium 1.6M in hexane (6.77 ml, 10.84 mmol) was slowly added and the reaction mixture was stirred for 30 minutes at room temperature. The reaction was cooled to −15° C. and it was added (via cannulation) to a solution of N-(benzenesulfonyl)-N-fluoro-benzenesulfonamide (3565.8 mg, 11.308 mmol) in dry THF (10 mL) at −15° C. The reaction mixture was stirred for 30 minutes at the same temperature. The reaction was quenched with brine (5 ml) diluted with water (20 ml) and extracted with ethyl acetate (2×30 ml). The organic layer was dried (Na2SO4), filtered and evaporated and the residue was purified by flash chromatography (Biotage system) on silica gel using a SNAP 50 g as column and cyclohexane/ethyl acetate from 100:0 to 80:20 as eluent affording the title compound (1950 mg) as colourless oil.

LC/MS: QC_3_MIN: Rt=2.177 min; 231 [M+H]+.

Intermediate 35

1-[2,6-bis(methoxymethoxy)-3-methyl-phenyl]cyclopropanecarbonitrile

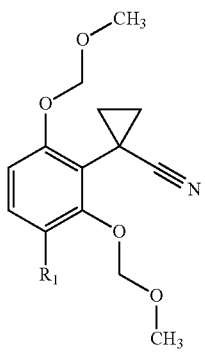

2-fluoro-1,3-bis(methoxymethoxy)-4-methyl-benzene (Intermediate 34, 17.5 g, 76.011 mmol) and cyclopropanecarbonitrile (22.625 g, 337.23 mmol) were warmed under stirring to 105° C. A solution of [bis(trimethylsilyl)amino]potassium 0.5M in Toluene (275 ml) was slowly added for 1 hour to the previous solution. The reaction mixture was stirred for 6 hour at the same temperature. After cooling the solid was filtered off and the filtrate was partitioned between Brine (200 ml) and ethyl acetate (300 ml). The aqueous layer was re-extracted with ethyl acetate (200 ml) and combined organic layers were dried (Na2SO4), filtered and evaporated (the temperature during the concentration was ~60° C. for removing the excess of cyclopropane carbonitrile). The residue was triturated with isopropanol (25 ml) and the solid collected and dried to afford the title compound (9.0 g) as white solid.

LC/MS: QC_3_MIN: Rt=2.172 min; 278 [M+H]+.

Intermediate 36

2-[1-(hydroxymethyl)cyclopropyl]-3-(methoxymethoxy)-6-methyl-phenol

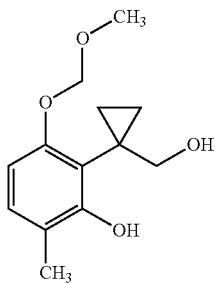 [SMILES: COCOc1ccc(C)c(O)c1C1(CO)CC1]

To a solution of 1-[2,6-bis(methoxymethoxy)-3-methyl-phenyl]cyclopropanecarbonitrile (Intermediate 35, 26.2 g, 94.476 mmol) in Methanol (260 mL) hydrogen chloride 6N in water (31.5 ml, 188.95 mmol) was added and the reaction mixture was stirred for 5 hours at 70° C. Volatiles were removed under reduced pressure and the residue was suspended in Toluene (50 ml) and the solvent evaporated. Additional Toluene (50 ml) was added and then re-evaporated. The residue (yellow pale solid) was dissolved in THF (200 mL) and the reaction mixture was cooled to 0° C. chloro(methoxy)methane (7.89 ml, 103.92 mmol) was added followed by a portionwise addition of sodium hydride 60% dispersion in mineral oil (4.1569 g, 103.92 mmol). The reaction mixture was stirred for 1 hour at the same temperature and then lithium aluminum hydride 1M in THF (47.24 ml, 47.24 mmol) was slowly added. The reaction mixture was stirred for 1 hour at 0° C. and then it was quenched with ice cold aqueous 2N HCl (100 ml), diluted with water (200 ml) and extracted with ethyl acetate (2×200 ml). The organic layer was dried (Na$_2$SO$_4$), filtered and evaporated and The residue was purified by flash chromatography on silica gel using a silica pad ~300 g of silica and cyclohexane/ethyl acetate from 100:0 to 70:30 as eluent affording the title compound (16.4 g) as colourless oil.

Example 1

4-{6-[(3,3-dimethyl-2,3-dihydro-1-benzofuran-4-yl)oxy]pyridin-3-yl}-5-methyl-2,4-dihydro-3H-1,2,4-triazol-3-one

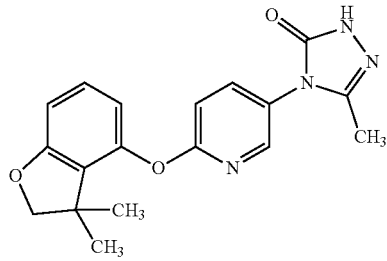 [SMILES: Cc1n[nH]c(=O)n1-c1ccc(Oc2cccc3c2C(C)(C)CO3)nc1]

To a solution of 3,3-dimethyl-2H-benzofuran-4-ol (WO2012/076877 Intermediate 50, 30 mg, 0.18 mmol) in dry DMF (0.5 mL) dipotassium carbonate (50.5 mg, 0.36 mmol) and then 4-(6-fluoro-3-pyridyl)-3-methyl-1H-1,2,4-triazol-5-one (Intermediate 8, 24.8 mg, 0.128 mmol) were added and the reaction mixture was stirred for 8 hours at 110° C. The reaction was quenched with water (1 ml), diluted with brine (5 ml) and extracted with ethyl acetate (2×10 ml). The organic layer was dried (Na$_2$SO$_4$), filtered and evaporated and the residue was purified by flash chromatography (Biotage system) on silica gel using a SNAP 10 g as column and dichloromethane/methanol from 99.5:0.5 to 95:5 as eluent affording the title compound (12 mg) as yellow pale solid.

$^1$H-NMR (400 MHz, DMSO-d$_6$): δ ppm 11.70 (s, 1H), 8.23 (d, 1H), 7.95 (dd, 1H), 7.20 (d, 1H), 7.15 (t, 1H), 6.66 (dd, 1H), 6.58 (dd, 1H), 4.22 (s, 2H), 2.06 (s, 3H), 1.28 (s, 6H).

LC/MS: QC_3_MIN: Rt=1.774 min; 339 [M+H]+.

The following compounds were prepared using the foregoing general methodology, replacing 3,3-dimethyl-2H-benzofuran-4-ol with the appropriate phenol. Final products were purified by flash-chromatography (Silica cartridge dichloromethane/methanol or other appropriate solvent system).

| Ex. | Structure | Name | Phenol | 1H-NMR | LCMS |
| --- | --- | --- | --- | --- | --- |
| 2 | 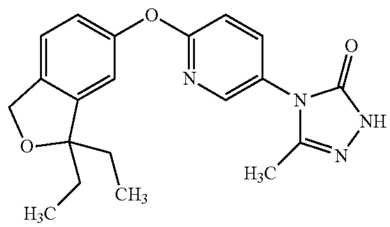 [SMILES: CCC1(CC)OCc2ccc(Oc3ccc(-n4c(C)n[nH]c4=O)cn3)cc21] | 4-{6-[(3,3-diethyl-1,3-dihydro-2-benzofuran-5-yl)oxy]pyridin-3-yl}-5-methyl-2,4-dihydro-3H-1,2,4-triazol-3-one | 3,3-diethyl-1,3-dihydro-2-benzofuran-5-ol (WO2012168710 Intermediate 19) | ¹H-NMR (400 MHz, DMSO-d6): δ ppm 11.65 (s, 1H), 8.21 (d, 1H), 7.94 (dd, 1H), 7.31 (d, 1H), 7.14 (d, 1H), 7.08 (dd, 1H), 7.02 (d, 1H), 5.01 (s, 2H), 2.06 (s, 3H), 1.74 (q, 4H), 0.69 (t, 6H). | LC/MS: QC_3_MIN: Rt = 2.552 min; 367 [M + H]+. |
| 3 | 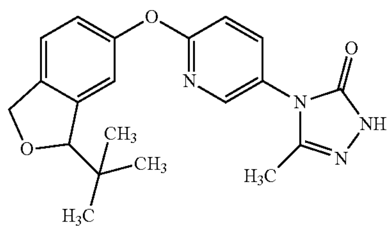 [SMILES: Cc1n[nH]c(=O)n1-c1ccc(Oc2ccc3c(c2)C(C(C)(C)C)OC3)nc1] | 4-{6-[(3-tert-butyl-1,3-dihydro-2-benzofuran-5-yl)oxy]pyridin-3-yl}-5-methyl-2,4-dihydro-3H-1,2,4-triazol-3-one (enantiomer 1) | 3-tert-butyl-1,3-dihydro-2-benzofuran-5-ol (WO2012168710 Intermediate 30, enantiomer 1) | ¹H-NMR (400 MHz, DMSO-d6): δ ppm 11.70 (s, 1H), 8.20 (d, 1H), 7.94 (dd, 1H), 7.35 (d, 1H), 7.17 (d, 1H), 7.08-7.15 (m, 2H), 4.94-5.09 (m, 2H), 4.83-4.87 (m, 1H), 2.06 (s, 3H), 0.91 (s, 9H). | LC/MS: QC_3_MIN: Rt = 1.866 min; 367 [M + H]+. |
| 4 | 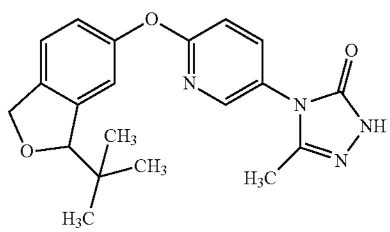 [SMILES: Cc1n[nH]c(=O)n1-c1ccc(Oc2ccc3c(c2)C(C(C)(C)C)OC3)nc1] | 4-{6-[(3-tert-butyl-1,3-dihydro-2-benzofuran-5-yl)oxy]pyridin-3-yl}-5-methyl-2,4-dihydro-3H-1,2,4-triazol-3-one (enantiomer 2) | 3-tert-butyl-1,3-dihydro-2-benzofuran-5-ol (WO2012168710 Intermediate 31, enantiomer 2) | ¹H-NMR (400 MHz, DMSO-d6): δ ppm 11.70 (s, 1H), 8.20 (d, 1H), 7.94 (dd, 1H), 7.35 (d, 1H), 7.17 (d, 1H), 7.08-7.15 (m, 2H), 4.94-5.09 (m, 2H), 4.83-4.87 (m, 1H), 2.06 (s, 3H), 0.91 (s, 9H). | LC/MS: QC_3_MIN: Rt = 1.866 min; 367 [M + H]+. |
| 5 | 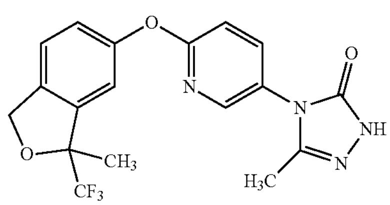 [SMILES: Cc1n[nH]c(=O)n1-c1ccc(Oc2ccc3c(c2)C(C)(C(F)(F)F)OC3)nc1] | 5-methyl-4-(6-{[3-methyl-3-(trifluoromethyl)-1,3-dihydro-2-benzofuran-5-yl]oxy}pyridin-3-yl)-2,4-dihydro-3H-1,2,4-triazol-3-one (enantiomer 1) | 3-methyl-3-(trifluoromethyl)-1,3-dihydro-2-benzofuran-5-ol (WO2012168710 Intermediate 32, enantiomer 1) | — | LC/MS: QC_3_MIN: Rt = 2.163 min; 393 [M + H]+. |
| 6 | 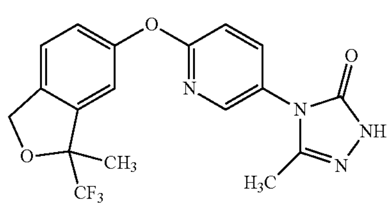 [SMILES: Cc1n[nH]c(=O)n1-c1ccc(Oc2ccc3c(c2)C(C)(C(F)(F)F)OC3)nc1] | 5-methyl-4-(6-{[3-methyl-3-(trifluoromethyl)-1,3-dihydro-2-benzofuran-5-yl]oxy}pyridin-3-yl)-2,4-dihydro-3H-1,2,4-triazol-3-one (enantiomer 2) | trifluoromethyl)-1,3-dihydro-2-benzofuran-5-ol (WO2012168710 Intermediate 33, enantiomer 2) | — | LC/MS: QC_3_MIN: Rt = 2.173 min; 393 [M + H]+. |
| 7 | 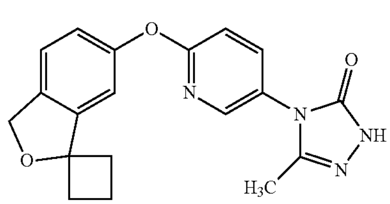 [SMILES: Cc1n[nH]c(=O)n1-c1ccc(Oc2ccc3c(c2)C2(CCC2)OC3)nc1] | 5-methyl-4-[6-(3H-spiro[2-benzofuran-1,1'-cyclobutan]-6-yloxy)pyridin-3-yl]-2,4-dihydro-3H-1,2,4-triazol-3-one | 3H-spiro[2-benzofuran-1,1'-cyclobutan]-6-ol (WO2012168710 Intermediate 24) | ¹H-NMR (400 MHz, DMSO-d6): δ ppm 11.65 (s, 1H), 8.21 (d, 1H), 7.95 (dd, 1H), 7.38 (d, 1H), 7.30 (d, 1H), 7.19 (d, 1H), 7.09 (dd, 1H), 4.97 (s, 2H), 2.42-2.53 (m, 2H), 2.28-2.38 (m, 2H), 2.07 (s, 3H), 1.78-1.98 (m, 2H), | LC/MS: QC_3_MIN: Rt = 1.790 min; 351 [M + H]+. |

-continued

| Ex. | Structure | Name | Phenol | 1H-NMR | LCMS |
|---|---|---|---|---|---|
| 8 | 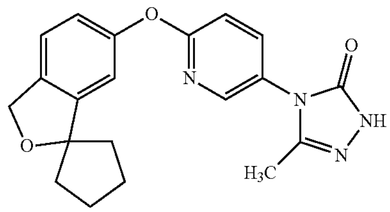 [SMILES: Cc1n[nH]c(=O)n1-c1ccc(Oc2ccc3c(c2)C2(CCCC2)OC3)nc1] | 5-methyl-4-[6-(3H-spiro[2-benzofuran-1,1'-cyclopentan]-6-yloxy)pyridin-3-yl]-2,4-dihydro-3H-1,2,4-triazol-3-one | 3H-spiro[2-benzofuran-1,1'-cyclopentan]-6-ol (WO2012168710 Intermediate 25) | ¹H-NMR (400 MHz, DMSO-d6): δ ppm 11.65 (s, 1H), 8.20 (d, 1H), 7.93 (dd, 1H), 7.30 (d, 1H), 7.18 (d, 1H), 7.12 (d, 1H), 7.06 (dd, 1H), 4.93 (s, 2H), 2.06 (s, 3H), 1.73-1.97 (m, 8H). | LC/MS: QC_3_MIN: Rt = 1.864 min; 365 [M + H]+. |
| 9 | 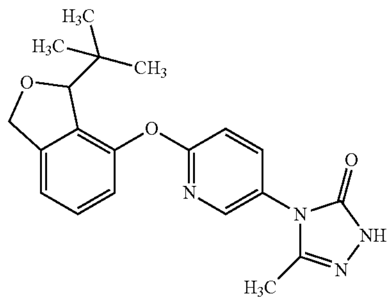 [SMILES: Cc1n[nH]c(=O)n1-c1ccc(Oc2cccc3c2C(C(C)(C)C)OC3)nc1] | 4-{6-[(3-tert-butyl-1,3-dihydro-2-benzofuran-4-yl)oxy]pyridin-3-yl}-5-methyl-2,4-dihydro-3H-1,2,4-triazol-3-one (racemate) | 3-tert-butyl-1,3-dihydroiso-benzofuran-4-ol (Intermediate 5) | ¹H-NMR (400 MHz, DMSO-d6): δ ppm 11.70 (br. S, 1H), 8.22 (d, 1H), 7.95 (dd, 1H), 7.37 (t, 1H), 7.19 (d, 1H), 7.15 (d, 1H), 7.05 (d, 1H), 5.10-5.17 (m, 1H), 4.93-4.97 (m, 1H), 4.77 (d, 1H), 2.06 (s, 3H), 0.88 (s, 9H). | LC/MS: QC_3_MIN: Rt = 2.265 min; 367 [M + H]+. |

Example 10

5-methyl-4-{6-[(3,3,7-trimethyl-2,3-dihydro-1-benzofuran-4-yl)oxy]-3-pyridinyl}-2,4-dihydro-3H-1,2,4-triazol-3-one

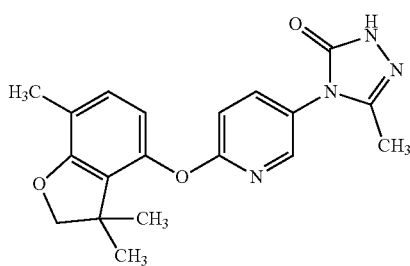 [SMILES: Cc1ccc(Oc2ccc(-n3c(C)n[nH]c3=O)cn2)c2c1OCC2(C)C]

The crude N-{6-[(3,3,7-trimethyl-2,3-dihydro-1-benzofuran-4-yl)oxy]pyridin-3-yl}hydrazinecarboxamide (330 mg, 1.0 mmol) was suspended in EtOH (4.5 mL) and triethyl orthoacetate (3 equiv) was added, followed by p-toluenesulfonic acid hydrate (0.1 equiv). The resulting solution was heated to reflux for 24 hrs and then evaporated to dryness. Since the reaction was not complete, the residue was re-dissolved in EtOH (4.5 mL), more triethyl orthoacetate (3 equiv) and p-toluenesulfonic acid hydrate (0.1 equiv) were added and the solution stirred at reflux for additional 18 hours. The mixture was cooled to room temperature and diluted with ethyl acetate and water. Saturated $Na_2CO_3$ solution was added the layers were separated and the organic washed with brine, dried over $Na_2SO_4$ and evaporated to dryness. The residue was purified via silica chromatography, eluting with cyclohexane/ethyl acetate from 5/5 to 3/7. The fractions containing the product were combined and evaporated to dryness. The residue was further purified by triturating with methyl tert-butyl ether/n-heptanes. The solid was collected and washed with n-heptanes to afford 5-methyl-4-{6-[(3,3,7-trimethyl-2,3-dihydro-1-benzofuran-4-yl)oxy]pyridin-3-yl}-2,4-dihydro-3H-1,2,4-triazol-3-one as a white solid (177 mg).

UPLC_A: 0.94 min, 353.17 [M+H]+, 351.50 [M−H]−. ¹H-NMR (400 MHz, DMSO-$d_6$): δ ppm 11.67 (br. s, 1H), 8.22 (dd, 1H), 7.92 (dd, 1H), 7.16 (d, 1H), 6.98 (dd, 1H), 6.49 (d, 1H), 4.21 (s, 2H), 2.13 (s, 3H), 2.06 (s, 3H), 1.26 (s, 6H). ¹³C-NMR (200 MHz, DMSO-$d_6$): δ 162.7, 158.6, 154.3, 148.1, 145.8, 143.9, 139.1, 130.0, 126.0, 125.2, 115.8, 114.4, 111.1, 83.6, 42.2, 26.0, 14.4, 12.1.

Example 11

4-{6-[(3,3-dimethyl-2,3-dihydro-1-benzofuran-4-yl)oxy]-5-methylpyridin-3-yl}-5-methyl-2,4-dihydro-3H-1,2,4-triazol-3-one

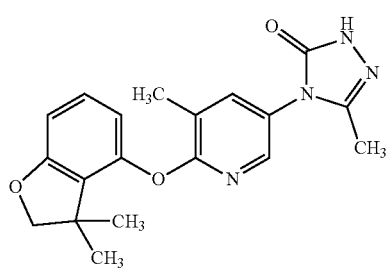 [SMILES: Cc1cc(-n2c(C)n[nH]c2=O)cnc1Oc1cccc2c1C(C)(C)CO2]

To a solution of 3,3-dimethyl-2H-benzofuran-4-ol (WO2012/076877 Intermediate 50, 30 mg, 0.18 mmol) in dry DMF (0.5 mL) dipotassium carbonate (50.5 mg, 0.365 mmol) and then 4-(6-fluoro-5-methyl-3-pyridyl)-3-methyl-1H-1,2,4-triazol-5-one (Intermediate 9, 38.0 mg, 0.18 mmol) were added and the reaction mixture was stirred for 16 hours at 110° C. The reaction was quenched with water (1 ml), diluted with brine (5 ml) and extracted with ethyl acetate (2×10 ml). The organic layer was dried ($Na_2SO_4$), filtered and evaporated and the residue was purified by flash chromatography (Biotage system) on silica gel using a SNAP 10 g as column and Dichloromethane/methanol from 99.5:0.5 to 95:5 as eluent affording the title compound (7 mg) as a yellow pale solid.

$^1$H-NMR (400 MHz, DMSO-d$_6$): δ ppm 11.70 (s, 1H), 8.02 (dd, 1H), 7.85 (dd, 1H), 7.12 (t, 1H), 6.63 (d, 1H), 6.56 (d, 1H), 4.21 (s, 2H), 2.38 (s, 3H), 2.16 (s, 3H), 1.28 (s, 6H). LC/MS: QC_3_MIN: Rt=1.872 min; 353 [M+H]+.

The following compounds were prepared using the foregoing general methodology, replacing 3,3-dimethyl-2H-benzofuran-4-ol with the appropriate phenol. Final products were purified by flash-chromatography (Silica cartridge dichloromethane/methanol or other appropriate solvent system).

(Intermediate 6, 40 mg, 0.25 mmol) was added and the reaction mixture was stirred for 8 hours at 100° C. in a sealed vial. Volatiles were removed under reduced pressure and the residue was purified by flash chromatography (Biotage system) on silica gel using a SNAP 10 g as column and cyclohexane/ethyl acetate from 50:50 to 0:100 as eluents affording the title compound (23 mg) as a white solid.

$^1$H-NMR (400 MHz, DMSO-d$_6$): δ ppm 11.70 (s, 1H), 8.21 (d, 1H), 7.92 (dd, 1H), 7.11 (d, 1H), 6.93 (d, 1H), 6.45 (d, 1H), 4.44 (s, 2H), 2.14 (s, 3H), 2.06 (s, 3H), 1.09-1.13 (m, 2H), 0.87-0.91 (m, 2H).

LC/MS: QC_3_MIN: Rt=1.918 min; 351 [M+H]+.

| Ex. | Structure | Name | Phenol | 1H-NMR | LCMS |
|---|---|---|---|---|---|
| 12 | 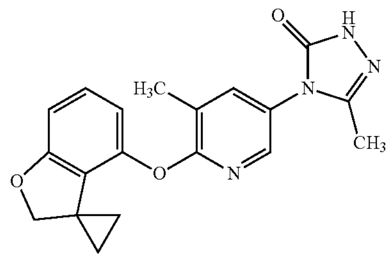 [SMILES: Cc1cc(-n2c(C)n[nH]c2=O)cnc1Oc1cccc2c1C1(CC1)CO2] | 5-methyl-4-[5-methyl-6-(spiro[1-benzofuran-3,1'-cyclopropan]-4-yloxy)pyridin-3-yl]-2,4-dihydro-3H-1,2,4-triazol-3-one | spiro[1-benzofuran-3,1'-cyclopropan]-4-ol (WO2012/076877 Intermediate 85) | $^1$H-NMR (400 MHz, DMSO-d6): δ ppm 11.65 (s, 1H), 8.01 (d, 1H), 7.83 (dd, 1H), 7.07 (t, 1H), 6.65 (d, 1H), 6.52 (d, 1H), 4.45 (s, 2H), 2.31 (s, 3H), 2.06 (s, 3H), 1.13-1.18 (m, 2H), 0.89-0.94 (m, 2H). | LC/MS: QC_3_MIN: Rt = 1.782 min; 351 [M + H]+. |
| 13 | 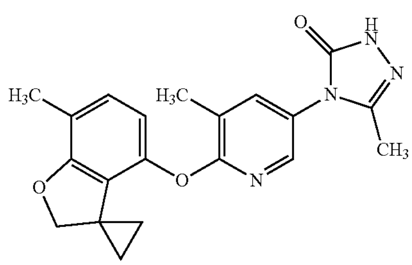 [SMILES: Cc1cc(-n2c(C)n[nH]c2=O)cnc1Oc1ccc(C)c2c1C1(CC1)CO2] | 5-methyl-4-{5-methyl-6-[(7-methylspiro[1-benzofuran-3,1'-cyclopropan]-4-yl)oxy]pyridin-3-yl}-2,4-dihydro-3H-1,2,4-triazol-3-one | 7-methylspiro[2H-benzofuran-3,1'-cyclopropane]-4-ol (WO2012/076877 Intermediate 156) | $^1$H-NMR (400 MHz, DMSO-d6): δ ppm 11.65 (s, 1H), 7.99 (d, 1H), 7.81 (d, 1H), 6.91 (d, 1H), 6.43 (d, 1H), 4.44 (s, 2H), 2.30 (s, 3H), 2.13 (s, 3H), 2.05 (s, 3H), 1.08-1.13 (m, 2H), 0.86-0.91 (m, 2H). | LC/MS: QC_3_MIN: Rt = 1.947 min; 365 [M + H]+. |

Example 14

5-methyl-4-{6-[(7-methylspiro[1-benzofuran-3,1'-cyclopropan]-4-yl)oxy]pyridin-3-yl}-2,4-dihydro-3H-1,2,4-triazol-3-one

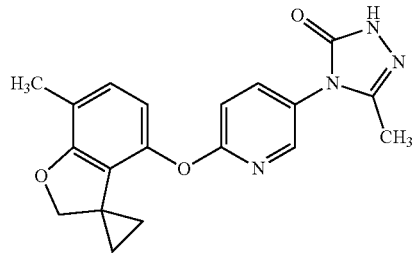 [SMILES: Cc1ccc(Oc2ccc(-n3c(C)n[nH]c3=O)cn2)c2c1OCC21CC1]

To a solution of 6-(7-methylspiro[2H-benzofuran-3,1'-cyclopropane]-4-yl)oxypyridin-3-amine (WO2012/076877 Intermediate 158, 40 mg, 0.15 mmol) in methanol (1 ml) methyl (2E/Z)-2-(1-ethoxyethylidene)hydrazinecarboxylate

Example 15

5-methyl-4-[6-(spiro I[1-benzofuran-3,1'-cyclopropan]-4-yloxy)pyridin-3-yl]-2,4-dihydro-3H-1,2,4-triazol-3-one

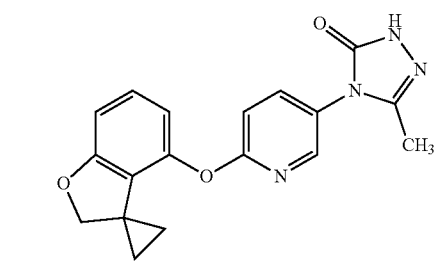 [SMILES: Cc1n[nH]c(=O)n1-c1ccc(Oc2cccc3c2C2(CC2)CO3)nc1]

To a solution of 6-spiro[2H-benzofuran-3,1'-cyclopropane]-4-yloxypyridin-3-amine (WO2012/076877 Intermediate 87, 25 mg, 0.1 mmol) in Methanol (1 mL) methyl (2E/Z)-2-(1-ethoxyethylidene)hydrazinecarboxylate (Intermediate 6, 19.7 mg, 0.123 mmol) was added and the reaction mixture was stirred for 10 hours at 100° C. in a sealed vial. Volatiles were removed under reduced pressure and the residue was purified by flash chromatography (Biotage system) on silica gel using a SNAP 10 g as column and Dichloromethane/methanol from 99.5:0.5 to 95:5 as eluent affording the title compound (14 mg) as white solid.

¹H-NMR (400 MHz, DMSO-d₆): δ ppm 11.70 (br. S, 1H), 8.23 (d, 1H), 7.95 (dd, 1H), 7.15 (d, 1H), 7.09 (t, 1H), 6.68 (d, 1H), 6.54 (d, 1H), 6.45 (s, 2H), 2.06 (s, 3H), 1.13-1.18 (m, 2H), 0.89-0.94 (m, 2H).

LC/MS: QC_3_MIN: Rt=1.767 min; 337 [M+H]+.

Example 16

5-methyl-4-{2-[(7-methylspiro[1-benzofuran-3,1'-cyclopropan]-4-yl)oxy]pyrimidin-5-yl}-2,4-dihydro-3H-1,2,4-triazol-3-one

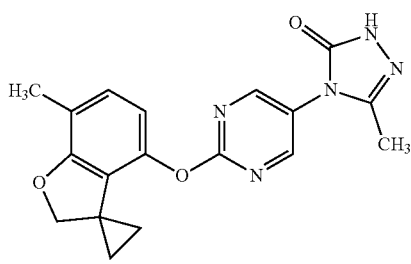 [SMILES: Cc1ccc(Oc2ncc(-n3c(C)n[nH]c3=O)cn2)c2c1OCC21CC1]

To a solution of 7-methylspiro[2H-benzofuran-3,1'-cyclopropane]-4-ol (WO2012/076877 Intermediate 156, 25 mg, 0.14 mmol) in dry DMF (1 ml) potassium carbonate (41.4 mg, 0.3 mmol) and then methyl (2E/Z)-2-{1-[(2-chloropyrimidin-5-yl)amino]ethylidene}hydrazinecarboxylate (Intermediate 7, 31 mg, 0.13 mmol) were added and the reaction mixture was stirred for 4 hours at 80° C. After cooling the reaction was quenched with water (1 ml), diluted with brine (5 ml) and extracted with ethyl acetate (2×10 ml). The organic layer was dried over sodium sulfate, filtered and evaporated and the residue was purified by flash chromatography (Biotage system) on silica gel using a SNAP 10 g as column and dichloromethane/methanol from 99:1 to 90:10 as eluents affording the title compound (8 mg) as a light brown solid.

¹H-NMR (400 MHz, DMSO-d₆) δ ppm: 11.80 (s, 1H), 8.77 (s, 2H), 6.95 (d, 1H), 6.54 (d, 1H), 4.45 (s, 2H), 2.15 (s, 3H), 2.11 (s, 3H), 1.04-1.08 (m, 2H), 0.88-0.92 (m, 2H).

LC/MS: QC_3_MIN: Rt=1.820 min; 352 [M+H]+.

Example 17

5-methyl-4-(4-{[4-methyl-3-(methyloxy)phenyl]oxy}phenyl)-2,4-dihydro-3H-1,2,4-triazol-3-one

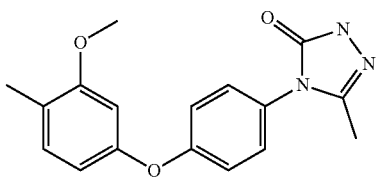 [SMILES: COc1cc(Oc2ccc(-n3c(C)n[nH]c3=O)cc2)ccc1C]

To a solution of 4-{[4-methyl-3-(methyloxy)phenyl]oxy}aniline (Intermediate 11, 336 mg, 1.467 mmol) in DCM (50 mL) Triethylamine (296 mg, 2.93 mmol) was added followed by triphosgene (174 mg, 0.587 mmol). The reaction mixture was stirred at room temperature for 0.5 h. Triethylamine (296 mg, 2.93 mmol) and acetohydrazide (130 mg, 1.76 mmol) were then added and the reaction mixture was stirred at room temperature overnight. The solvent was concentrated in vacuum and the residue was dissolved in a 2M aqueous solution of NaOH (15 mL) and the mixture was heated to reflux for 12 h. The reaction mixture was neutralized with aqueous 6M HCl to pH=7 and extracted with DCM (3×50 mL). The combined organic phases were dried over Na₂SO₄ and concentrated under reduced pressure to give the crude product which was purified by flash chromatography on silica gel using dichloromethane/methanol as eluents from 100/1 to 50/1 to yield 150 mg of the title compound.

MS_1 (ESI) m/z calcd for C₁₇H₁₇N₃O₃ 311.34, found 312.0 (MH+).

¹H-NMR (400 MHz; CDCl₃): δ ppm 7.22-7.26 (2H, m), 7.09-7.12 (3H, m), 6.55-6.56 (2H, m), 3.802 (3H, s), 2.15 (3H, s), 2.21 (3H, s).

The following compounds were prepared using the foregoing methodology, replacing 4-{[4-methyl-3-(methyloxy)phenyl]oxy}aniline (Intermediate 11) with the appropriate aniline as described in the foregoing Reaction Schemes. Final products were purified by flash-chromatography (Silica cartridge; Cyclohexane/EtOAc, dichloromethane/methanol or other appropriate solvent system).

| Ex | Structure | Name | Aniline | NMR characterization | Mass |
|---|---|---|---|---|---|
| 18 | 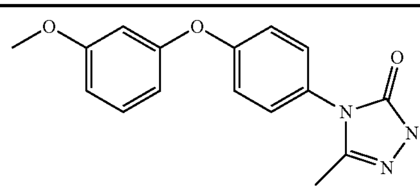 | 5-methyl-4-(4-{[3-(methyloxy)phenyl]oxy}phenyl)-2,4-dihydro-3H-1,2,4-triazol-3-one | 4-{[3-(methyloxy)phenyl]oxy}aniline | ¹HNMR (400 MHz, DMSO-d₆): δ ppm 11.59 (1H, s), 7.30-7.42 (3H, m), 7.09-7.12 (2H, m), 6.60-6.79 (3H, m), 3.75 (3H, s), 2.04 (3H, s). | MS_1 (ESI) m/z calcd for C₁₆H₁₅N₃O₃ 297.11, found 298.1 (MH⁺). |
| 19 | 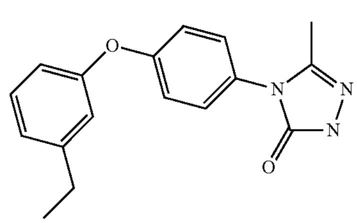 [SMILES: CCc1cccc(Oc2ccc(-n3c(C)n[nH]c3=O)cc2)c1] | 4-{4-[(3-ethylphenyl)oxy]phenyl}-5-methyl-2,4-dihydro-3H-1,2,4-triazol-3-one | 4-{[3-ethylphenyl]oxy}aniline (intermediate 12) | ¹HNMR (400 MHz, CDCl₃): δ ppm 10.00 (1H, br.s), 7.24-7.31 (3H, m), 7.01-7.10 (3H, m), 6.87-6.93 (2H, m), 2.63-2.68 (2H, q), 2.14 (3H, s) 1.22-1.26 (3H, t). | MS_1 (ESI) m/z calcd. For C₁₇H₁₇N₃O₂ 295.34, found 296 (MH⁺). |

| Ex | Structure | Name | Aniline | NMR characterization | Mass |
|---|---|---|---|---|---|
| 20 | 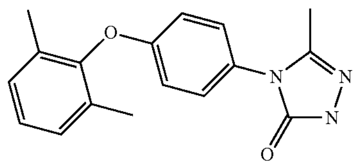 [SMILES: Cc1cccc(C)c1Oc1ccc(-n2c(C)n[nH]c2=O)cc1] | 4-{4-[(2,6-dimethylphenyl)oxy]phenyl}-5-methyl-2,4-dihydro-3H-1,2,4-triazol-3-one | 4-{[2,6-dimethylphenyl]oxy}aniline (intermediate 13) | ¹HNMR (400 MHz, CDCl₃): δ ppm 9.81 (1H, br.s), 7.07-7.20 (5H, m), 6.86-6.88 (2H, m), 2.13-2.14 (9H, d). | MS_1 (ESI) m/z calcd. For C₁₇H₁₇N₃O₂ 295.34, found 296 (MH⁺). |
| 21 | 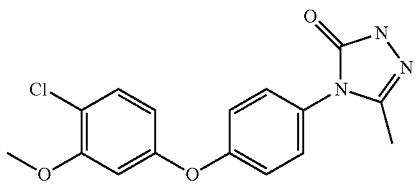 [SMILES: COc1cc(Oc2ccc(-n3c(C)n[nH]c3=O)cc2)ccc1Cl] | 4-(4-{[4-chloro-3-(methyloxy)phenyl]oxy}phenyl)-5-methyl-2,4-dihydro-3H-1,2,4-triazol-3-one | 4-{[4-chloro-3-(methyloxy)phenyl]oxy}aniline (intermediate 14) | ¹HNMR (400 MHz, DMSO-d₆): δ ppm 11.57 (1H, s), 7.04-7.45 (3H, t), 7.14-7.16 (2H, d), 6.97-6.98 (1H, S), 6.60-6.63 (1H, d), 3.85 (3H, s), 2.05 (3H, s). | Mass Spectrum (ESI) m/z calcd for C₁₆H₁₄ClN₃O₃ 331.75, found 332 (M + H⁺). |
| 22 | 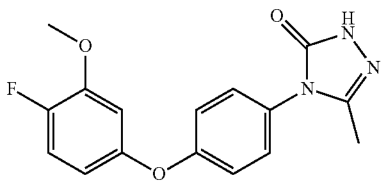 [SMILES: COc1cc(Oc2ccc(-n3c(C)n[nH]c3=O)cc2)ccc1F] | 4-(4-{[4-fluoro-3-(methyloxy)phenyl]oxy}phenyl)-5-methyl-2,4-dihydro-3H-1,2,4-triazol-3-one | 4-{[4-fluoro-3-(methyloxy)phenyl]oxy}aniline (intermediate 15) | ¹HNMR (400 MHz, CDCl₃): δ ppm 9.25-9.26 (1H, br.s), 7.25-7.27 (2H, m), 7.05-7.10 (3H, m), 6.72-6.74 (1H, m), 6.57-6.60 (1H, m), 3.87 (3H, s), 2.15 (3H, s). | MS_1 (ESI) m/z calcd for C₁₆H₁₄FN₃O₃ 315.3, found 316 (M + H⁺). |
| 23 | 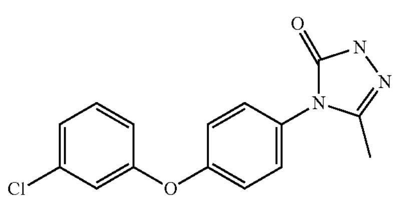 [SMILES: Cc1n[nH]c(=O)n1-c1ccc(Oc2cccc(Cl)c2)cc1] | 4-{4-[(3-chlorophenyl)oxy]phenyl}-5-methyl-2,4-dihydro-3H-1,2,4-triazol-3-one | 4-{[3-chlorophenyl]oxy}aniline (intermediate 16) | ¹HNMR (400 MHz, DMSO-d₆): δ ppm 11.62 (1H, s), 7.42-7.48 (3H, t), 7.26 (1H, d), 7.16-7.19 (4H, m), 2.06 (3H, s). | MS_1 (ESI) m/z calcd for C₁₅H₁₂ClN₃O₂ 301.73, found 302 (M + H⁺). |
| 24 | 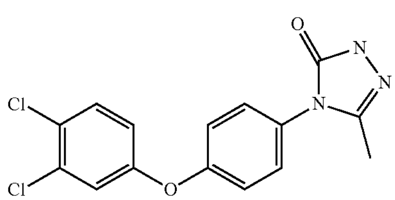 [SMILES: Cc1n[nH]c(=O)n1-c1ccc(Oc2ccc(Cl)c(Cl)c2)cc1] | 4-{4-[(3,4-dichlorophenyl)oxy]phenyl}-5-methyl-2,4-dihydro-3H-1,2,4-triazol-3-one | 4-{[3,4-dichlorophenyl]oxy}aniline (intermediate 17) | ¹HNMR (400 MHz, DMSO-d₆): δ ppm 11.62 (1H, s), 7.66-7.69 (1H, d), 7.41-7.47 (3H, d), 7.19-7.22 (2H, m), 7.11 (1H, d), 2.06 (3H, s). | MS_1 (ESI) m/z calcd for C₁₅H₁₁Cl₂N₃O₂ 336.17, found 336 (M + H⁺). |
| 25 | 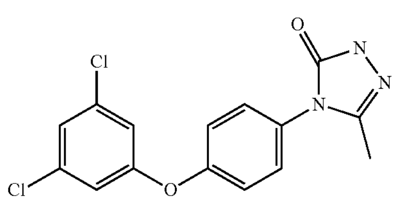 [SMILES: Cc1n[nH]c(=O)n1-c1ccc(Oc2cc(Cl)cc(Cl)c2)cc1] | 4-{4-[(3,5-dichlorophenyl)oxy]phenyl}-5-methyl-2,4-dihydro-3H-1,2,4-triazol-3-one | 4-{[3,5-dichlorophenyl]oxy}aniline (intermediate 18) | ¹HNMR (400 MHz, DMSO-d₆): δ ppm 11.63 (1H, s), 7.45-7.48 (3H, t), 7.22-7.25 (2H, d), 7.15-7.16 (2H, s), 2.07 (3H, s). | MS_1 (ESI) m/z calcd for C₁₅H₁₁Cl₂N₃O₂ 336.17, found 336 (M + H⁺). |
| 26 | 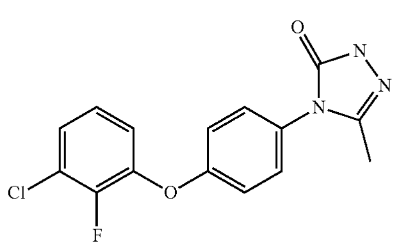 [SMILES: Cc1n[nH]c(=O)n1-c1ccc(Oc2cccc(Cl)c2F)cc1] | 4-{4-[(3-chloro-2-fluorophenyl)oxy]phenyl}-5-methyl-2,4-dihydro-3H-1,2,4-triazol-3-one | 4-{[3-chloro-2-fluorophenyl]oxy}aniline (intermediate 19) | ¹HNMR (400 MHz, DMSO-d₆): δ ppm 11.57 (1H, s), 7.41-7.48 (3H, t), 7.24-7.29 (2H, d), 7.14-7.17 (2H, d), 2.05 (3H, s). | MS_1 (ESI) m/z calcd for C₁₅H₁₁ClFN₃O₂ 319.72, found 320 (M + H⁺). |

| Ex | Structure | Name | Aniline | NMR characterization | Mass |
|---|---|---|---|---|---|
| 27 | 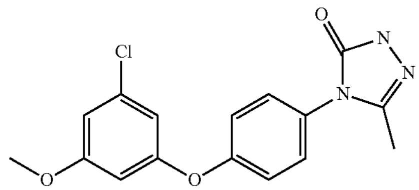 [SMILES: COc1cc(Cl)cc(Oc2ccc(-n3c(C)n[nH]c3=O)cc2)c1] | 4-(4-{[3-chloro-5-(methyloxy) phenyl]oxy} phenyl)-5-methyl-2,4-dihydro-3H-1,2,4-triazol-3-one | 4-{[5-chloro-3-(methyloxy) phenyl]oxy} aniline (intermediate 20) | $^1$HNMR (400 MHz, DMSO-$d_6$): δ ppm 11.58 (1H, s), 7.43-7.45 (2H, d), 7.17-7.20 (2H, d), 6.86 (1H, s), 6.64-6.68 (2H, d), 3.78 (3H, s), 2.06 (3H, s). | Mass Spectrum (ESI) m/z calcd for $C_{16}H_{14}ClN_3O_3$ 331.75, found 332 (M + H$^+$). |

Example 28

5-methyl-4-[4-({3-[(trifluoromethyl)oxy] phenyl}oxy)phenyl]-2,4-dihydro-3H-1,2,4-triazol-3-one

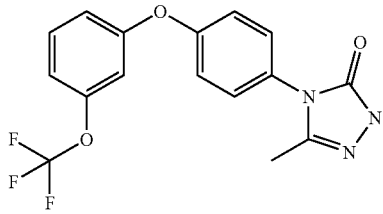 [SMILES: Cc1n[nH]c(=O)n1-c1ccc(Oc2cccc(OC(F)(F)F)c2)cc1]

To a solution of 3-trifluoromethoxy phenol (1.78 g, 10 mmol) and 1-fluoro-4-nitrobezene (1.41 g, 10 mmol) in CH$_3$CN (40 mL) K$_2$CO$_3$ (2.76 g, 20 mmol) was added and the reaction mixture was heated to reflux for 4 hrs. After filtration, the solvent was removed and the residue was washed with n-hexane (2×15 mL) and dried to afford 2.83 g of nitro intermediate. To a solution of nitro intermediate in THF (40 mL) and water (10 mL) Iron (11.20 g, 200 mmol) and then NH4Cl (10.70 g, 200 mmol) were added and the reaction mixture was heated to reflux for 4 hrs. After filtration, the solvent was concentrated and the residue poured into 50 mL of water. The mixture was extracted with ethyl acetate (3×50 mL) and the combined organic phases were dried over MgSO$_4$. Removal of solvent afforded 2.58 g of the aniline intermediate. 269 mg of the obtained aniline intermediate were dissolved in DCM (20 mL), Triethylamine (202 mg, 2 mmol) and then triphosgene (118.4 mg, 0.4 mmol) were added and the reaction mixture was stirred at room temperature for 4 hrs. Triethylamine (202 mg, 2 mmol) and acetohydrazide (74 mg, 1 mmol) were added to the above solution and the reaction mixture was stirred at room temperature overnight. Removal of solvent afforded crude material, which was purified by flash chromatography on silica gel using dichloromethane/methanol 200:1 as eluents to give 288 mg of urea intermediate. It was dissolved in an aqueous 2M solution of NaOH (15 mL) and the reaction mixture was heated to reflux for 12 hrs. The mixture was neutralized with aqueous 6N HCl and extracted with DCM (3×50 mL). The organic layer was dried over Na$_2$SO$_4$ and concentrated under reduced pressure to give crude compound. which was purified by flash chromatography on silica gel using dichloromethane/methanol 100:1 as eluents to afford 35 mg of title compound as white solid.

MS_1 (ESI) m/z calcd for C16H12F$_3$N$_3$O$_3$ 351.28, found 352.1 (MH$^+$).

$^1$HNMR (400 MHz, DMSO-$d_6$): δ ppm 11.60 (1H, s), 7.58-7.45 (3H, m), 7.22-7.08 (5H, m), 2.06 (3H, s).

The following compounds were prepared using the foregoing methodology, replacing 3-trifluoromethoxy phenol with the appropriate phenol as described in the foregoing Reaction Schemes. Final products were purified by flash-chromatography (Silica cartridge; Cyclohexane/EtOAc, dichloromethane/methanol or other appropriate solvent system).

| Ex | Structure | Name | Phenol | NMR characterization | Mass |
|---|---|---|---|---|---|
| 29 | 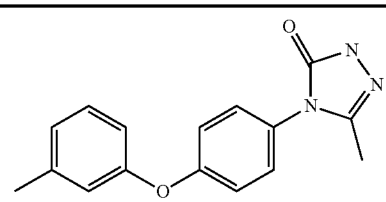 | 4-{4-[(3-methylphenyl) oxy]phenyl}-5-methyl-2,4-dihydro-3H-1,2,4-triazol-3-one | 3-methylphenol | $^1$HNMR (400 MHz, DMSO-$d_6$): δ ppm 11.57 (1H, s), 7.38-7.41 (2H, t), 7.29-7.31 (1H, d), 7.03-7.10 (3H, m), 6.92 (2H, d), 2.32 (3H, s), 2.05 (3H, s). | MS_1 (ESI) m/z calcd for $C_{16}H_{15}N_3O_2$ 281.31, found 282 (M + H$^+$). |
| 30 | 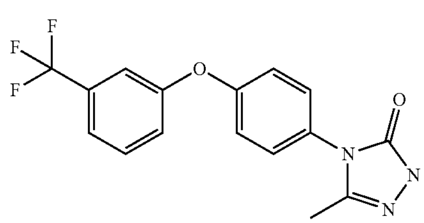 [SMILES: Cc1n[nH]c(=O)n1-c1ccc(Oc2cccc(C(F)(F)F)c2)cc1] | 5-methyl-4-(4-{[3-(trifluoromethyl) phenyl]oxy} phenyl)-2,4-dihydro-3H-1,2,4-triazol-3-one | 3-trifluoromethylphenol | $^1$HNMR (400 MHz, MeOD) δ ppm 7.61-7.59 (1H, m), 7.48-7.40 (3H, m), 7.33-7.30 (2H, m), 7.23-7.19 (2H, m), 2.14 (3H, s). | |

| Ex | Structure | Name | Phenol | NMR characterization | Mass |
|---|---|---|---|---|---|
| 31 | 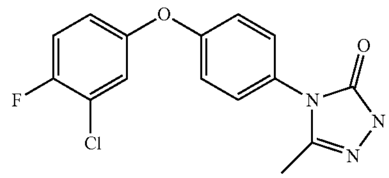 [SMILES: Cc1n[nH]c(=O)n1-c1ccc(Oc2ccc(F)c(Cl)c2)cc1] | 4-{4-[(3-chloro-4-fluorophenyl)oxy]phenyl}-5-methyl-2,4-dihydro-3H-1,2,4-triazol-3-one | 3-chloro-4-fluorophenol | $^1$HNMR (400 MHz, DMSO-d$_6$): δ ppm 11.60 (1H, s), 7.52-7.40 (4H, m), 7.15-7.12 (3H, m), 2.05 (3H, s). | MS_1 (ESI) m/z calcd for C$_{15}$H$_{11}$ClFN$_3$O$_2$ 319.72, found 320 (MH$^+$). |
| 32 | 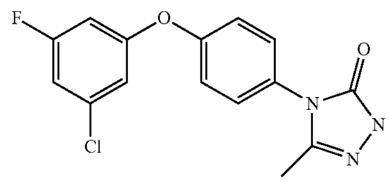 [SMILES: Cc1n[nH]c(=O)n1-c1ccc(Oc2cc(F)cc(Cl)c2)cc1] | 4-{4-[(3-chloro-5-fluorophenyl)oxy]phenyl}-5-methyl-2,4-dihydro-3H-1,2,4-triazol-3-one | 3-chloro-5-fluorophenol | $^1$HNMR (400 MHz, DMSO-d$_6$): δ ppm 11.62 (1H, s), 7.47-7.49 (2H, d), 7.24-7.26 (3H, d), 6.99-7.01 (2H, d), 2.08 (3H, s). | MS_1 (ESI) m/z calcd for C$_{15}$H$_{11}$ClFN$_3$O$_2$ 319.72, found 320 (MH$^+$). |

Example 33

4-{4-[(2,3-dimethylphenyl)oxy]phenyl}-5-methyl-2,4-dihydro-3H-1,2,4-triazol-3-one

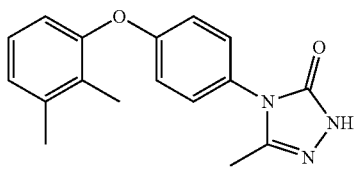 [SMILES: Cc1cccc(Oc2ccc(-n3c(C)n[nH]c3=O)cc2)c1C]

In a 8 mL vial 4-[(2,3-dimethylphenyl)oxy]aniline (150 mg, 0.654 mmol) and methyl (2E-2Z mixture)-2-[1-(methyloxy)ethylidene]hydrazinecarboxylate (Intermediate 21, 154 mg, 1.055 mmol) were dissolved in Methanol (2 mL) to give a colourless solution. The reaction mixture was shaked on PLS at 100° C. for 16 h. The solvent was removed under reduced pressure and the residue was purified by preparative HPLC to afford 96.9 mg of the title compound.

$^1$HNMR (400 MHz, DMSO-d$_6$): δ ppm 11.56 (br.s., 1H), 7.31-7.38 (m, 2H), 7.16 (t, 1H), 7.05-7.11 (m, 1H), 6.90-6.98 (m, 2H), 6.86 (d, 1H), 2.30 (s, 3H), 2.09 (s, 3H), 2.03 (s, 3H).

MS_1 (ESI) m/z calcd for C$_{17}$H$_{17}$N$_3$O$_2$ 295, found 296 (MH+).

The following compounds were prepared using the foregoing methodology, replacing 4-[(2,3-dimethylphenyl)oxy]aniline with the appropriate aniline (commercially available or synthesized using a similar procedure described for Intermediates 11-19) as described in the foregoing Reaction Schemes. For same compounds the reaction was performed in presence of Sodium methoxide (1-3 equivalents). Final products were purified by flash-chromatography (Silica cartridge; Cyclohexane/EtOAc, dichloromethane/methanol or other appropriate solvent system) or preparative HPLC.

| Ex | Structure | Name | Aniline | NMR characterization | Mass |
|---|---|---|---|---|---|
| 34 | 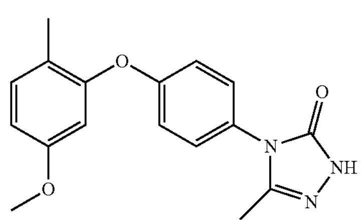 [SMILES: COc1ccc(C)c(Oc2ccc(-n3c(C)n[nH]c3=O)cc2)c1] | 5-methyl-4-(4-{[2-methyl-5-(methyloxy)phenyl]oxy}phenyl)-2,4-dihydro-3H-1,2,4-triazol-3-one | 4-{[6-methyl-3-(methyloxy)phenyl]oxy}aniline | $^1$HNMR (400 MHz, CDCl3) δ ppm 9.27 (1H, s), 7.21 (2 H, m), 7.18 (1 H, d), 7.01 (2H, m), 6.72 (1H, dd), 6.56 (1H, d), 3.76 (3 H, s), 2.14 (6 H, s) | MS_1 (ESI) m/z calcd for C$_{17}$H$_{17}$N$_3$O$_3$ 311, found 312 (MH$^+$). |
| 35 | 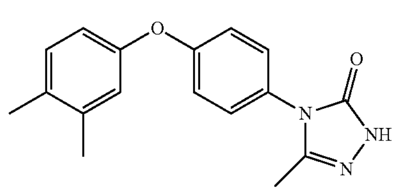 [SMILES: Cc1ccc(Oc2ccc(-n3c(C)n[nH]c3=O)cc2)cc1C] | 4-{4-[(3,4-dimethylphenyl)oxy]phenyl}-5-methyl-2,4-dihydro-3H-1,2,4-triazol-3-one | 4-[(3,4-dimethylphenyl)oxy]aniline | $^1$HNMR (400 MHz, CDCl3) δ ppm 10.57 (1H, bs), 7.24 (2 H, d), 7.15 (1 H, d), 7.07 (2H, d), 6.89 (1H, s), 6.83 (1H, d), 2.27 (6 H, s), 2.15 (3 H, s) | MS_1 (ESI) m/z calcd for C$_{17}$H$_{17}$N$_3$O$_2$ 295, found 296 (MH$^+$). |

-continued

| Ex | Structure | Name | Aniline | NMR characterization | Mass |
|---|---|---|---|---|---|
| 36 | 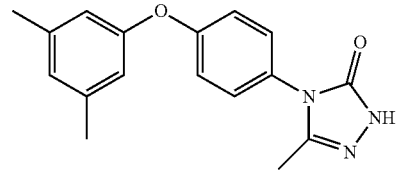 [SMILES: Cc1cc(C)cc(Oc2ccc(-n3c(C)n[nH]c3=O)cc2)c1] | 4-{4-[(3,5-dimethylphenyl)oxy]phenyl}-5-methyl-2,4-dihydro-3H-1,2,4-triazol-3-one | 4-[(3,5-dimethylphenyl)oxy]aniline | $^1$HNMR (400 MHz, MeOD) δ ppm 7.33 (2 H, d), 7.09 (2 H, d), 6.84 (1H, s), 6.68 (2H, s), 2.29 (6 H, s), 2.13 (3 H, s) | MS_1 (ESI) m/z calcd for $C_{17}H_{17}N_3O_2$ 295, found 296 (MH$^+$). |
| 37 | 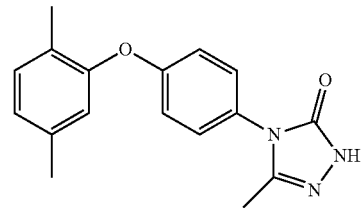 [SMILES: Cc1ccc(C)c(Oc2ccc(-n3c(C)n[nH]c3=O)cc2)c1] | 4-{4-[(2,5-dimethylphenyl)oxy]phenyl}-5-methyl-2,4-dihydro-3H-1,2,4-triazol-3-one | 4-[(2,5-dimethylphenyl)oxy]aniline | | MS_1 (ESI) m/z calcd for $C_{17}H_{17}N_3O_2$ 295, found 296 (MH$^+$). |
| 38 | 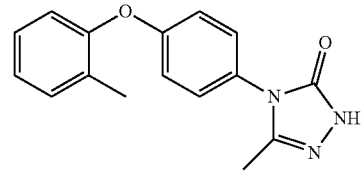 [SMILES: Cc1ccccc1Oc1ccc(-n2c(C)n[nH]c2=O)cc1] | 5-methyl-4-{4-[(2-methylphenyl)oxy]phenyl}-2,4-dihydro-3H-1,2,4-triazol-3-one | 4-[(2-methylphenyl)oxy]aniline | $^1$HNMR (400 MHz, CDCl3) δ ppm 8.92 (br. s., 1 H), 7.29-7.33 (m, 1 H), 7.20-7.26 (m, 3 H), 7.15 (dt, 1 H), 6.97-7.04 (m, 3 H), 2.25 (s, 3 H), 2.16 (s, 3 H). | MS_1 (ESI) m/z calcd for $C_{16}H_{15}N_3O_2$ 281, found 282 (MH$^+$). |
| 39 | 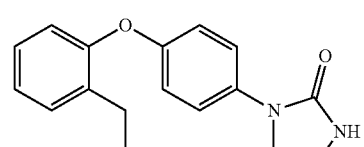 | 4-{4-[(2-ethylphenyl)oxy]phenyl}-5-methyl-2,4-dihydro-3H-1,2,4-triazol-3-one | 4-[(2-ethylphenyl)oxy]aniline | $^1$HNMR (400 MHz, DMSO-d6) δ ppm 11.57 (s, 1 H), 7.35-7.44 (m, 3 H), 7.25-7.33 (m, 1 H), 7.19-7.24 (m, 1 H), 6.95-7.07 (m, 3 H), 2.60 (q, 2 H), 2.06 (s, 3 H), 1.16 (t, 3 H). | MS_1 (ESI) m/z calcd for $C_{17}H_{17}N_3O_2$ 295, found 296 (MH$^+$). |
| 40 | 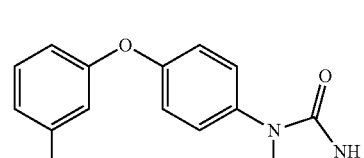 | 5-methyl-4-(4-{[3-(1-methylethyl)phenyl]oxy}phenyl)-2,4-dihydro-3H-1,2,4-triazol-3-one | 4-[(3-isopropylphenyl)oxy]aniline | $^1$HNMR (400 MHz, CDCl3) δ ppm 9.41 (1H, br-s), 7.33-7.24 (3H, m), 7.11-7.07 (3 H, m), 6.97 (1H, t), 6.89 (1H, dd), 2.92 (1H, m), 2.16 (3H, s), 1.27 (3 H, s), 1.26 (3H, s) | MS_1 (ESI) m/z calcd for $C_{18}H_{19}N_3O_2$ 309, found 310 (MH$^+$). |
| 41 | 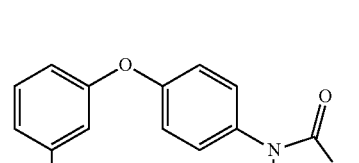 | 4-(4-{[3-(dimethylamino)phenyl]oxy}phenyl)-5-methyl-2,4-dihydro-3H-1,2,4-triazol-3-one | 4-{[3(N,N-dimethyl)phenyl]oxy}aniline | $^1$HNMR (400 MHz, CDCl3) δ ppm 7.22-7.32 (3H, m), 7.15 (2H, d), 6.60 (1H, d), 6.50 (1H, s), 6.45 (1H, d), 3.01 (6H, s), 2.19 (3H, s). | MS_1 (ESI) m/z calcd for $C_{17}H_{18}N_4O_2$ 310, found 311 (MH$^+$). |
| 42 | 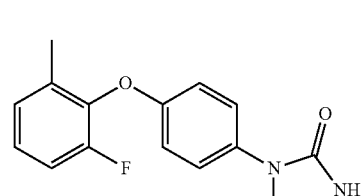 | 4-{4-[(2-fluoro-6-methylphenyl)oxy]phenyl}-5-methyl-2,4-dihydro-3H-1,2,4-triazol-3-one | 4-[(2-methyl-6-fluorophenyl)oxy]aniline | $^1$HNMR (400 MHz, MeOD) δ ppm 7.33-7.38 (m, 2H), 7.10-7.26 (m, 6 H), 6.99-7.04 (m, 2 H), 2.26 (s, 3 H), 2.14 (s, 3 H). | MS_1 (ESI) m/z calcd for $C_{16}H_{14}FN_3O_2$ 299, found 300 (MH$^+$). |

| Ex | Structure | Name | Aniline | NMR characterization | Mass |
|---|---|---|---|---|---|
| 43 | 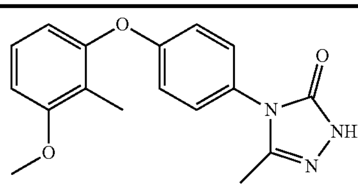 | 5-methyl-4-(4-{[2-methyl-3-(methyloxy)phenyl]oxy}phenyl)-2,4-dihydro-3H-1,2,4-triazol-3-one | 2-methyl-3-methoxyphenol | $^1$HNMR (400 MHz, CDCl3) δ ppm 9.20 (1 H, s), 7.09-7.23 (3 H, m), 6.94-7.04 (2 H, m), 6.73 (1 H, d), 6.63 (1 H, d), 3.87 (3 H, s), 2.13 (3 H, s), 2.10 (3 H, s). | MS_1 (ESI) m/z calcd for $C_{17}H_{17}N_3O_3$ 311, found 312 (MH$^+$). |

Example 44

4-(4-{[3-(ethyloxy)phenyl]oxy}phenyl)-5-methyl-2,4-dihydro-3H-1,2,4-triazol-3-one

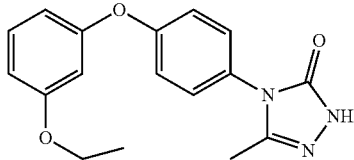 [SMILES: CCOc1cccc(Oc2ccc(-n3c(C)n[nH]c3=O)cc2)c1]

To cesium carbonate (641 mg, 1.968 mmol, 2 equiv) was added 3-ethoxyphenol (272 mg, 1.968 mmol, 2 equiv) in 4 mL of NMP. The reaction mixture was degassed and filled with nitrogen 3 times (3 cycles vacuum/nitrogen). 4-(4-bromophenyl)-5-methyl-2,4-dihydro-3H-1,2,4-triazol-3-one (Intermediate 22, 250 mg, 0.984 mg, 1 equiv), 2,2,6,6-tetramethyl-3,5-heptanedione (18 mg, 0.098 mmol, 0.1 equiv) and copper chloride (58 mg, 0.590 mmol, 0.6 equiv) were added. The reaction mixture was degassed and filled with nitrogen 3 times (3 cycles vacuum/nitrogen) and then warmed to 120 C under nitrogen overnight. The reaction mixture was diluted with dichloromethane and filtered. Volatiles were removed in vacuo and the residue was purified by preparative HPLC to give the title compound (20.2 mg).

$^1$HNMR (400 MHz, MeOD): δ ppm 7.33-7.38 (2H, m), 7.23-7.30 (1H, m), 7.10-7.16 (2H, m), 6.68-6.75 (1H, m), 6.55-6.65 (2H, m), 4.01 (2H, q), 2.12 (3H, s), 1.37 (3H, t).

MS_1 (ESI) m/z calcd for $C_{17}H_{17}N_3O_3$ 311, found 312 (MH$^+$).

Example 45

4-{4-[(3-methylphenyl)oxy]phenyl}-2,4-dihydro-3H1,2,4-triazol-3-one

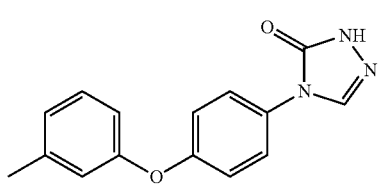 [SMILES: Cc1cccc(Oc2ccc(-n3cn[nH]c3=O)cc2)c1]

Example 46

4-(4-{[3-trifluoromethyl)phenyl]oxy}phenyl)-2,4-dihydro-3H-1,2,4-triazol-3-one

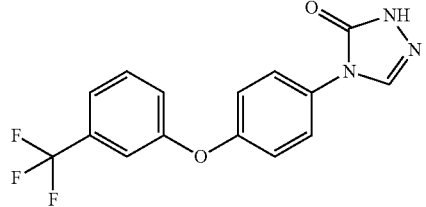 [SMILES: O=c1[nH]ncn1-c1ccc(Oc2cccc(C(F)(F)F)c2)cc1]

Example 47

4-[4-[4-fluoro-3-(trifluoromethoxy)phenoxy]phenyl]-3-methyl-1H-1,2,4-triazol-5-one

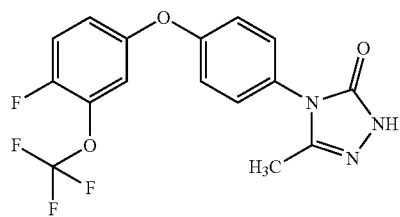 [SMILES: Cc1n[nH]c(=O)n1-c1ccc(Oc2ccc(F)c(OC(F)(F)F)c2)cc1]

methyl (2E/Z)-2-(1-ethoxyethylidene)hydrazinecarboxylate (Intermediate 6, 26.768 mg, 0.1671 mmol) and 4-[4-fluoro-3-(trifluoromethoxy)phenoxy]aniline (Intermediate 23, 40 mg, 0.1393 mmol) were dissolved in Ethanol (2 mL). The solution was heated to 110° C. to evaporate the solvent. The resulting slurry was mechanically stirred at 110° C. overnight. After this time the reaction was stopped and the resulting crude was purified through a Biotage KP-Sil cartridge (10 g) using DCM/MeOH as eluent mix (from 0.5% to 10% of MeOH for 12 CV). Fractions of interest were collected and dried in vacuo to afford the title compound (17 mg).

LC/MS: QC_3_MIN: Rt=2.337 min; 370 [M+H]+.

Example 48

5-methyl-4-(5-methyl-6-{[3-(1-methylethyl)phenyl]oxy}-3-pyridinyl)-2,4-dihydro-3H-1,2,4-triazol-3-one

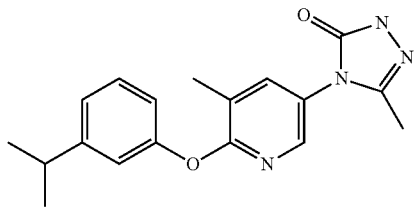 [SMILES: Cc1cc(-n2c(C)n[nH]c2=O)cnc1Oc1cccc(C(C)C)c1]

A mixture of methyl carbazate (372 mg, 4.13 mmol) and p-toluenesulfonic acid monohydrate (16 mg, 0.083 mmol) in methanol (12 mL) was purged with $N_2$ and trimethyl orthoacetate (496 mg, 4.12 mmol) was added. The mixture was stirred at 60° C. for 4 hrs and $NaHCO_3$ (7 mg, 0.083 mmol) was added. The solid was filtered off and the filtrate was evaporated to afford an intermediate, which was mixed with 5-amino-3-methyl-2-{[3-(2-methylethyl)phenyl]oxy}-pyridine (Intermediate 26, 200 mg, 0.83 mmol) and heated to 110° C. in a vial for 5 days. The solvent was removed under reduced pressure and the residue was purified by silica gel chromatography (petroleum ether/ethyl acetate from 1:1 to 1:2) to afford the title compound (30 mg) as a grey solid.

MS_1 (ESI) m/z calcd. For $C_{18}H_{20}N_4O_2$ 324.39, found 325 (M+H+).

$^1$H-NMR (400 MHz, $CDCl_3$): δ ppm 9.42-9.47 (br.s, 1H), 7.90-7.91 (d, 1H), 7.54-7.55 (d, 1H), 7.32-7.36 (m, 1H), 6.95-7.12 (m, 3H), 2.92-2.96 (t, 1H), 2.42 (s, 3H), 2.14 (s, 3H), 1.26-1.28 (d, 6H).

Example 49

4-(6-{[3-(ethyloxy)phenyl]oxy}-5-methyl-3-pyridinyl)-5-methyl-2,4-dihydro-3H-1,2,4-triazol-3-one

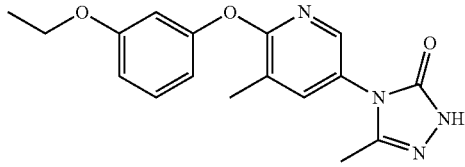 [SMILES: CCOc1cccc(Oc2ncc(-n3c(C)n[nH]c3=O)cc2C)c1]

The title compound was prepared in a similar way with respect to Example 48 replacing the 5-amino-3-methyl-2-{[3-(2-methylethyl)phenyl]oxy}-pyridine (Intermediate 26) with the 5-amino-3-methyl-2-{[3-(ethyloxy)phenyl]oxy}-pyridine (Intermediate 27). The title compound, 80 mg as a white solid, was obtained by flash-chromatography (Silica cartridge; petroleum ether/ethyl acetate 1:1).

MS_1 (ESI) m/z calcd. For $C_{17}H_{18}N_4O_3$ 326.14, found 327.2 (M+H+).

1HNMR (400 MHz, DMSO-d6): δ ppm 11.65 (s, 1H), 8.00 (d, 1H), 7.82 (d, 1H), 7.28-7.32 (t, 1H), 6.69-6.80 (m, 3H), 3.99-4.05 (q, 2H), 2.34 (s, 3H), 2.06 (s, 3H), 1.30-1.33 (t, 3H).

Example 50

4-{6-[(2,3-dimethylphenyl)oxy]-3-pyridinyl}-5methyl-2,4-dihydro-3H-1,2,4-triazol-3-one

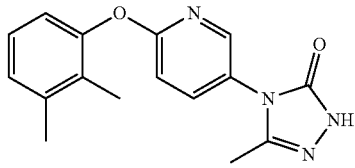 [SMILES: Cc1cccc(Oc2ccc(-n3c(C)n[nH]c3=O)cn2)c1C]

In a 8 mL vial 6-[(2,3-dimethylphenyl)oxy]-3-pyridinamine (100 mg, 0.467 mmol) and methyl (2E/Z)-2-[1-(methyloxy)ethylidene]hydrazinecarboxylate (Intermediate 21, 171 mg, 1.167 mmol) were dissolved in Methanol (2 mL) to give a pale yellow solution. The reaction mixture was shaked at 100° C. for 20 hours. Volatiles were removed under reduced pressure and the residue was purified by preparative HPLC to give the title compound (51.1 mg) as white solid.

MS_1 (ESI) m/z calcd. For $C_{16}H_{16}N_4O_2$ 296, found 297 (M+H+).

1H NMR (400 MHz, $CDCl_3$): δ ppm 9.64 (br. s., 1H), 8.14 (d, 1H), 7.72 (dd, 1H), 7.19 (t, 1H), 7.09-7.14 (m, 1H), 7.05 (d, 1H), 6.97 (d, 1H), 2.37 (s, 3H), 2.19 (s, 3H), 2.14 (s, 3H).

Example 51

4-(6-{[3-(1-methylethyl)phenyl]oxy}-3-pyridinyl)-2,4-dihydro-3H-1,2,4-triazol-3-one

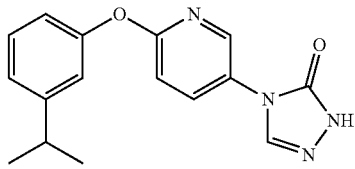 [SMILES: CC(C)c1cccc(Oc2ccc(-n3cn[nH]c3=O)cn2)c1]

The title compound was prepared in a similar way with respect to Example 50 replacing 6-[(2,3-dimethylphenyl)oxy]-3-pyridinamine with 6-{[3-(1-methylethyl)phenyl]oxy}-3-pyridinamine and methyl (2E/Z)-2-(1-methoxyethylidene)hydrazinecarboxylate (Intermediate 21) with methyl-2-[1-(methyloxy)methylidene]hydrazinecarboxylate (Intermediate 28). The title compound, 21 mg, was obtained by preparative HPLC.

MS_1 (ESI) m/z calcd. For $C_{16}H_{16}N_4O_2$ 296, found 297 (M+H+).

1H NMR (400 MHz, $CDCl_3$): δ ppm 9.25 (1H, s), 8.28 (1H, d), 7.95 (1H, dd), 7.65 (1H, s), 7.34 (1H, t), 7.11 (1H, d), 6.90-7.06 (3H, m), 2.82-3.06 (1H, m), 1.27 (3H, s), 1.26 (3H, s).

Example 52

5-methyl-4-(6-{[3-(1-methylethyl)phenyl]oxy}-3-pyridinyl)-2,4-dihydro-3H-1,2,4-triazol-3-one

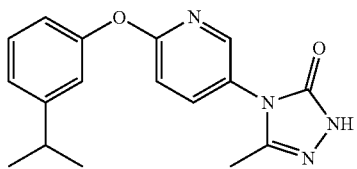 [SMILES: Cc1n[nH]c(=O)n1-c1ccc(Oc2cccc(C(C)C)c2)nc1]

Example 53

4-(6-{[2-(1,1-dimethylethyl)phenyl]oxy}-3-pyridinyl)-5-methyl-2,4,dihydro-3H-1,2,4trazol-3-one

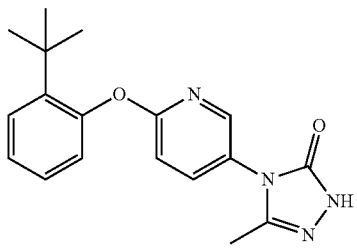 [SMILES: Cc1n[nH]c(=O)n1-c1ccc(Oc2ccccc2C(C)(C)C)nc1]

The title compound was prepared in a similar way with respect to Example 50 replacing 6-[(2,3-dimethylphenyl)oxy]-3-pyridinamine with 6-{[2-(1,1-dimethylethyl)phenyl]oxy}-3-pyridinamine. The title compound, 4.2 mg, was obtained by preparative HPLC.

MS_1 (ESI) m/z calcd. For $C_{18}H_{20}N_4O_2$ 324, found 325 (M+H+).

1H NMR (400 MHz, CDCl3): δ ppm 9.51 (1H, br.s), 8.18 (1H, d), 7.73 (1H, dd), 7.48 (1H, dd), 7.25 (1H, dd), 7.20 (1H, dt), 7.07 (1H, d), 7.01 (1H, dd), 2.20 (3H, s), 1.40 (9H, s).

Example 54

5-methyl-4-{6-[4-methyl-3-(trifluoromethoxy)phenoxy]pyridin-3-yl}-2,4-dihydro-3H-1,2,4-triazol-3-one

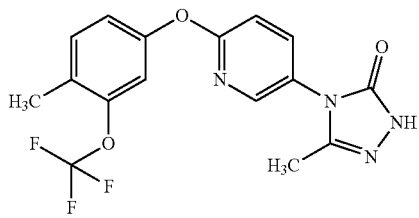 [SMILES: Cc1ccc(Oc2ccc(-n3c(C)n[nH]c3=O)cn2)cc1OC(F)(F)F]

To a solution of methyl-2-[1-({6-[4-methyl-3-(trifluoromethoxy)phenoxy]pyridin-3-yl}amino)ethylidene]hydrazinecarboxylate (Intermediate 33, 360 mg, 0.90 mmol) in 3 mL of acetonitrile and some drops of water, potassium carbonate (187 mg) was added. The resulting solution was stirred at room temperature for 24 hrs until complete conversion. The mixture was diluted with water (5 mL) and ethyl acetate (5 mL) and phases were separated. The aqueous phase was back-extracted with ethyl acetate (2×20 mL). The combined organics were dried over Na2SO4, filtered and concentrated to give 280 mg as pale orange foam. This material was dissolved in MTBE (1 mL) and n-heptane was added until a solid precipitated. This was collected by filtration to give 234 mg of the title compound as white solid.

$^1$H-NMR (400 MHz, DMSO-$d_6$): δ ppm 11.66 (1H, br. s), 8.20 (1H, d), 7.96 (1H, dd), 7.44 (1H, d), 7.09-7.34 (3H, m), 2.28 (3H, s), 2.05 (3H, s). 19F-NMR (376 MHz, DMSO-$d_6$): δ ppm 56.54.

Biological Example 1

The ability of the compounds of the invention to modulate the voltage-gated potassium channel subtypes Kv3.2/3.1 may be determined using the following assay. The assay may also be used to determine the ability of compounds of the invention to modulate the voltage-gated potassium channel Kv3.3. Analogous methods may be used to investigate the ability of the compounds of the invention to modulate other channel subtypes.

Cell Biology

To assess compound effects on human Kv3.2 channels (hKv3.2), a stable cell line expressing human Kv3.2 channels (hKv3.2) was created by transfecting Chinese Hamster Ovary (CHO)—K1 cells with a pCIH5-hKv3.2 vector. Cells were cultured in DMEM/F12 medium supplemented by 10% Foetal Bovine Serum, 1× non-essential amino acids (Invitrogen) and 500 ug/ml of Hygromycin-B (Invitrogen). Cells were grown and maintained at 37° C. in a humidified environment containing 5% $CO_2$ in air.

To assess compound effects on human Kv3.1 channels (hKv3.1), CHO/Gam/E1A-clone22 alias CGE22 cells were transduced using a hKv3.1 BacMam reagent. This cell line was designed to be an improved CHO-K1-based host for enhanced recombinant protein expression as compared to wild type CHO-K1. The cell line was generated following the transduction of CHO-K1 cells with a BacMam virus expressing the Adenovirus-Gam1 protein and selection with Geneticin-G418, to generate a stable cell line, CHO/Gam-A3. CHO/Gam-A3 cells were transfected with pCDNA3-E1A-Hygro, followed by hygromycin-B selection and FACS sorting to obtain single-cell clones. BacMam-Luciferase and BacMam-GFP viruses were then used in transient transduction studies to select the clone based on highest BacMam transduction and recombinant protein expression. CGE22 cells were cultured in the same medium used for the hKv3.2 CHO-K1 stable cell line with the addition of 300 ug/ml hygromycin-B and 300 ug/ml G418. All other conditions were identical to those for hKv3.2 CHO-K1 cells. The day before an experiment 10 million CGE22 cells were plated in a T175 culture flask and the hKv3.1 BacMam reagent (pFBM/human Kv3.1) was added (MOI of 50). Transduced cells were used 24 hours later.

To assess compound effects on human Kv3.3 channels (hKv3.3), a stable cell line expressing human Kv3.3 channels was created by transfecting Chinese Hamster Ovary (CHO)—K1 cells with a pBacMire_KCNC-3 vector. Cells were cultured in DMEM/F12 (Gibco) supplemented with 10% Foetal Bovine Serum (Gibco), 1× non-essential amino acids (Invitrogen) and geneticin (G418) 400 microg/mL. Cells were grown and maintained at 37° C. in a humidified environment containing 5% $CO_2$ in air.

Cell Preparation for IonWorks Quattro™ Experiments

The day of the experiment, cells were removed from the incubator and the culture medium removed. Cells were washed with 5 ml of Dulbecco's PBS (DPBS) calcium and magnesium free and detached by the addition of 3 ml Versene (Invitrogen, Italy) followed by a brief incubation at 37° C. for 5 minutes. The flask was tapped to dislodge cells and 10 ml of DPBS containing calcium and magnesium was added to prepare a cell suspension. The cell suspension was then placed into a 15 ml centrifuge tube and centrifuged for 2 min at 1200 rpm. After centrifugation, the supernatant was removed and the cell pellet re-suspended in 4 ml of DPBS containing calcium and magnesium using a 5 ml pipette to break up the pellet. Cell suspension volume was then corrected to give a cell concentration for the assay of approximately 3 million cells per ml.

All the solutions added to the cells were pre-warmed to 37° C.

Electrophysiology

Experiments were conducted at room temperature using IonWorks Quattro™ planar array electrophysiology technology (Molecular Devices Corp.) with PatchPlate™ PPC. Stimulation protocols and data acquisition were carried out using a microcomputer (Dell Pentium 4). Planar electrode hole resistances (Rp) were determined by applying a 10 mV voltage step across each well. These measurements were performed before cell addition. After cell addition and seal formation, a seal test was performed by applying a voltage step from −80 mV to −70 mV for 160 ms. Following this, amphotericin-B solution was added to the intracellular face of the electrode to achieve intracellular access. Cells were held at −70 mV. Leak subtraction was conducted in all experiments by applying 50 ms hyperpolarizing (10 mV) prepulses to evoke leak currents followed by a 20 ms period at the holding potential before test pulses. For hKv3.2 and hKv3.1 assays, from the holding potential of −70 mV, a first test pulse to −15 mV was applied for 100 ms and following a further 100 ms at −70 mV, a second pulse to 40 mV was applied for 50 ms. Cells were then maintained for a further 100 ms at −100 mV and then a voltage ramp from −100 mV to 40 mV was applied over 200 ms. For hKv3.3 assays, from the holding potential of −70 mV, a first test pulse to 0 mV was applied for 500 ms and following a further 100 ms at −70 mV, a second pulse to 40 mV was applied for 200 ms. These longer test pulses were used to study inactivation of hKv3.3 channels. Test pulses protocol may be performed in the absence (pre-read) and presence (post-read) of the test compound. Pre- and post-reads may be separated by the compound addition followed by a 3 minute incubation.

Solutions and Drugs

The intracellular solution contained the following (in mM): K-gluconate 100, KCl 54, MgCl2 3.2, HEPES 5, adjusted to pH 7.3 with KOH. Amphotericin-B solution was prepared as 50 mg/ml stock solution in DMSO and diluted to a final working concentration of 0.1 mg/ml in intracellular solution. The external solution was Dulbecco's Phosphate Buffered Saline (DPBS) and contained the following (in mM): CaCl$_2$ 0.90, KCl 2.67, KH2PO4 1.47, MgCl.6H2O 0.493, NaCl 136.9, Na$_3$PO$_4$ 8.06, with a pH of 7.4.

Compounds of the invention (or reference compounds such as N-cyclohexyl-N-[(7,8-dimethyl-2-oxo-1,2-dihydro-3-quinolinyl)methyl]-N-phenylurea were dissolved in dimethylsulfoxide (DMSO) at a stock concentration of 10 mM. These solutions were further diluted with DMSO using a Biomek FX (Beckman Coulter) in a 384 compound plate. Each dilution (1 µL) was transferred to another compound plate and external solution containing 0.05% pluronic acid (66 µL) was added. 3.5 µL from each plate containing a compound of the invention was added and incubated with the cells during the IonWorks Quattro™ experiment. The final assay dilution was 200 and the final compound concentrations were in the range 50 µM to 50 nM.

Data Analysis

The recordings were analysed and filtered using both seal resistance (>20 MΩ) and peak current amplitude (>500 pA at the voltage step of 40 mV) in the absence of compound to eliminate unsuitable cells from further analysis. For hKv3.2 and hKv3.1 assays, paired comparisons of evoked currents between pre- and post-drug additions measured for the −15 mV voltage step were used to determine the positive modulation effect of each compound. Kv3 channel-mediated outward currents were measured determined from the mean amplitude of the current over the final 10 ms of the −15 mV voltage pulse minus the mean baseline current at −70 mV over a 10 ms period just prior to the −15 mV step. These Kv3 channel currents following addition of the test compound were then compared with the currents recorded prior to compound addition. Data were normalised to the maximum effect of the reference compound (50 microM of N-cyclohexyl-N-[(7,8-dimethyl-2-oxo-1,2-dihydro-3-quinolinyl) methyl]-N'-phenylurea) and to the effect of a vehicle control (0.5% DMSO). The normalised data were analysed using ActivityBase or Excel software. The concentration of compound required to increase currents by 50% of the maximum increase produced by the reference compound (EC50) was determined by fitting of the concentration-response data using a four parameter logistic function in ActivityBase. For hKv3.3 assays, paired comparisons of evoked currents between pre- and post-drug additions were measured for the 0 mV step, considering the peak current and the decay (inactivation) of the current over the duration of the 0 mv test pulse (500 ms).

N-cyclohexyl-N-[(7,8-dimethyl-2-oxo-1,2-dihydro-3-quinolinyl)methyl]-N-phenylurea was obtained from ASINEX (Registry Number: 552311-06-5).

All of the Example compounds were tested in the above hKv3.1 and hKv3.2 assay measuring potentiation of Kv3.1 or Kv3.2 or Kv3.1 and Kv 3.2 (herein after "Kv3.1 and/or Kv3.2"). Kv3.1 and/or Kv3.2 positive modulators produce in the above assay an increase of whole-cell currents of, on average, at least 20% of the increase observed with 50 microM N-cyclohexyl-N-[(7,8-dimethyl-2-oxo-1,2-dihydro-3-quinolinyl)methyl]-N-phenylurea. Thus, in the recombinant cell assays of Biological Example 1, all of the Example compounds act as positive modulators. As used herein, a Kv3.1 and/or Kv3.2 positive modulator is a compound which has been shown to produce at least 20% potentiation of whole-cell currents mediated by human Kv3.1 and/or human Kv3.2 channels recombinantly expressed in mammalian cells, as determined using the hKv3.1 and hKv3.2 assays described in Biological Example 1 (Biological Assays).

Example 14 was tested in the above hKv3.3 recombinant cell assay. Example 14 at 12.5 micromolar produced a mean 75% increase in human Kv3.3 peak current at 0 mV (n=2).

A secondary analysis of the data from the hKv3.1, hKv3.2 and hKv3.3 assays described in Biological Example 1 may be used to investigate the effect of the compounds on rate of rise of the current from the start of the depolarising voltage pulses. The magnitude of the effect of a compound can be determined from the time constant (Tau$_{act}$) obtained from a non-linear fit, using the equation given below, of the rise in Kv3.1, Kv3.2 or Kv 3.3 currents following the start of the −15 mV depolarising voltage pulse.

$$Y = (Y0 - Y\max)*\exp(-K*X) + Y\max$$

where:

Y0 is the current value at the start of the depolarising voltage pulse;

Ymax is the plateau current;

K is the rate constant, and Tau$_{act}$ is the activation time constant, which is the reciprocal of K.

Similarly, the effect of the compounds on the time taken for Kv3.1, Kv3.2 or Kv3.3 currents to decay on closing of the channels at the end of the −15 mV depolarising voltage pulses can also be investigated. In this latter case, the magnitude of the effect of a compound on channel closing can be determined from the time constant ($Tau_{deact}$) of a non-linear fit of the decay of the current ("tail current") immediately following the end of the depolarising voltage pulse.

Kv3.1, Kv3.2 and Kv3.3 channels must activate and deactivate very rapidly in order to allow neurons to fire actions potentials at high frequency (Rudy and McBain, 2001, Trends in Neurosciences 24, 517-526). Slowing of activation is likely to delay the onset of action potential repolarisation; slowing of deactivation could lead to hyperpolarising currents that reduce the excitability of the neuron and delay the time before the neuron can fire a further action potential. Together these two slowing effects on channel activation and deactivation are likely to lead to a reduction rather than a facilitation of the neurons ability to fire at high frequencies. Thus compounds that have this slowing effect on the Kv3.1 and/or Kv3.2 and/or Kv3.3 channels will effectively behave as negative modulators of the channels, leading to a slowing of neuronal firing. This latter effect has been shown for certain of the compounds disclosed in WO2011/069951, where marked increases in $Tauac_t$ can be observed from recordings made from "fast-firing" interneurons in the cortex of rat brain, using electrophysiological techniques, in vitro. The addition of the relevant compounds reduces the ability of the neurons to fire in response to trains of depolarising pulses at 300 Hz.

Therefore, although compounds of the invention may be identified act as positive modulators in the recombinant cell assay of Biological Example 1, those compounds which markedly increase the value of $Tau_{act}$ reduce the ability of neurons in native tissues to fire at high frequency.

Biological Example 2

Determination of Blood and Brain Tissue Binding
Materials and Methods

Rat whole blood, collected on the week of the experiment using K3-EDTA as an anti-coagulant, was diluted with isotonic phosphate buffer 1:1 (v/v). Rat whole brain, stored frozen at −20° C., was thawed and homogenised in artificial cerebrospinal fluid (CSF) 1:2 (w/v).

An appropriate amount of test compound was dissolved in DMSO to give a 5 millimolar solution. Further dilutions, to obtain a 166.7 micromolar working solution was then prepared using 50% acetonitrile in MilliQ water. This working solution was used to spike the blood to obtain a final concentration of 0.5 micromolar in whole blood. Similarly, the working solution was used to spike brain samples to obtain a final concentration of 5 micromolar in whole brain. From these spiked blood and brain preparations, control samples (n=3), were immediately extracted and used to calculate the initial recovery of the test items.

150 microL of compound-free buffer (isotonic phosphate buffer for blood or artificial CSF buffer for brain) was dispensed in one half-well and 150 microL of spiked matrix (blood or brain) was loaded in the other half-well, with the two halves separated by a semi-permeable membrane. After an equilibration period of 5 hours at 37° C., 50 microL of dialysed matrix (blood or brain) was added to 50 microL of corresponding compound-free buffer, and vice-versa for buffer, such that the volume of buffer to matrix (blood or brain) remained the same. Samples were then extracted by protein precipitation with 300 microL of acetonitrile containing rolipram (control for positive ionization mode) or diclofenac (control for negative ionization mode) as internal standards and centrifuged for 10 min at 2800 rpm. Supernatants were collected (100 microL), diluted with 18% ACN in MilliQ water (200 microL) and then injected into an HPLC-MS/MS or UPLC-MS/MS system to determine the concentration of test compound present.

Analysis

Blood and brain tissue binding were then determined using the following formulas:

Afu=Buffer/Blood or Afu=CSF/Brain

Where Afu=apparent fraction unbound; Buffer=analyte/internal standard ratio determined in the buffer compartment; Blood=analyte/internal standard ratio determined in the blood compartment; Brain=analyte/internal standard ratio determined in the brain compartment.

$$Fucr = \frac{1/D}{[(1/Afu - 1) + 1/D]}$$

where: fucr=Fraction unbound corrected; D=matrix dilution factor (D=2 for blood and D=3 for brain).

Then:

% Binding=(1−fucr)×100

% Unbound=100−% Bound

Brain/Blood Partition Ratio (Kbb) Determination

For compounds freely permeable across the blood/brain barrier (BBB), the unbound concentrations in blood and brain would be equivalent under steady-state distribution conditions. Therefore, the Kbb value could be calculated as:

Fu(blood)/Fu(brain)

which is expected to be equivalent to the brain-to-blood concentration ratio (Ct(brain)/Ct(blood)) if efflux pump transporters are not involved.

Determination of In Vivo Pharmacokinetic Parameters
Materials and Methods

Adult male rats (Charles River, Italy) were dosed with test compound orally at 1 mg/kg (5 ml/kg, in 5% v/v DMSO, 0.5% w/v HPMC in water) and intravenously at 0.5 mg/kg (2 ml/kg, in 5% v/v DMSO 40% w/v PEG400 in saline). After oral administration, blood samples were collected under deep Isofluorane anesthesia from the portal vein and heart of each rat (1 rat per time point). After intravenous administration, serial blood samples were collected from the lateral tail vein of each rat. A further group of rats (n=1 per test compound) received a single intravenous administration of the PgP transport inhibitor, Elacridar (3 mg/kg) shortly before the oral administration of the test compound at 1 mg/kg, as above. Blood and brain samples were collected at a single timepoint of 0.5 h after dose administration for these animals. In all cases, blood samples were collected into potassium EDTA tubes.

Blood and brain samples were assayed for test compound concentration using a method based on protein precipitation with acetonitrile followed by HPLC/MS-MS analysis with an optimized analytical method.

Analysis

The concentrations of test compound in blood (expressed as ng/ml) and brain (expressed as ng/g) at the different time points following either oral or intravenous dosing were analysed using a non-compartmental pharmacokinetic model using WinNonLin Professional version 4.1. The following parameters were drived:

Intravenous dosing: Maximum concentration over time (Cmax), integrated concentration over time (AUC), clearance (Clb), volume of distribution (Vss) and half-life (t1/2).

Oral dosing: Cmax, time of maximum concentration (Tmax), AUC, bioavailability (F %), fraction absorbed (Fa %), blood to brain ratio (AUC BB), and Fold-change in AUC BB in the presence of Elacridar.

In the above in vivo pharmacokinetic assay, Examples 14 and 15 were each found to demonstrate AUC BB values of at least two fold that of (5R)-5-ethyl-3-[6-(spiro[1-benzofuran-3,1'-cyclopropan]-4-yloxy)-3-pyridinyl]-2,4-imidazolidinedione (Reference Example 87 of WO2011069951A1) and 5,5-dimethyl-3-[6-(spiro[1-benzofuran-3,1'-cyclopropan]-4-yloxy)-3-pyridinyl]-2,4-imidazolidinedione (Reference Example 88 of WO2011069951A1).

Examples 14 and 15 show limited change in AUC BB in the presence of Elacridar, indicating an absence of notable p-glycoprotein interactions.

Consequently, compounds of the invention may be expected to demonstrate good availability in brain tissue.

Evaluation of the Efficacy of Modulators of Kv3 Channels in a Model of Acute Noise-Induced Hearing Loss in the Chinchilla WO2011069951A1 discloses compound (5R)-5-ethyl-5-methyl-3-[2-({4-methyl-3-[(trifluoromethyl)oxy]phenyl}oxy)-5-pyrimidinyl]-2,4-imidazolidinedione which has been identified as a modulator of Kv3.1 and 3.2 channels and is referred to herein as "COMPOUND X". Representative synthesis of COMPOUND X is provided in the synthetic schemes of WO2011069951A1 and characterising data may be found at page 137 of the published application.

The otoprotective efficacy of COMPOUND X (i.e. the ability to prevent or reduce the development of permanent acute noise-induced hearing loss) was investigated using a chinchilla model of acute noise-induced hearing loss, as follows:

Materials and Methods

Subjects comprised male, 3 year old chinchillas (Laniger), 10 animals per group. Chinchillas were housed in the study facility for a minimum of 5 days prior to noise exposure. Food and water were available ad libitum. Animals were maintained at 21° C. on a 12/12 light/dark cycle.

Vehicle and Drug Preparation and Administration

Vehicle (20% Captisol®, 0.5% w/v HPMC K15M and 0.5% w/v Tween-80™) was prepared using autoclaved deionized water not more than one week prior to use. A suspension of COMPOUND X in the vehicle at 10 mg/ml was prepared less than 24 hours prior to administration. COMPOUND X was administered at 60 mg/kg via the intraperitoneal route, with doses 12 hours apart. Five injections were given pre-noise exposure and five post-noise exposure. On the day of noise exposure, injections were given 1.5 hours before the start of noise exposure and one hour after completion of the noise exposure protocol.

Noise Exposure

Animals were placed in a sound-attenuated booth for 15 minutes prior to noise exposure. Noise exposure consisted of a 105 dB SPL octave-band noise centered at 4 kHz (TDT GNS 40× white noise generator) for 6 hours duration. The noise was routed through an attenuator (TDT PA3), a filter (Krohn-Hite 3384) and a power amplifier (Sony 55ES) to a custom-built acoustic exponential horn with a maximum output at 4 kHz using an Altec 209E driver. The loudspeaker was suspended directly above the cage. During noise exposure, animals had access to water, but not food.

Auditory Brainstem Response

Auditory brainstem responses (ABRs) were collected prior to noise exposure and 21 days after noise exposure. All animals were anesthetized throughout the ABR procedure and prior to sacrifice with a 0.3 ml/kg IM injection of 50 mg/mL ketamine, 5 mg/mL xylazine, and 1mg/kg acepromazine. Thresholds were measured in response to tonebursts with 1 ms rise/fall and a 0 ms plateau gated by a Blackman envelope and centred at the frequencies of 2, 4, 6 and 8 kHz, presented at 30/s. Two intensity series were obtained for each animal from 100 to 0 dB peak SPL in 10 dB decrements with 512 sweeps per average. The recording epoch was 15 ms following stimulus onset. Responses were analogue filtered with a 30-3000 Hz band pass. Threshold is defined as the lowest intensity capable of eliciting a replicable, visually detectable auditory brainstem response in both intensity series.

Further details of these methods can also be found in Campbell et al. (2011) Hearing Research 282, 138-144.

Data Analysis

The thresholds for ABRs at the four different sound frequencies at day 21 post-noise exposure were compared to the thresholds at baseline, prior to noise exposure in order to determine a threshold shift for each animal. The data were then analysed using a 2-way ANOVA, with treatment and frequency as main factors.

Results

In this assay, COMPOUND X significantly reduced the permanent threshold shift in ABR observed 21 days after noise exposure ($p<0.01$). Notably, this protection benefit is observed some time after administration of COMPOUND X has been ceased, indicating that the benefits are persistent. These results support the potential efficacy of COMPOUND X and of small molecule Kv3 channel modulators in general in the treatment of hearing disorders, in particular in the prevention or reduction of permanent acute noise-induced hearing loss.

Evaluation of the Efficacy of Modulators of Kv3 Channels in a Model of Central Auditory Processing Deficit Introduction Difficulty in understanding speech, in particular in a noisy environment, is a symptom of age-related hearing loss. Research has shown that deficits in central auditory processing, in particular deficits in auditory temporal processing, contribute to the difficulties in understanding speech. A measure of auditory temporal processing that has been shown to correlate with the difficulty of aged humans in understanding speech is gap detection (Mazelova J, Popelar J, Syka J. Exp Gerontol. 2003 January-February; 38(1-2): 87-94.). Deficits in gap detection are also observed in certain strains of aged rat (Syka J. Hear Res. 2010 Jun. 1; 264(1-2):70-8.), and thus can be used as a model to investigate the potential efficacy of drugs to treat central auditory processing deficits associated with age-related hearing loss.

Methods

The ability of COMPOUND X to improve auditory temporal processing in the rat, was examined using an auditory gap detection procedure in aged female Fischer 344 (F344) rats with an average age of 19.5±1.9 months, and in young F344 rats with an average age of 3 months. COMPOUND X, at doses of 30 or 60 mg/kg, or vehicle were administered via the intraperitoneal route on three test occasions using a crossover design, with an interval of at least 7 days between occasions.

Hearing thresholds in each rat were determined under anaesthesia using the auditory brainstem response (ABR) prior to the first drug administration. ABRs were recorded using subcutaneous needle electrodes in a sound attenuated chamber using pure tone bursts as stimuli (5 ms duration, frequency range 2-40 kHz).

The gap detection procedure evaluated the ability of the rats to detect short gaps in background noise by measuring the degree of inhibition that the gap afforded in the animal's startle response to a subsequent loud sound, a phenomenon known as pre-pulse inhibition (PPI). Testing was performed in a sound attenuated chamber. During the testing procedure, the rat was confined to a small wire mesh cage on a motion-sensitive platform. The animal's reflex movements were detected and transduced by a piezoelectric accelerometer. The startle response was evaluated in a 100 ms window beginning at the onset of the startle stimulus (a 110 dB SPL broad-band noise burst of 50 ms duration embedded in a background continuous broad-band noise of 65 dB SPL). Acoustic stimulation was presented via a loudspeaker placed 12 cm above the platform inside the chamber.

PPI of the startle response was induced by gaps of different durations (5-50 ms) preceding the startle stimulus by 70 ms. The degree of PPI was calculated from the startle response amplitude in the presence of the gap relative to the startle response amplitude in the absence of the gap. A two-way ANOVA with the Bonferroni post-hoc test was used to compare the degree of PPI before and after the drug applications.

Results

Average ABR audiograms in the aged F344 rats were elevated by 10-20 dB across the frequency range tested in comparison to the young F344 rats. The aged F344 rats also showed a deficit in gap-induced PPI compared to young rats indicating worsening of temporal resolution in the auditory system with age. Specifically, in a group of 10 aged rats the average PPI was significantly less than in 5 young rats at all gap durations (for example for the 30 ms gap, $p<0.001$, two-way ANOVA with Bonferroni post hoc test).

In young animals, vehicle or COMPOUND X at either 30 or 60 mg/kg tended to increase the degree of PPI, but the increases were not significant. In aged animals, the vehicle had no significant effect on the degree of PPI. However, COMPOUND X at 30 and 60 mg/kg significantly increased the degree of PPI ($p<0.001$ in each case for the 30 ms gap duration). A similar, significant improvement in PPI was also observed following treatment with COMPOUND X at 30 mg/kg at gap durations of 5, 10, and 15 ms in the aged animals.

Conclusions

These results show that, compared to young F344 rats, old rats show deficits in auditory temporal processing as measured using a gap detection paradigm. Furthermore, the data show that COMPOUND X at doses of 30 and 60 mg/kg i.p. can significantly reduce the deficit in auditory temporal processing in the aged animals. These data suggest that COMPOUND X may be effective in the treatment of central auditory processing deficits and thus may be beneficial in improving speech understanding in humans with age-related hearing loss.

Evaluation of the Efficacy of Modulators of Kv3 Channels in a Model of Tinnitus

Introduction

Chronic subjective tinnitus often emerges in human patients following noise trauma-induced hearing loss. A similar phenomenon is thought to occur in rats. Methods for determining whether rats are experiencing tinnitus following hearing loss have been developed (Turner J G. Prog Brain Res. 2007; 166:147-56).

Methods

Twenty Long Evans adult rats were exposed to a unilateral 116 dB, 16 kHz octave-band noise for one hour in order to induce hearing loss and chronic tinnitus. Ten control rats received a sham noise exposure. Approximately thirty days after the noise exposure hearing thresholds were determined for each animal. Animals were then assessed for the presence of tinnitus using a gap pre-pulse inhibition of acoustic startle paradigm similar to that described by Turner J G, Brozoski T J, Bauer C A, Parrish J L, Myers K, Hughes L F, Caspary D M. Behav Neurosci. 2006 February; 120(1): 188-95. In this test, rats were placed on a motion sensor that measured the startle amplitude of the animals in response to a sudden loud sound (115-dB SPL, 20-ms duration) emitted by a loudspeaker located in the ceiling of the cage. It is known that a brief, non-startling sound or "pre-pulse", prior to the startle sound can reduce the startle amplitude, a phenomenon known as pre-pulse inhibition. In the present study, the pre-pulse is substituted by a 50 ms silence gap in a constant sound 100 ms prior to the startle sound. If the gap is perceived by the animal, then startle response will be inhibited. However, if the animal has tinnitus, then the tinnitus sound may fill the gap and will startle as if there were no gap (reduced or absent gap pre-pulse inhibition). A drug that reduces the tinnitus will therefore restore gap pre-pulse inhibition.

The pitch of tinnitus is typically in the same range as the hearing loss, which in turn is most marked at the frequencies of the noise trauma. Thus each animal was tested for gap pre-pulse inhibition using gaps in tones of 10, 12.5, 16, 20, and 25 kHz at 60-65 dB SPL. As a control, the animals were also tested with gaps in a broadband sound of the same amplitude. Irrespective of whether the animals have tinnitus, it is unlikely that the tinnitus would fill the gap in the broadband sound, and thus this provides a control for whether the noise-trauma might have affected the gap detection ability of the rats.

Approximately half of the noise-exposed rats demonstrated deficits in auditory gap pre-pulse inhibition, consistent with the presence of tinnitus. Hearing thresholds for clicks and tone bursts at 10, 16, 20, 24, and 32 kHz were estimated from auditory brainstem responses. Thresholds were obtained before and after noise trauma, prior to drug treatment, as well as at the end of the experiment. All 30 rats were administered COMPOUND X at 30 and 60 mg/kg and vehicle via the intraperitoneal route in a counterbalanced order, with a 48-hours washout period between treatments.

Results

Hearing thresholds for the noise exposed ear, measured prior to drug treatment, were 10-20 dB SPL higher than before noise-exposure, confirming that only mild hearing loss occurred that would not interfere with the ability of the animals to perform the gap pre-pulse inhibition task.

COMPOUND X at 30 and 60 mg/kg i.p. 1-2 hours prior to testing significantly restored gap pre-pulse inhibition in the animals that showed evidence of tinnitus ($p<0.05$ and $p=0.01$ at 30 and 60 mg/kg, respectively). The drug had no effect on the gap pre-pulse inhibition of control animals or noise-exposed animals without tinnitus.

Conclusions

These results suggest that COMPOUND X has potential in the treatment of chronic tinnitus associated with noise-induced hearing loss.

All publications, including but not limited to patents and patent applications, cited in this specification are herein incorporated by reference as if each individual publication were specifically and individually indicated to be incorporated by reference herein as though fully set forth.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

What is claimed is:

1. A compound of formula (VII):

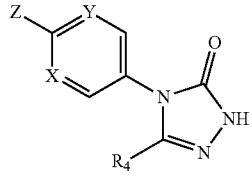

formula (VII)

wherein:
Z is F, Cl, Br or I;
X is CH;
Y is N; and
$R_4$ is methyl.

2. The compound according to claim 1, wherein Z is F.
3. The compound according to claim 1, wherein Z is Cl.
4. The compound according to claim 1, wherein Z is Br.
5. The compound according to claim 1, wherein Z is I.

* * * * *